(12) United States Patent
Natarajan et al.

(10) Patent No.: US 12,374,435 B2
(45) Date of Patent: Jul. 29, 2025

(54) METHODS FOR TREATING INFECTIONS

(71) Applicants: The Broad Institute, Inc., Cambridge, MA (US); The United States of America, as represented by the Secretary, Department of Health and Human Services, Bethesda, MD (US); Yale University, New Haven, CT (US); The General Hospital Corporation, Boston, MA (US)

(72) Inventors: Pradeep Natarajan, Boston, MA (US); Giulio Genovese, Cambridge, MA (US); Seyedeh Maryam Zekavat, New Haven, CT (US); Mitchell J. Machiela, Bethesda, MD (US); Shu-Hong Lin, Bethesda, MD (US)

(73) Assignees: The Broad Institute, Inc., Cambridge, MA (US); Yale University, New Haven, CT (US); The General Hospital Corporation, Boston, MA (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 149 days.

(21) Appl. No.: 18/121,496

(22) Filed: Mar. 14, 2023

(65) Prior Publication Data

US 2023/0290467 A1 Sep. 14, 2023

Related U.S. Application Data

(63) Continuation of application No. PCT/US2021/050658, filed on Sep. 16, 2021.

(Continued)

(51) Int. Cl.
*G16H 20/10* (2018.01)
*G16B 20/20* (2019.01)
(Continued)

(52) U.S. Cl.
CPC .............. *G16H 20/10* (2018.01); *G16B 20/20* (2019.02); *G16H 10/40* (2018.01); *G16H 50/30* (2018.01)

(58) Field of Classification Search
CPC ...................................... G16B 20/20
See application file for complete search history.

(56) References Cited

U.S. PATENT DOCUMENTS

2009/0299645 A1* 12/2009 Colby ................... G16B 20/10 506/7
2014/0121121 A1* 5/2014 Von Hoff ......... G01N 33/57488 506/8

(Continued)

FOREIGN PATENT DOCUMENTS

WO WO-2015070042 A1 * 5/2015 ........... G06F 19/327
WO 2019079493 A2 4/2019

OTHER PUBLICATIONS

Marco Tuccori, Sara Ferraro, Irma Convertino, Emiliano Cappello, Giulia Valdiserra, Corrado Blandizzi, Fabrizio Maggi & Daniele Focosi (2020) Anti-SARSCoV-2 neutralizing monoclonal antibodies: clinical pipeline, mAbs, 12:1, 1854149, DOI: 10.1080/19420862.2020.1854149 (Year: 2020).*

(Continued)

*Primary Examiner* — Sun M Li
(74) *Attorney, Agent, or Firm* — Greenberg Traurig, LLP; Melissa Hunter-Ensor; J. Nancy Costigliola

(57) ABSTRACT

The invention features methods that are useful for treatment of a patient at increased risk for infection and for selecting a patient for treatment for an infection. In various embodi- (Continued)

ments, the infection is coronavirus disease 2019 (COVID-19), sepsis, or other respiratory infections.

17 Claims, 41 Drawing Sheets

Related U.S. Application Data

(60) Provisional application No. 63/093,579, filed on Oct. 19, 2020, provisional application No. 63/079,741, filed on Sep. 17, 2020.

(51) Int. Cl.
*G16H 10/40* (2018.01)
*G16H 50/30* (2018.01)

(56) References Cited

U.S. PATENT DOCUMENTS

| | | | | |
|---|---|---|---|---|
| 2014/0370582 | A1* | 12/2014 | Von Hoff | C12Q 1/6886 435/287.2 |
| 2016/0115221 | A1* | 4/2016 | Grossman | A61K 45/06 424/159.1 |
| 2016/0237497 | A1* | 8/2016 | Rahme | G01N 33/6893 |
| 2020/0303036 | A1* | 9/2020 | Genovese | G16H 50/20 |
| 2021/0332422 | A1* | 10/2021 | Hamilton | C12Q 1/6827 |

OTHER PUBLICATIONS

Insights about clonal hematopoiesis from 8,342 mosaicnol chromosomal alterations by Po—Ru Loh'2.", Giulio Genovese23+.", Robert E Handsaker23:4, Hilary K Finucane, Yakir A * Reshef?, Pier Francesco Palamara®, Brenda M Birmann', Michael E Talkowski2:*5. 9, Samuel F Bakhoum, Nature. Jul. 2018 (Year: 2018).*

Immune defects and cardiovascular risk in X chromosome monosomy mosaicism mediated by loss of chromosome Y. A risk factor for SARS-CoV-2 vulnerability in elderly men? Luis A. Pérez-Jurado'?* , Alejandro Caceres®, Tonu Esko', Juan R. Gonzalez*, doi: https://doi.org/10.1101/2020.04.19.2007 1357; (Year: 2007).*

Rapid COVID-19 Prognostic Blood Test for Disease Severity Using Epigenetic Immune System by Adam G. Marsh, G. Mark Anderson, 2 and Erich J. Izdepski. Delaware Journal of PD Delaware Academ Yer Public Health PLA Dela J Public Health. Jul. 2020; 6(2): 26-29. PMCID: PMC8389811 (Year: 2020).*

Dehelean CA, Lazureanu V, Coricovac D, Mioc M, Oancea R, Marcovici I, Pinzaru I,Soica C, Tsatsakis AM, Cretu O: Repurposed Drugs and Novel Therapeutic Approaches—Insights into Chemical Structure-Biological Activity and Toxicological Screening. J Clin Med. Jul. 2, 2020;9(7):2084. doi: 10.3390/jcm9072084. (Year: 2020).*

Li L, Li R, Wu Z, Yang X, Zhao M, Liu J, Chen D. Therapeutic strategies for critically ill patients with COVID-19. Ann Intensive Care. Apr. 20, 2020;10(1):45. doi: 10.1186/s13613-020-00661-z. PMID: 32307593; PMCID: PMC7167303. (Year: 2020).*

Loh et al., "Insights into clonal hematopoiesis from 8,342 mosaic chromosomal alterations," Nature, 2018, vol. 559, No. 7714, pp. 350-355.

Marsh et al., "Rapid COVID-19 Prognostic Blood Test for Disease Severity Using Epigenetic Immune System Biomarkers," Delaware Journal of Public Health, Jul. 2020, vol. 6, No. 2, pp. 26-29.

Pérez-Jurado et al., "Immune defects and cardiovascular risk in X chromosome monosomy mosaicism mediated by loss of chromosome Y: A risk factor for SARS-CoV-2 vulnerability in elderly men?" medRxiv, Apr. 24, 2020, pp. 1-11.

International Search Report and Written Opinion mailed Feb. 3, 2022 in corresponding International PCT Patent Application No. PCT/US2021/050658 (14 pages).

Loh et al., "Monogenic and polygenic inheritance become instruments for clonal selection," Nature, Aug. 2020, vol. 584, No. 7819, pp. 136-141.

Peiffer et al., "High-resolution genomic profiling of chromosomal aberrations using Infinium whole-genome genotyping," Genome Research, 2006, vol. 16, pp. 1136-1148.

Terao et al., "Chromosomal alterations among age-related hematopoietic clones in Japan," Nature, Aug. 2020, vol. 584, No. 7819, pp. 130-135.

* cited by examiner

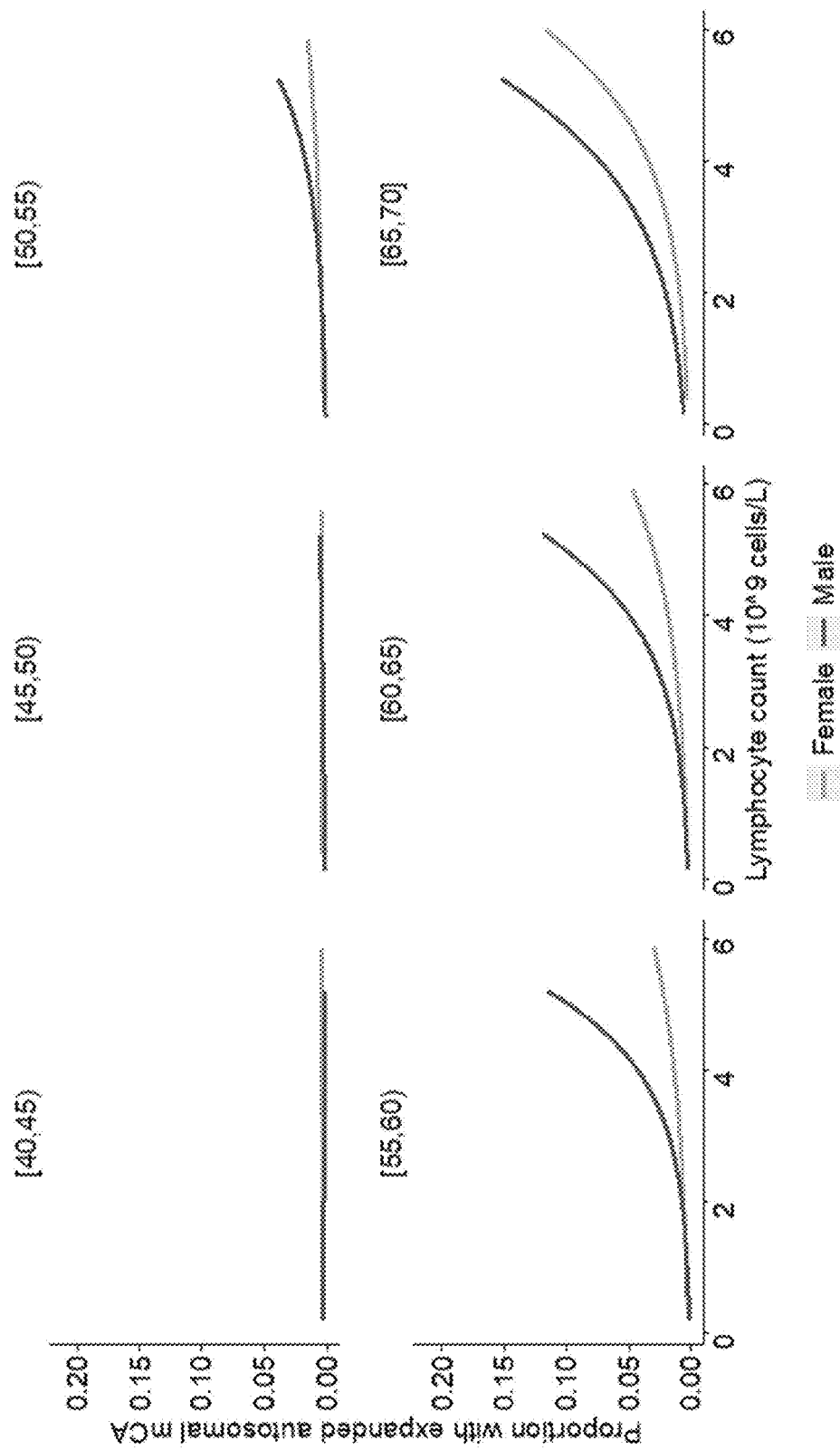

METHODS FOR TREATING INFECTIONS

CROSS-REFERENCE TO RELATED APPLICATIONS

This application is a U.S. utility application under 35 U.S.C. 111 (a) that is a continuation of PCT International Patent Application No. PCT/US2021/050658, filed Sep. 16, 2021, designating the United States and published in English, which claims priority to and the benefit of U.S. Provisional Patent Application No. 63/079,741, filed Sep. 17, 2020, and U.S. Provisional Patent Application No. 63/093,579, filed Oct. 19, 2020, the entire contents of all of which are hereby incorporated by reference herein.

STATEMENT OF RIGHTS TO INVENTIONS MADE UNDER FEDERALLY SPONSORED RESEARCH

This invention was made with government support under Grant Nos. HL142711, HL148565, HL148050, HG006855, GM136651, MH104964, HL149180, HL007208, HL092577, HL128914, ES030554, HL105780, and CP005803 awarded by the National Institutes of Health. The government has certain rights in the invention.

BACKGROUND OF THE INVENTION

With advancing age comes increased susceptibility to infectious diseases. Immunosenescence is the age-related erosion of immune function, particularly with respect to adaptive immunity. Leukocytes, including T-cells and B-cells, are key mediators of adaptive host defenses against infections, with impaired immune responses increasing risk for infections. Age-related mosaic chromosomal alterations (mCAs) detected from blood-derived DNA, are clonal large structural somatic abnormalities (deletions, duplications, or copy neutral loss of heterozygosity) present in a fraction of peripheral leukocytes that can indicate clonal hematopoiesis (CH). Mosaic chromosomal alterations (mCAs) can be associated with aberrant leukocyte cell counts, and increased risks of hematological malignancy and mortality. While the relationship between mosaic chromosomal alterations (mCAs) and increased hematopoietic cancer risk is well established, the impact of mosaic chromosomal alterations (mCAs) on immune function is poorly understood.

There remains a need to develop methods for predicting risk for infection. Further, there remains a need for developing methods for treatment and for prioritizing treatment of patients at increased risk for infection. In particular, coronavirus disease 2019 (COVID-19), an infectious disease caused by severe acute respiratory syndrome coronavirus 2 (SARS-COV-2), is an example of an infection for which there is a need for the development of these methods.

SUMMARY OF THE INVENTION

As described below, the present invention features methods for treatment of a patient at increased risk for infection and for selecting a patient for treatment for an infection.

In one aspect, the invention features a method for identifying a subject at high risk of having or developing a severe respiratory infection or sepsis. The method involves detecting the presence or absence of expanded mosaic chromosomal alterations (mCAs) in DNA derived from a blood or saliva sample of a subject using single-nucleotide polymorphism (SNP) microarray genotype intensity data, where the presence of an expanded mCA identifies the subject as at high risk of having or developing the severe respiratory infection or sepsis.

In another aspect, the invention features a method for prioritizing a subject for viral testing or vaccination. The method involves detecting the presence or absence of expanded mosaic chromosomal alterations (mCAs) in DNA derived from a blood or saliva sample of a subject using single-nucleotide polymorphism (SNP) microarray genotype intensity data, where the presence of an expanded mCA identifies the subject as at high risk of having or developing a severe respiratory infection or sepsis, thereby indicating that the subject should be prioritized for viral testing or vaccination.

In a further aspect, the invention features a method for selecting a subject for aggressive treatment for a severe respiratory infection or sepsis. The method involves detecting the presence or absence of expanded mosaic chromosomal alterations (mCAs) in DNA derived from a blood or saliva sample of a subject using single-nucleotide polymorphism (SNP) microarray genotype intensity data, where the presence of an expanded mCA identifies the subject, thereby indicating that the subject as in need of aggressive treatment for the respiratory infection or sepsis.

In some embodiments of any of the above aspects, the severe respiratory infection or sepsis is viral or bacterial. In some embodiments of any of the above aspects, the severe respiratory infection is pneumonia, COVID-19, respiratory tuberculosis, influenza, Severe Acute Respiratory Syndrome (SARS), swine flu, bird flu, whooping cough (pertussis), bronchitis, Middle East Respiratory Syndrome (MERS), pharyngitis, sinusitis, laryngitis, tracheitis, epiglottitis, pyothorax, peritonsillar abscess, abscess of lung, abscess of mediastinum, coccidioidomycosis, histoplasmosis, blastomycosis, paracoccidioidomycosis, sporotrichosis, chromomycosis, phaeomycotic abscess, sporotrichosis, chromomycosis, phaeomycotic abscess, aspergillosis, or orcryptoccosis. In some embodiments of any of the above aspects, the virus belongs to a family selected from Picornaviridae, Orthomyxoviridae, Paramyxoviridae, Coronaviridae, Pneumoviridae, and Adenoviridae. In some embodiments of any of the above aspects, the virus is severe acute respiratory syndrome coronavirus 2 (SARS-COV-2), severe acute respiratory syndrome coronavirus 1 (SARS-COV-1), influenza A, influenza B, influenza C, Severe Acute Respiratory Syndrome (SARS) virus, human metapneumovirus (hMPV), parainfluenza virus (HPIV), respiratory syncytial virus (RSV), rhinovirus, enterovirus, respiratory syncytial virus, adenovirus, or bocavirus. In some embodiments, the influenza A virus is influenza A virus subtype H1N1 (A/H1N1), influenza A virus subtype H3N2 (A/H2N2), or influenza A virus subtype H5N1 (A/H5N1). In various embodiments, the influenza B virus is influenza B virus lineage Victoria (B/Vistoria) or influenza B virus lineage Yamagata (B/Yamagata). In some embodiments of any of the above aspects, the bacterium is *Mycobacterium tuberculosis, Bordetella pertussis, Streptococcus pneumoniae, Haemophilus influenzae, Staphylococcus aureus, Streptococcus pyogenes,* or *Moraxella catarrhalis*. In various embodiments, the DNA includes peripheral blood leukocyte DNA. In some embodiments of any of the above aspects, an expanded mCAs is considered as being present when a single mCA is detected as present in the genomic DNA of at least about 10% of the subject's circulating leukocytes. In some embodiments of any of the above aspects, an expanded mCA is considered as being present if more than one mCA is detected and the mCAs collectively are present in the genomic DNA of at least about 10% of the subject's circulating leukocytes. In some embodiments of any of the above aspects, the expanded mCA comprises an autosomal mCA. In some embodiments, the expanded mCA comprises an allosomal mCA. In some embodiments, the expanded mCA comprises a mosaic loss of X chromosome (mLOX) mCA. In some embodiments, the expanded mCA comprises a mosaic loss of Y chromosome (mLOY). In some embodiments, the expanded mCA comprises a chromosome X mCA. In various embodiments, the expanded mCA comprises a chromosome Y mCA. In some embodiments of any of the above aspects, the aggressive treatment comprises hospitalization. In some embodiments of any of the above aspects, the subject is a mammal. In some embodiments, the subject is a human. In some embodiments of any of the above aspects, the method further involves identifying the subject as at high risk of having or developing a severe respiratory infection or sepsis if the subject has a history of cancer. In some embodiments, the method further involves identifying the subject as at high risk of having or developing a severe respiratory infection or sepsis if the subject has an aberrant lymphocyte cell count.

The invention provides methods for treatment of a patient at increased risk for infection and for selecting a patient for treatment for an infection. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "acute lower respiratory infection" or "severe lower respiratory infection" is meant an infection in the lungs or below the voice box that results in a subject suffering the infection needing or undergoing hospitalization. In various embodiments, an acute lower respiratory infection can cause difficulty breathing, dizziness, a fever of over 103° F., and/or loss of consciousness. In various embodiments, an acute lower respiratory infection is pneumonia or coronavirus disease 2019 (COVID-19). In some embodiments, the acute lower respiratory infection is a severe COVID-19 infection.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease or infection.

"Biological sample" as used herein means a biological material isolated from a subject. Exemplary biological samples include any tissue, cell, fluid, or other material obtained from or derived from the subject. In some embodiments, the subject is human. The biological sample may contain any biological material suitable for detecting the desired analytes (e.g., a mosaic chromosomal alteration), and may comprise cellular and/or non-cellular material obtained from the subject. The biological sample preferably comprises DNA. In particular embodiments, the biological sample is blood. Biological samples include tissue samples (e.g., cell samples, biopsy samples). Biological samples also include bodily fluids, including, but not limited to, cerebrospinal fluid, blood, lymph, blood serum, plasma, saliva, and urine. In some embodiments, the biological sample comprises blood, skin, sputum, gargles, bronchial washings, urine, semen, feces, cerebrospinal fluid, biopsies, or dried blood spots.

In this disclosure, "comprises," "comprising," "containing", and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. Any embodiments specified as "comprising" a particular component(s) or element(s) are also contemplated as "consisting of" or "consisting essentially of" the particular component(s) or element(s) in some embodiments.

"Detect" refers to identifying the presence, absence or amount of the analyte to be detected. In some embodiments, a mosaic chromosomal alteration (mCA) is detected.

By "dexamethasone" is meant a compound with CAS Number 50-02-2, chemical formula $C_{22}H_{29}FO_5$, and with the structure

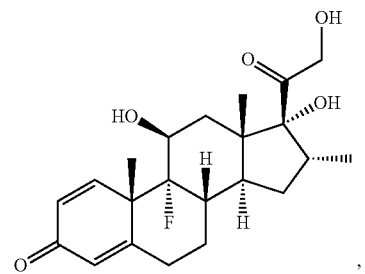

or pharmaceutically acceptable salts thereof.

By "disease" is meant any condition or disorder that damages or interferes with the normal function of a cell, tissue, or organ. The disease can be caused by an infection (e.g., a viral, eukaryotic, or bacterial infection). In one embodiment, he disease is caused by severe acute respiratory syndrome coronavirus 2 (SARS-COV-2). Examples of diseases include coronavirus disease 2019 (COVID-19), sepsis, pneumonia, and any ICD A00-B99 (certain infectious and parasitic diseases) disease. Further non-limiting examples of diseases include inflammatory diseases. In other embodiments, the disease is meningitis, encephalitis, pneumonia, coronavirus disease 2019, or gastroenteritis.

By "effective amount" is meant the amount of an agent required to ameliorate, reduce, or prevent the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "genotyping data" is meant data suitable for use in genotyping a DNA sample. In various embodiments, the DNA sample comprises genomic DNA. In various embodiments, the DNA sample comprises somatic chromosomal DNA.

By "genotyping" is meant the process of detecting variations or lack thereof in genomic makeup within a biological sample, between cells, or between subjects. Genomic makeup can include the structure of a genome as well as the sequence composition of the genome. In one embodiment, genotyping of a biological sample obtained from the subject comprises determining differences in genetic make-up between cells constituting the biological sample. Non-limiting examples of methods of genotyping include restriction fragment length polymorphism identification (RFLPI) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads.

By "incident infection" is meant an infection that a patient has acquired to change from a state of not having the infection to a state of having the infection.

By "infection" is meant the introduction into a subject of an agent and the reaction of the subject's tissues to the agent or any toxins produced by the agent. In some embodiments, the infection results in a disease. The agent can be viral, bacterial, or eukaryotic. The infection can be a respiratory system infection (e.g., an acute lower respiratory infection), a digestive system infection, an organ-level infection, a genitourinary system infection, or a nervous system infection.

By "mosaic chromosomal alterations (mCAs)" or "mosaic chromosomal abnormalities (mCAs)" are meant somatic copy number or copy neutral alterations detected in DNA derived from a sample. In some embodiments, the alterations are detected using genotyping data, where the genotyping data can be single-nucleotide polymorphism (SNP) microarray genotype intensity data. In some embodiments, mosaic chromosomal alterations (mCAs) detected from blood-derived DNA are structural somatic abnormalities present in a fraction of peripheral leukocytes. Detection of a mosaic chromosomal alteration (mCA) in blood-derived DNA can be indicative of clonal hematopoiesis. The mCAs can be detected in leukocytes or a fraction of leukocytes present in a biological sample. The mCAs can be detected in DNA gathered from a biological sample. Examples of alterations include deletions, mutations, indels, insertions, duplications, or copy neutral loss of heterozygosity. Mosaic chromosomal alterations (mCAs) can be detected from blood-derived DNA and/or saliva. DNA derived from a sample can comprise more than one mCA. The mosaic chromosomal alterations (mCAs) can be homologous chromosomal segment imbalances. An expanded mosaic chromosomal alteration (mCAs) can be indicative of clonal hematopoiesis. An expanded mosaic chromosomal alteration (mCA) may be defined as a mosaic chromosomal alteration (mCA) present in about or at least about 1%, 2%, 3%, 4%, 5%, 6%, 7%, 8%, 9%, 10%, 11%, 12%, 13%, 14%, 15%, or 20% of DNA from leukocytes and/or a biological sample from a subject. The biological sample in some embodiments is a cell fraction prepared from a biological sample and may comprise circulating blood from a subject or saliva from a subject. An expanded mosaic chromosomal alteration (mCA) may be defined as a mosaic chromosomal alteration (mCA) mutation present in no more than about 1%, 2%, 3%, 4%, 5%, 6%, 7%, 8%, 9%, 10%, 11%, 12%, 13%, 14%, 15%, or 20% of DNA from leukocytes and/or a biological sample from a subject. In some embodiments, an expanded mosaic chromosomal alteration is considered as being present in a subject if more than one mCA is detected and the mCAs are collectively present in about or at least about 1%, 2%, 3%, 4%, 5%, 6%, 7%, 8%, 9%, 10%, 11%, 12%, 13%, 14%, 15%, or 20% of DNA from leukocytes and/or a biological sample from a subject. In some embodiments, an expanded mosaic chromosomal alteration is considered as being present in a subject if more than one mCA is detected and the mCAs are collectively present in no more than about 1%, 2%, 3%, 4%, 5%, 6%, 7%, 8%, 9%, 10%, 11%, 12%, 13%, 14%, 15%, or 20% of DNA from leukocytes and/or a biological sample from a subject. In some embodiments, the mosaic chromosomal alteration (mCA) is a homologous chromosomal segment imbalance. In some embodiments, the alterations are allosomal and/or autosomal. In some embodiments, the leukocytes are peripheral leukocytes. In some embodiments, mCAs are associated with aberrant leukocyte cell counts and/or increased risks of hematological malignancy and mortality.

The terms "nucleic acid" and "nucleic acid molecule," as used herein, refer to a compound comprising a nucleobase and an acidic moiety. In various embodiments, the nucleic acid or nucleic acid molecule comprises a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, RNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O (6)-methylguanine, and 2-thiocytidine); chemically modified bases; biologically modified bases (e.g., methylated bases); intercalated bases; modified sugars (2'- e.g., fluororibose, ribose, 2'-deoxyribose, arabinose, and hexose); and/or modified phosphate groups (e.g., phosphorothioates and 5'-N-phosphoramidite linkages). In some embodiments, a nucleoside analog is a compound comprising a purine or pyrimidine in which the heterocyclic ring or sugar moiety has been altered.

As used herein, "obtaining" as in "obtaining an agent" includes synthesizing, purchasing, or otherwise acquiring the agent.

By "prevent," "preventing," "prevention," "prophylactic treatment", and the like is meant reducing the probability of developing an infection, disorder, disease, or condition in a subject, who does not have, but is at risk of or susceptible to developing the infection, disorder, disease, or condition.

By "prioritize" made with reference to a subject is meant to provide access to treatment or testing before a subject that is not prioritized. For example, in various embodiments a subject prioritized for viral testing or vaccination will be vaccinated or tested before a subject that is not prioritized for testing or vaccination. In various embodiments, a subject that is prioritized will be treated for an infection before a subject that is not prioritized. In various embodiments, a subject at higher risk for an infection or for adverse effects (e.g., hospitalization or death) resulting from an infection is prioritized over a subject that is at lower risk.

By "reduces" is meant a negative alteration of at least 1%, 5%, 10%, 25%, 50%, 75%, or 100%.

By "reference" is meant a standard or control condition. For example, a reference subject in some embodiments is a healthy subject that has recovered from an infection without hospitalization. The infection can be coronavirus disease 2019 (COVID-19). A serological test can be used to confirm that the subject has been exposed to and recovered from COVID-19.

By "remdesivir" is meant the chemical compound with CAS Number 1809249-37-3, chemical formula $C_{27}H_{35}N_6O_8P$, and chemical structure

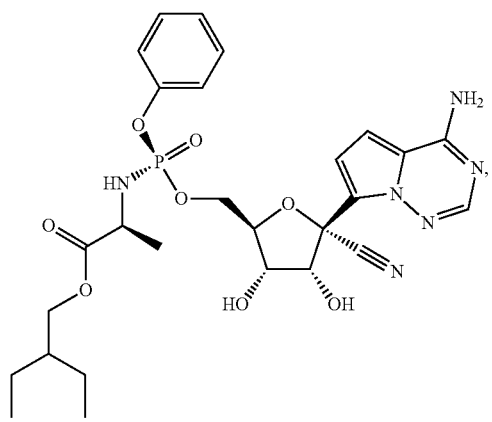 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

or pharmaceutically acceptable salts thereof.

By "single-nucleotide polymorphism (SNP)" is meant a variation at a single nucleotide position in a genome sequence across a population. In some embodiments, the population is a human population.

By "somatic abnormality" is meant a genomic mutation or other abnormality acquired by a cell that can be passed to the progeny of the cell in the course of cell division.

By "subject" or "patient" is meant a mammal, including, but not limited to, a human or non-human mammal, such as a bovine, equine, canine, ovine, or feline. In some embodiments, the subject is a human. The terms "subject" and "patient" are used interchangeably herein.

By "targeted intervention" is meant a proactive treatment of a patient at high risk of a disease or infection. An example of a targeted intervention is recommending that a patient at risk for a viral infection receive a vaccine for the virus. Another example of a targeted intervention is administering a pharmaceutical composition to a subject for preventing or treating an infection or disease if the subject is at high risk for the infection or disease. In some embodiments, a subject at high risk for an infection or for suffering adverse consequences (e.g., hospitalization or death) resulting from an infection is prioritized for a targeted intervention and/or provided with a targeted intervention.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. In some embodiments, a treatment for an infection can include treating a subject to prevent an infection (e.g., through vaccination or administration of a prophylactic drug).

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 2 shows the association of mCAs with different infectious disease categories separated by biobank and meta-analyzed effects. Individuals with prevalent hematologic cancer were excluded from analysis. Individuals with known hematologic cancer at time of or prior to blood draw for genotyping were excluded. Analyses are adjusted for age, age$^2$, sex, smoking status, and principal components of ancestry. Throughout the figures HR represents "hazard ratio", N represents number of individuals, and P represents "p-value". Throughout the figures, in the forest plots lighter boxes represent effect estimates and the darker boxes represent combined effects. Throughout the figures, in the forest plots the bounds extending from each box represent 95% confidence intervals. Throughout the figures, MGB stands for "Mass General Brigham" and UK stands for "United Kingdom."

FIG. 5A is a scatter plot showing sample-level phased B-allele frequency (BAF) auto-correlation across consecutive phased heterozygous sites versus Log R Ratio (LRR) of intensities using local GC content. FIG. 5B is a scatter plot showing sex mismatches between MoChA-derived sex computed using the chrX nonPAR region versus reported sex. Throughout the figures, F=female and M=male. Throughout the figures, BAF indicates "phased B-allele frequency" and LRR indicates "Log R Ratio".

FIGS. 13A and 13B provide plots showing the proportion of expanded autosomal mosaic chromosomal alterations (mCAs) carriers across lymphocyte count and percentage by age bin and sex. Association of expanded autosomal mosaic chromosomal alteration (mCA) prevalence with A. Lymphocyte count (FIG. 13A) and B. Lymphocyte percentage across bins of age and sex (FIG. 13B).

DETAILED DESCRIPTION OF THE INVENTION

Figure 1:
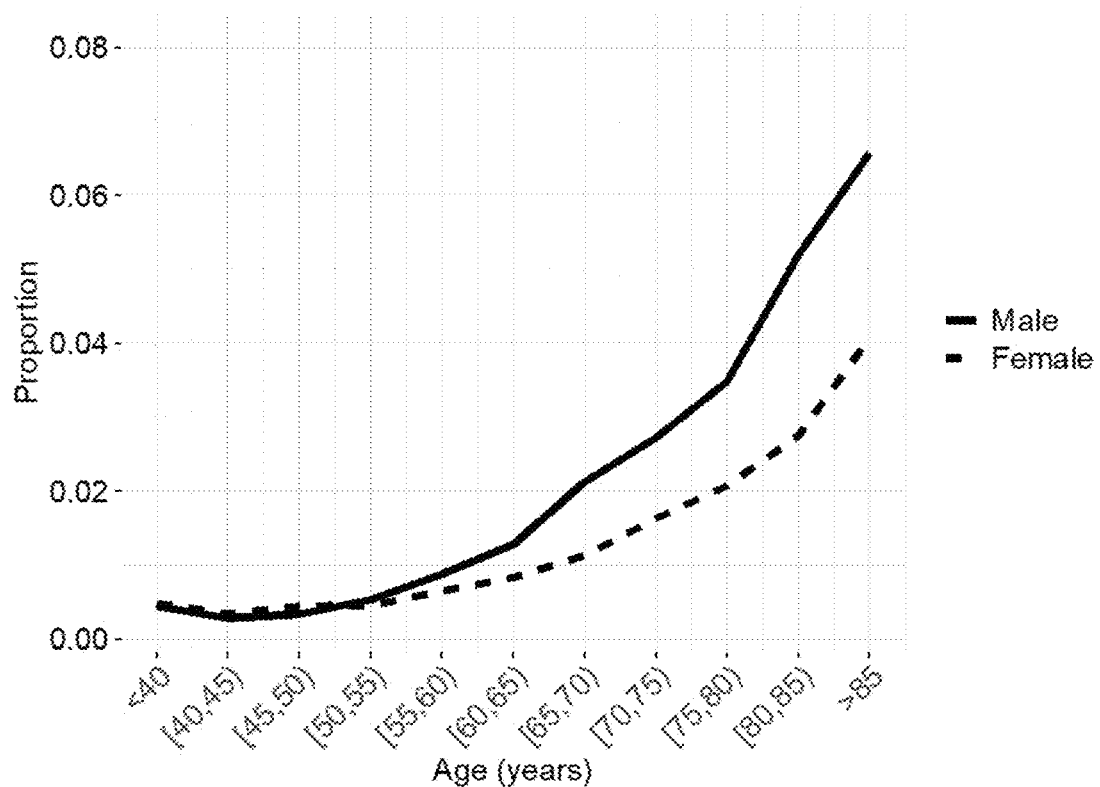
FIG. 1 is a plot showing frequency of expanded autosomal mosaic chromosomal alterations (mCAs) by 5-year age bins and by sex among individuals in the United Kingdom Biobank (UKB), Mass General Brigham Biobank (MGBB), and Biobank Japan (BBJ) combined. Individuals with known hematologic cancer at time of or prior to blood draw for genotyping were excluded. Plots by cohort are provided in FIGS. 8A-8D and 9A-9D.

The invention features methods that are useful for treatment of a patient at increased risk for infection and for selecting a patient for treatment for an infection. The invention is based at least in part upon the discovery outlined in the below provided Examples that, in addition to strongly predicting future risk of hematologic malignancy, expanded mosaic chromosomal alterations (mCAs) were also associated with risk for diverse incident infections, particularly infections causing sepsis and various respiratory infections (e.g., infections caused by severe acute respiratory syndrome coronavirus 2 (SARS-COV-2)). These findings were robust across age, sex, tobacco smoking, and were strongest among those who develop cancer.

Clonal Hematopoiesis and Infection

Consistent with these observations, expanded mosaic chromosomal alterations (mCAs) were also associated with increased odds for coronavirus disease 2019 (COVID-19) hospitalization. The below Examples provide data showing that across three geographically-distinct biobanks comprising 592,201 individuals without known hematologic malignancy, clonal hematopoiesis (CH) represented by expanded mosaic chromosomal alterations (mCAs) was increasingly prevalent with age but not readily detectable by conventional blood tests.

Not wishing to be bound by theory, mosaic chromosomal alterations (mCAs) may increase risk of infection as mosaic chromosomal alterations (mCAs) are associated with both age and potentially leukocyte function, two important contributors to infection risk. Mosaic chromosomal alterations (mCAs) are somatic variants that can increase in abundance with age and can be associated with alterations in leukocyte count. As described further in the below Examples, DNA genotyping array intensity data and long-range chromosomal phase information inferred across 592,201 multiethnic individuals from three biobanks was used to analyze the associations between expanded mosaic chromosomal alteration (mCA) clones (i.e., mosaic chromosomal alterations (mCAs) present in at least 10% of peripheral leukocyte DNA indicative of clonal expansion) and diverse infections, including severe coronavirus disease 2019 (COVID-19) from severe acute respiratory syndrome coronavirus 2 (SARS-COV-2) infection.

Mosaic chromosomal alterations (mCAs) are age-related and predispose to lymphoid or hematologic malignancies. The below provided examples demonstrate that individuals with mosaic chromosomal alterations (mCAs) are at increased risk for infection. In various embodiments, somatic copy number or copy neutral alterations or variations occur in the absence of hematologic malignancy.

The results described in the Examples provided herein support several conclusions. First, mosaic chromosomal alteration-driven clonal hematopoiesis is a potential risk factor for infection. Clonal hematopoiesis (CH) with myeloid malignancy driver mutations, also referred to as 'clonal hematopoiesis of indeterminate potential' (CHIP), predisposes to myeloid malignancy and coronary artery disease. Meanwhile, clonal hematopoiesis (CH) with larger clonal chromosomal rearrangements (i.e., mosaic chromosomal alterations (mCAs)) predisposes primarily to lymphoid malignancy but not coronary artery disease. These observations suggest clonal hematopoiesis (CH) defined by the presence of mosaic chromosomal alterations (mCAs) is a risk factor for infection. Not wishing to be bound by theory, since the relationship between mosaic chromosomal alterations (mCAs) and infection risk was not substantially attenuated when adjusting for leukocyte or lymphocyte counts at baseline visit, the impact of mosaic chromosomal alterations (mCAs) on infection risk likely acts through mechanisms independent of the impact of clonal hematopoiesis on cell counts. For example, as mosaic chromosomal alterations (mCAs) alter gene dosage (e.g., via duplications and deletions) and remove allelic heterogeneity (e.g., copy neutral loss-of-heterozygosity events) in leukocytes, potential impacts on the differentiation, function, and survival of leukocytes are mechanisms that could lead to altered infection risk. In particular, many of the mCA variants are the same lesions found in chronic lymphocytic leukemia, a condition in which lymphocyte differentiation and function is altered. Therefore, molecule changes in leukocytes that promote clonal expansion may occur at the expense of reduced ability to combat infection.

Second, the infectious disease risk associated with mosaic chromosomal alterations (mCAs) is exacerbated in the setting of cancer. Mosaic chromosomal alterations (mCAs) in blood-derived DNA increase risk for hematologic cancer. Furthermore, there may be an association between mosaic chromosomal alterations (mCAs) detected in blood-derived DNA and increased risk of select solid tumors. The Examples provided below demonstrate an interaction between mosaic chromosomal alterations (mCAs) and prior cancer that amplified sepsis and pneumonia risk. Not wishing to be bound by theory, this observation could be partially due to synergistic immunosuppressive side effects of cancer therapies. Alternatively, abnormal regulation of immune inflammatory pathways that release cytokines and inflammatory cells may create chronic states of inflammation in individuals with mosaic chromosomal alterations (mCAs). Surveillance for expanded mosaic chromosomal alteration (mCA) clones, particularly among those who develop cancer, may help identify individuals at high risk for infection that could benefit from targeted interventions.

Third, the findings presented in the below Examples could have particular relevance for the ongoing coronavirus disease 2019 (COVID-19) pandemic. As discussed further in the Examples below, mosaic chromosomal alterations (mCAs) are associated with elevated risk for coronavirus disease 2019 (COVID-19) hospitalization, with greater than two-fold risk linked to expanded autosomal mosaic chromosomal alterations (mCAs). Maladaptive immune responses, particularly in leukocytes, can increase risk for severe coronavirus disease 2019 (COVID-19) infections. Awareness of coronavirus disease 2019 (COVID-19) risk associated with mosaic chromosomal alterations (mCAs) may help with the prioritization of emerging prophylactic treatments and initial vaccination programs.

The below Examples provide evidence for increased susceptibility to a spectrum of infectious diseases in individuals carrying mosaic chromosomal alterations (mCAs) in a detectable fraction of leukocytes particularly when cancer is concurrently present. The impacts of mosaic chromosomal alteration (mCA) on infection risk were systemic, with increased susceptibility to infection observed for a variety of organ systems, including severe coronavirus disease 2019 (COVID-19) presentations.

Detection of mCAs

Mosaic chromosomal alterations (mCAs) may be detected in DNA of a biological sample by a number of techniques. The DNA can be genomic DNA. In some embodiments, a mosaic chromosomal alteration can be detected by the methods described in PCT/US2018/056342. The detection method can include detecting somatic structural variants from genotyping data. In some embodiments mCAs can be detected using the methods described in Loh P R, Genovese G, Handsaker R E, et al. "Insights into clonal haematopoiesis from 8,342 mosaic chromosomal alterations," Nature (2018) 559:350-5; in Loh P R, Genovese G, McCarroll S A, "Monogenic and polygenic inheritance become instruments for clonal selection," Nature 2020; or in Terao C, Suzuki A, Momozawa Y, et al. "Chromosomal alterations among age-related haematopoietic clones in Japan," Nature (2020). In some embodiments, mCAs can be detected by combining methods described in any of the references cited herein and/or those methods described herein.

Mosaic chromosomal alterations (mCAs) can be detected in genotyping data gathered from a DNA sample. The mCAs can be detected using various methods in statistics. Blood-derived DNA from a biological sample can be analyzed to detect an mCA therein using any of the methods described herein. Analyzing the DNA sample can include preparing genotyping data for the DNA sample (e.g., using a DNA microarray). The genotyping data can be single nucleotide polymorphism (SNP)-array genotype intensity data. In some embodiments, the genotyping data is whole exome sequence data. In various embodiments, the genotyping data is whole genome sequencing data. Genotyping data can be obtained by genotyping a biological sample using any of the various methods discussed herein. The intensity data can be allele-specific SNP-array intensity data from blood genotyping. The biological sample can be a blood sample. An mCA can be detected using long-range phase information. Phase-based mCA detection can be carried out using statistical methods.

Various methods can be used to detect mCAs in genotyping data. The methods of the present invention in various embodiments are not limited to any particular method for detecting an mCA. A variety of methods are available for detecting an mCA in genotyping data and the invention of the disclosure in various embodiments is not limited to any particular detection method.

In an exemplary embodiment, mCAs in genotyping data gathered for a biological sample can be detected by first transforming genotype intensities to log 2 R ratio (LRR) and B-allele frequency (BAF) values to estimate total and relative allelic intensities, respectively. The method can comprise masking constitutional segmental duplications. The masking may comprise modeling observed phased BAF deviations (pBAFs). The method can include re-phasing performed using Eagle2. Modeling observed pBAFs may be performed by modeling across individual chromosomes using a 25-state hidden Markov model (HMM) with states corresponding to pBAF values. Mosaic chromosomal alteration (mCA) calling performed by leveraging long-range phase information to search for allelic imbalances between maternal and paternal allelic fractions across contiguous genomic segments. In some embodiments, constitutional duplications and low-quality calls are filtered out and cell fraction estimated. mCAs can be detected according to any of the methods described in the Examples and accompanying methods provided herein. In some embodiments, an mCA can be detected using hidden Markov models (HMMs).

In an exemplary embodiment, a method for detecting an mCA in a DNA sample using genotyping data includes acquiring genotyping data using techniques available in the art. In certain embodiments, determining total and relative allelic intensities from genotyping data will comprise converting genotype array intensity data. In certain embodiments, converting genotype array intensity data may comprise converting the genotype array intensity data into log 2R ratio (LRR) and B allele frequency (BAF) values.

A computer-implemented method can be used to detect a mosaic chromosomal alteration (mCA). The method can involve determining, using one or more computing devices, total and relative allelic intensities for one or more samples (e.g., where each sample is DNA derived from a biological sample). The method can also involve, masking, using the one or more computing devices, constitutional segmental duplications in each sample of the one or more samples. The method can further involve, identifying, using the one or more computing devices, a putative set of mCAs for each sample in the one or more samples. The method can also include defining, using the one or more computing devices, one or more mCAs for each sample of the one or more samples, based at least in part on application of a likelihood ratio test to the putative set of mCAs. The method can also involve locating, using the one or more computing devices, a chromosomal location of each identified mCA for each sample in the one or more samples. The method can further involve using one or more computing devices to determine a copy number of each mCA for each sample. Determining the total and relative allelic frequencies can comprise converting genotype array intensity data into log 2 R ratio (LRR) and B allele frequency (BAF) values. Allelic frequencies can be determined from genotype data.

In various embodiments, masking the constitutional segmental duplications comprises modeling, using the one or more computing devices, observed phased BAF deviations (pBAF). Modeling the observed pBAFs can be performed by modeling across individual chromosomes using a 25-state hidden Markov model (HMM) with states corresponding to pBAF values. The method can comprise selecting regions to mask, which comprises computing the Viterbi path through the HMM and examining contiguous regions of nonzero states. Identifying the putative set of mCAs can comprise use of a 3-state HMM. The 3-state HMM can be parameterized by a single parameter representing mean |ABAF| (where ABAF means average/mean BAF) within a given mCA. In various embodiments, locating the chromosomal location of each identified mCA comprises taking about 5 samples from the posterior of the 3-state HMM and determining the boundaries of each SV event based on a consensus of the about 5 samples. In some embodiments, determining the copy number of each identified mCA comprises determining a relative probability that the event was a loss, CNN-LOH (copy-number neutral loss of heterozygosity), or gain based at least in part on the log 2 ratio (LRR) and |ABAF| deviation. Detecting multiple sub-clonal events can comprise re-analyzing each identified mCA using Viterbi decoding on a 51-state HMM with |ABAF| levels ranging from 0.01 to 0.25 in multiplicative increments.

In some embodiments, the detection method comprises using likelihood ratio statistics to call the existence of a mosaic chromosomal alteration (mCA). In some embodiments, calling the existence of an mCA comprises analysis of a sequence of observed phased BAF deviation on each chromosome and determining whether the phased BAF deviation can be explained by the presence of mosaic chromosomal alterations.

In an exemplary embodiment, mosaic chromosomal alterations (mCAs) are detected in a DNA sample using genotyping intensities and long-range haplotype phase. Mosaic chromosomal alterations (mCAs) can be detected in genotyping intensity data from a DNA sample using statistical phasing data having chromosome-scale accuracy. In some embodiments, the method comprises using long-range phase information to search for local imbalances between maternal and paternal allelic fractions in a cell population. The method can enable considerable gains in sensitivity for detection of large events at low cell fractions. The method can comprise transforming genotyping intensities to $\log_2$ R ratio (LRR) and B-allele frequency (BAF) values (which measure total and relative allelic intensities, respectively) after affine-normalization and GC wave-correction. The method can include the use of a hidden Markov model to detect BAF deviations. The detection method can further comprise quality control steps to filter out potential technical artifacts in a data set.

The mosaic chromosomal alterations can be detected from genotyping data gathered using nucleic acids (e.g., DNA) from a biological sample collected from a subject. The biological sample may be a fluid, e.g., a biological fluid. Non-limiting examples of biological fluids include blood, serum, plasma, sputum, lymph, lavage fluid, cerebrospinal fluid, urine, semen, sweat, tears, saliva, and the like. As used herein, the terms "lymph", "blood", "plasma", and "serum" encompass fractions or processed portions thereof. In some embodiments, the biological sample comprises leukocytes. The leukocytes can be peripheral blood leukocytes. The leukocytes can be circulating or peripheral blood leukocytes. The biological sample can be taken from a biopsy, swab, smear, etc. and includes a processed fraction or portion derived therefrom. The sample can be blood, which may include or be lymph. The sample can be saliva. In various embodiments, clonal hematopoiesis (e.g., an expanded mCA) is detected using DNA obtained from saliva.

The method can include detecting an mCA in a fraction of leukocytes or in a cell fraction of a blood fraction from a subject. The method can include determining what percentage of leukocytes or of cells in the blood fraction of a subject comprise a detectable mCA.

An mCA can be allosomal and/or autosomal. Allosomal mCAs (alternatively "sex chromosome mCAs) include mosaic loss of X chromosome (mLOX) mCAs, loss of Y chromosome (mLOY) mCAs, chromosome X mCAs, and chromosome Y mCAs.

Viral Diagnostics

Any of various techniques known in the art can be used to diagnose a subject as having a viral infection. Diagnosing a patient with a viral infection can include gathering a biological sample from the subject and testing the sample for the presence of the virus. If the virus is present in the sample, the subject can be considered as being infected by the virus. For example, a polymerase chain reaction (PCR) test can be used to detect a virus in a subject. As a non-limiting example, a severe acute respiratory syndrome coronavirus 2 (SARS-COV-2) infection can be determined by polymerase chain reaction from nasopharyngeal, oropharyngeal, or lower respiratory samples. Further examples of tests available to diagnose a patient with a viral infection include rapid antigen detection tests (RADTs), direct fluorescent antibody (DFA) testing, viral culture, hemagglutination assay, electron microscopy, and single or multiplex nucleic acid amplification testing (e.g., PCT). Serological testing can be used to determine whether or not a patient has previously been exposed to a virus. Any of the various virus diagnostic or virus identification tests published by The Associated Regional and University Pathologists (ARUP), all of which are incorporated herein by reference in their entirety for all purposes, can be used in the various embodiments of the present invention to detect a viral infection in a subject.

In various embodiments, a viral infection can be detected based upon symptoms displayed by a subject. For example, a subject may be diagnosed with coronavirus disease 2019 (COVID-19) if displaying symptoms of fever, chills, cough, shortness of breath, difficulty breathing, fatigue, muscle aches, body aches, headache, new loss of taste, new loss of smell, sore throat, congestion or runny nose, nausea or vomiting, diarrhea, persistent pain or pressure in the chest, new confusion, inability to wake or stay awake, bluish lips or face, or a combination thereof.

Bacterial Diagnostics

Any of various techniques known in the art can be used to diagnose a subject as having a bacterial infection. Diagnosing a patient with a bacterial infection can include gathering a biological sample from the subject and testing the sample for the presence of the bacterium. If the bacterium is present in the sample, the subject can be considered as being infected by the bacterium. For example, a polymerase chain reaction (PCR) test can be used to detect a bacterium in a subject. Further non-limiting examples of methods by which a bacterial infection may be diagnosed include cell culture, antibiotic sensitivity testing, Gram staining, various techniques in microscopy, enzyme-linked immunosorbent assay (ELISA), serological tests, rapid plasma region tests, blood culture, procalcitonin tests, C-reactive protein (CRP) tests, full blood counts, and coagulase tests. For example, if an infectious or pathogenic bacterium is cultured from a biological sample from a subject, then the subject may be considered as being infected by the bacterium. Any of the various bacterial diagnostic or viral identification tests published by The Associated Regional and University Pathologists (ARUP), all of which are incorporated herein by reference in their entirety for all purposes, can be used in the various embodiments of the present invention to detect a bacterial infection in a subject.

In various embodiments, a viral infection can be detected based upon symptoms displayed by a subject.

Methods for Selecting a Subject for Treatment

In one aspect the invention provides a method for administering a treatment to prevent, reduce, or ameliorate an infection in a selected subject. In another aspect, the invention provides a method for selecting a subject for a treatment to prevent, reduce, or ameliorate an infection. In a further aspect, the invention provides for a method for identifying a subject at high risk of having or developing a severe respiratory infection. The invention also provides a method for identification of a subject as being at risk of hospitalization or even death resulting from an infection. In various embodiments, the subject is selected or identified if the subject has a detectable mCA in a fraction of cells in a biological sample obtained from the subject. The biological sample can be a blood sample. The biological sample can be leukocytes obtained from the subject. In some embodiments, the subject is selected if the subject has a high risk of infection.

Certain prevalent or emergent infections, such as coronavirus disease 19 (COVID-19), present the challenge of having to properly prioritize the allocation of limited treatment resources to patients in need of treatments for the infections. Therefore, the present invention provides methods for prioritizing the treatment of subjects at higher risk for infection or developing a disease than the general population. Those subjects at high risk for an infection can be prioritized for treatment for the infection relative to subjects at lower risk for infection. The method can include identifying a subject as being at high or accelerated risk for an infection and then administering a treatment for the infection to the identified subject.

The methods herein include administering to the subject (including a subject identified as in need of such treatment) an effective amount of an agent, or a composition to produce a desired effect (e.g., treatment of an infection). The agent can be a vaccine. The vaccine can be a vaccine for prevention or treatment of coronavirus disease 19 (COVID 19). Identifying a subject in need of such treatment can be in the judgment of a subject or a health care professional informed by the objective criteria described herein (e.g., detection of an expanded mosaic chromosomal alteration in the subject).

The therapeutic methods of the invention (which include prophylactic treatments) in general comprise administration of a therapeutically effective amount of an agent for treatment of an infection or disease (such as a vaccine composition) to a subject (e.g., animal, human) in need thereof, including a mammal, particularly a human. Such treatment will be suitably administered to subjects, particularly humans, suffering from, having, susceptible to, or at risk for an infection, disease, or symptom thereof. In some embodiments, determination of those subjects "at risk" is made by an objective determination using the methods described herein.

The examples provided herein demonstrate that certain factors correlate with an increased risk of infection or diseases caused by an infection in a subject. In particular, the examples show that subjects having blood cells (e.g., leukocytes) with a detectable mCA are at increased risk for infections. For example, subjects with a detectable mCA in a fraction of their leukocytes have an increased probability of being hospitalized for a severe acute respiratory syndrome coronavirus 2 (SARS-COV-2) infection. In some embodiments, subjects with a detectable mCA have increased risk of infection, including severe coronavirus disease 2019 (COVID-19). Also, subjects with a detectable mCA, which can include multiple different mCAs in some embodiments, in a fraction of their leukocytes have an increased risk of an infection resulting in pneumonia or sepsis. In various embodiments, a subject is identified as being at high or accelerated risk of infection relative to a reference subject not having a detectable mCA or having an mCA detectable in a lower fraction of their leukocytes if the subject has a detectable mCA in about or at least about 1%, 2%, 3%, 4%, 5%, 6%, 7%, 8%, 9%, 10%, 11%, 12%, 13%, 14%, 15%, or 20% of the subject's leukocytes. In some embodiments, the subject is considered as being at high risk if the subject has an mCA detectable in a fraction of the subject's leukocytes and the subject also has a history of cancer. The cancer can be a blood cancer, such as a hematopoietic or hematologic cancer (e.g., leukemias, myelomas, and lymphomas). In some embodiments, a subject is considered as being at higher risk for adverse effects (e.g., hospitalization, loss of organ function, lung or other tissue damage, death of tissue, or subject death) resulting from an infection if an expanded mCA is detected as being present in blood-derived DNA of the subject. The cancer can be a solid tumor in some embodiments. In various embodiments, leukocytes of the subject typically do not comprise a myeloid malignancy driver mutation (also known as a clonal hematopoiesis of indeterminate potential (CHIP) mutation), such as those described in Loh, Po-Ru, et al, "Monogenic and polygenic inheritance become instruments for clonal selection," *Nature* 584:136-141 (2020). In various embodiments, the myeloid malignancy driver mutation is JAK2 V617F. In some embodiments, the myeloid malignancy is associated with lymphoid or hematologic malignancies. In various embodiments, the expansion does not arise in hematopoietic stem or progenitor cells. In various embodiments, the expansion co-occurs with a measured increase in lymphocyte counts relative to a reference subject not having an expanded mCA.

In some embodiments, the subject may be considered to be at higher risk for infection if the subject has an aberrant lymphocyte cell count.

Methods of Treatment

In various aspects, the present invention provides a method for prioritizing a subject for viral testing or vaccination. In another aspect, the present invention provides a method for selecting a subject for aggressive treatment for a severe respiratory infection or sepsis. In some aspects, the present invention provides a method for prioritizing a subject for administration of a composition, wherein the composition is a treatment or prophylactic for an infection of interest.

The present invention provides methods of treating disease and/or disorders or symptoms thereof which comprise administering a therapeutically effective amount of a pharmaceutical composition (e.g., a vaccine) to a subject (e.g., a mammal such as a human). Thus, one embodiment is a method of treating a subject suffering from or susceptible to a respiratory disease, sepsis, or symptom thereof. The method includes the step of administering to the mammal a therapeutic amount of a pharmaceutical composition to treat or prevent the disease or disorder or symptom thereof, under conditions such that the disease or disorder is treated or prevented.

The pharmaceutical composition can be an antibiotic composition. The pharmaceutical composition can be a vaccine. Non-limiting examples of vaccines include SARS severe acute respiratory syndrome coronavirus 2 (SARS-COV-2) vaccines. In some embodiments, the vaccine is a vaccine for a virus belonging to a families selected from Picornaviridae, Orthomyxoviridae, Paramyxoviridae, Coronaviridae, Pneumoviridae, and Adenoviridae. The vaccine can be for SARS-COV-2, influenza A, influenza B, influenza C, Severe Acute Respiratory Syndrome (SARS) virus, human metapneumovirus (hMPV), parainfluenza virus (HPIV), respiratory syncytial virus (RSV), rhinovirus, enterovirus, respiratory syncytial virus, adenovirus, or bocavirus.

Non-limiting examples of antibiotic compositions include antibiotic compositions inhibiting growth, killing, and/or lysing *Mycobacterium tuberculosis, Bordetella pertussis, Streptococcus pneumoniae, Haemophilus influenzae, Staphylococcus aureus, Streptococcus pyogenes,* or *Moraxella catarrhalis* cells. Non-limiting examples of antibiotics include azithromycin, amoxicillin/clavulanate, clindamycin, cephalexin, cefalosporin, cefalexin, sulfamethoxazole/trimethoprim, trimethoprim, norfloxacin, penicillins (e.g., amoxicillin and flucloxacillin), streptomycin, neomycin, kanamycin, paromomycin, vancomycin, teicoplanin, ciprofloxacin, levofloxacin, trovafloxacin, linezolid, posizolid, tedizolid, cycloserine, prontosil, sulfanilamide, sulfadiazine, sulfixoxazole, tetracycline, augmentin, lymecycline, oxytetracycline, erythromycin, clarithromycin, minocycline, azithromycin, geldanamycin, rifamycin, naphthomycin, pristinamycin IIA, rifampicin, pivmecillinam, pristinamycin IA, daptomycin, surfactin, metronidazole, nystatin, amphotericin, ofloxacin, doxycycline, fucithalmic, gentamycin, fluconazole, and combinations thereof. The antibiotic can be a beta-lactam, an aminoglycoside, a chloramphenicol, a glycopeptide, a quinolone, an oxazolidinone, a sulfonamide, a tetracycline, a macrolides, an ansamycin, a streptogramin, or a lipopeptide.

If a subject is at high risk for developing an infection, treatment of the subject should be prioritized over a subject at lower risk. Further, if the patient is at high risk of being hospitalized for an infection and is presently suffering the infection, then the patient should be provided with aggressive treatment for the infection. The aggressive treatment can include immediate hospitalization and/or careful ongoing monitoring of the patient's condition. A patient at high risk of adverse consequences (e.g., hospitalization or death) resulting from an infection should be provided with aggressive treatment and care to prevent, abate, or reduce the adverse consequences. The aggressive treatment can include immediate vaccination of the patient for a bacterium or virus causing the infection. A patient at high risk for an infection should be advised of the high risk and given prioritized access to personal protective equipment, medical care, tests for the infection, and/or vaccination to avoid infection and given appropriate literature and educational materials and instruction to help the patient take proactive measures (e.g., self-quarantining, social-distancing, and/or wearing of personal protective equipment) to avoid infection. In some embodiments, aggressive medical care includes prioritized access to testing for an infection and/or frequent testing for infection (e.g., weekly, bi-weekly, or monthly). Aggressive medical care can also include frequent medical check-ups to assess patient health status. In some embodiments, a frequent medical check-up is once a week, bi-weekly, monthly, or bi-monthly. Aggressive medical treatment can also include prioritizing patient access to medicines targeting an infection.

As vaccines are developed for emergent viral infections (e.g. SARS severe acute respiratory syndrome coronavirus 2 (SARS-COV-2)), vaccine supplies can be initially limited and demand high. Therefore, there is a need to prioritize access to the vaccine supplies so that subjects in most need of vaccination are vaccinated before subjects in less need. In general, when demand for medical treatment exceeds available supplies, there is a need for prioritization of subjects for treatment. Thus, the present invention provides for methods for prioritizing a subject for vaccination. Similarly, during a pandemic or epidemic, demand for tests for a particular infection causing the pandemic or epidemic can be in short supply. Therefore, the present invention also provides methods for prioritizing testing of subjects at highest risk of suffering acute adverse effects (e.g., hospitalization) from an infection.

The methods herein include administering to the subject (including a subject identified as in need of such treatment) an effective amount of a pharmaceutical composition to produce a treatment or preventative effect. Identifying a subject in need of such treatment can be in the judgment of a subject or a health care professional informed by one of those criterion described herein.

The therapeutic methods of the invention in general comprise administration of a therapeutically effective amount of a pharmaceutical composition to a subject in need thereof, including a mammal, particularly a human. The therapeutic methods of the invention can include prioritizing treatment of a patient based upon risk of infection. Treatment will be suitably administered to subjects, particularly humans, suffering from, having, susceptible to, or at risk for a disease, disorder, or symptom thereof. Determination of those subjects "at risk" can be made according to any one or a plurality of the criteria described herein.

The treatment administered to the patient may be any treatment available to a medical professional for preventing, ameliorating, or reducing an infection or a disease resulting therefrom or symptoms thereof. For example, the treatment can comprise administering one of the compositions described herein. The treatment can be a cell therapy or a gene therapy. Cell therapies include cellular immunotherapies and other types of both autologous and allogenic cells, such as stem cells, and the like. Gene therapies seek to modify or manipulate expression of a gene or to alter the biological properties of living cells in a subject.

In various embodiments, the composition (e.g., a pharmaceutical composition) can comprise an agent falling into one or more of the following categories: an antiviral drug, a complement inhibitor (e.g., ravulizumab-cwvz, eculizumab), engineered cells, inactivated virus (e.g., inactivated severe acute respiratory syndrome coronavirus 2 (SARS-COV-2)), a virus-like particle, a non-replicating viral vector, a replicating viral vector (e.g., a viral vector comprising a fragment derived from severe acute respiratory syndrome coronavirus 2 (SARS-COV-2)), an immunogenic polypeptide, an anti-inflammatory drug, an immunosuppressant, a steroid (e.g., dexamethasone), a nucleoside analog (e.g., remdesivir), convalescent plasma, and a monoclonal antibody (e.g., tocilizumab or sarilumab). In various embodiments, convalescent plasma is antibody-containing plasma obtained from a patient that has successfully recovered from coronavirus disease 2019. In some embodiments, the composition comprises a cocktail of antibodies (e.g., REGN-COV2). In some embodiments, the composition is derived from convalescent plasma and/or comprises antibodies selected from convalescent plasma. In some embodiments, the composition comprises one or more of acalabrutinib, tofacitinib, ruxolitinib, baricitinib, anakinra, canakinumab, apremilast, mavrilimumab, fragments thereof, and various combinations thereof. In some embodiments, the composition comprises one or more of azithromycin, lopinavir/ritonavir, oseltamivir, favipiravir, arbidiol, galidesivir, colchicine, ivermectin, various combinations thereof, and pharmaceutically acceptable salts thereof. In some embodiments, the composition comprises a direct-acting antiviral (e.g., protease, helicase, and polymerase inhibitors) and/or an immunomodulator (e.g., interferons and corticosteroids). In some embodiments, the nucleoside analog comprises ribavirin, remdesivir, $\beta$-d-N4-hydroxycytidine, BCX4430, remcitabine hydrochloride, 6-azauridine, mizoribine, acyclovir fleximer, a pharmaceutically acceptable salt thereof, or a combination thereof. In some embodiments, the composition comprises one or more monoclonal antibodies. In some embodiments, the composition is a vaccine.

In some embodiments, the aggressive treatment comprises use of a device or machine. In some embodiments, the device or machine filters a patient's blood to remove excess proteins or toxins.

Non-limiting examples of infections that may be treated by the methods of the invention include pneumonia, sepsis, COVID-19, infections of central nervous system, bacterial infections, and respiratory tuberculosis.

Kits

The invention provides kits for treating an infection in a subject and/or identifying a subject having or at risk of developing the infection. A kit of the invention can include reagents and equipment for extraction and purification of DNA from a biological sample and subsequent analysis of the DNA to detect mosaic chromosomal alterations (mCAs).

In some embodiments, the kit includes reagents suitable for DNA sequencing or microarray-based analysis of a DNA sample.

The kits may further comprise a therapeutic composition comprising one or more agents for treating an infection. In some embodiments, the agent is a vaccine or a treatment for coronavirus disease 2019 (COVID-19). The kits may comprise diagnostic reagents for testing a subject for a bacterial or viral infection according to any of the methods described herein.

In some embodiments, the kit comprises a sterile container which contains a pharmaceutical composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, the kit further comprises instructions for using the diagnostic reagents and/or administering a pharmaceutical composition. The kit can include instructions for the analysis of DNA isolated from the subject to assess risk of the subject for infection or development of a serious disease resulting from the infection. In particular embodiments, the instructions include at least one of the following: description of the therapeutic agent; dosage schedule and administration for reducing infection or disease symptoms; precautions; warnings; indications; counter-indications; over dosage information; adverse reactions; animal pharmacology; clinical studies; instructions on how to analyze a DNA sample; instructions on how to detect mosaic chromosomal alterations in a sample; instructions on how to assess subject risk for infection or disease; and/or references. The instructions may be printed directly on the container (when present), or as a label applied to the container, or as a separate sheet, pamphlet, card, or folder supplied in or with the container. The instructions can be provided in digital form on a portable data storage medium (e.g., a compact disk or USB drive) or stored remotely on a server that can be accessed remotely.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Population Characteristics and Mosaic Chromosomal Alteration (mCA) Prevalence A total of 592,201 unrelated, multi-ethnic individuals across the United Kingdom Biobank (UKB) (N=444,199), Mass General Brigham Biobank (MGBB) (22,461), and Biobank Japan (BBJ) (N=125,541) passing genotype and mosaic chromosomal alteration (mCA) quality control criteria were analysed (Table 1). Among the United Kingdom Biobank (UKB) participants, mean age at DNA collection was 57 (standard deviation [SD] 8) years, 204,579 (46.1%) were male, 188,875 (45.0%) were prior or current smokers, and 66,551 (15.0%) had a history of solid cancer. In the Mass General Brigham Biobank (MGBB), mean age was 55 (SD 17) years, 10,306 (45.9%) were male, 9,094 (40.5%) were prior or current smokers, and 6,080 (27.1%) had a history of solid cancer. In Biobank Japan (BBJ), mean age was 65 (SD 12) years, 72,186 (57.5%) were male, and 66,913 (53.3%) were prior or current smokers.

TABLE 1

Baseline summary statistics across the United Kingdom (UK) Biobank, Mass General Brigham (MGB) Biobank, and Biobank Japan among individuals analyzed. SD means "standard deviation".

|  | UK Biobank | MGB Biobank | Biobank Japan |
| --- | --- | --- | --- |
| N | 444,199 | 22,461 | 125,541 |
| Age of DNA collection (mean (SD)) | 56.5 (8) | 55.0 (16.8) | 64.6 (12.4) |
| Sex (Male (%)) | 204,579 (46.1%) | 10,306 (45.9%) | 72,186 (57.5%) |
| Prior or Current Smoker (%) | 188,875 (45.0%) | 9,094 (40.5%) | 66,913 (53.3%) |
| Race | White: 417,828 (94.1%) Asian: 10,277 (2.3%) Black: 7,173 (1.6%) Mixed: 2,634 (0.6%) Other: 4,160 (0.9%) Unknown 187 (0.04%) | White: 18,933 (84.3%) Asian: 569 (2.5%) Black: 1,056 (4.7%) Other: 744 (3.3%) Unknown: 1,159 (5.2%) | Asian: 125,541 (100%) |
| BMI (mean (SD)) | 27.4 (4.8) | 28.5 (6.2) | 23.4 (3.7) |
| Prevalent Solid Cancer | 66,551 (15.0%) | 6,080 (27.1%) | 25,987 (20.7%) |
| Prevalent Type 2 Diabetes | 10,835 (2.4%) | 1,782 (7.9%) | 31,636 (25.2%) |
| Prevalent Coronary Artery Disease | 25,287 (5.7%) | 3,908 (17.4%) | 23,099 (18.4%) |
| Prevalent Hypertension | 129,888 (29.2%) | 11,010 (49.0%) | 37,913 (30.2%) |
| Prevalent Hypercholesterolemia | 66,483 (15.0%) | 9,881 (44.0%) | 35,026 (27.9%) |

TABLE 2

Mosaic chromosomal alterations (mCA) counts by cohort.

|  | UK Biobank | MGB Biobank | Biobank Japan |
| --- | --- | --- | --- |
| N | 444,199 | 22,461 | 125,541 |
| Any mCA(%) | 66,011 (14.9) | 3,784 (16.8) | NA |
| Autosomal mCA (%) | 15,350 (3.5) | 1,025 (5.2) | 20,440 (16.3) |
| ChrX (%) | 12,265 (5.1) | 820 (7.0) | NA |
| ChrY (%) | 41,284 (20.1) | 2,201 (22.0) | NA |
| Any expanded mCA (%) | 12,398 (3.2) | 1,026 (5.2) | NA |
| expanded autosomal mCA (%) | 2,985 (0.8) | 337 (1.8) | 1,676 (1.3%) |
| expanded ChrX (%) | 397 (0.2) | 44 (0.2) | NA |
| expanded ChrY (%) | 9168 (4.5) | 669 (3.4) | NA |

Figure 7A:
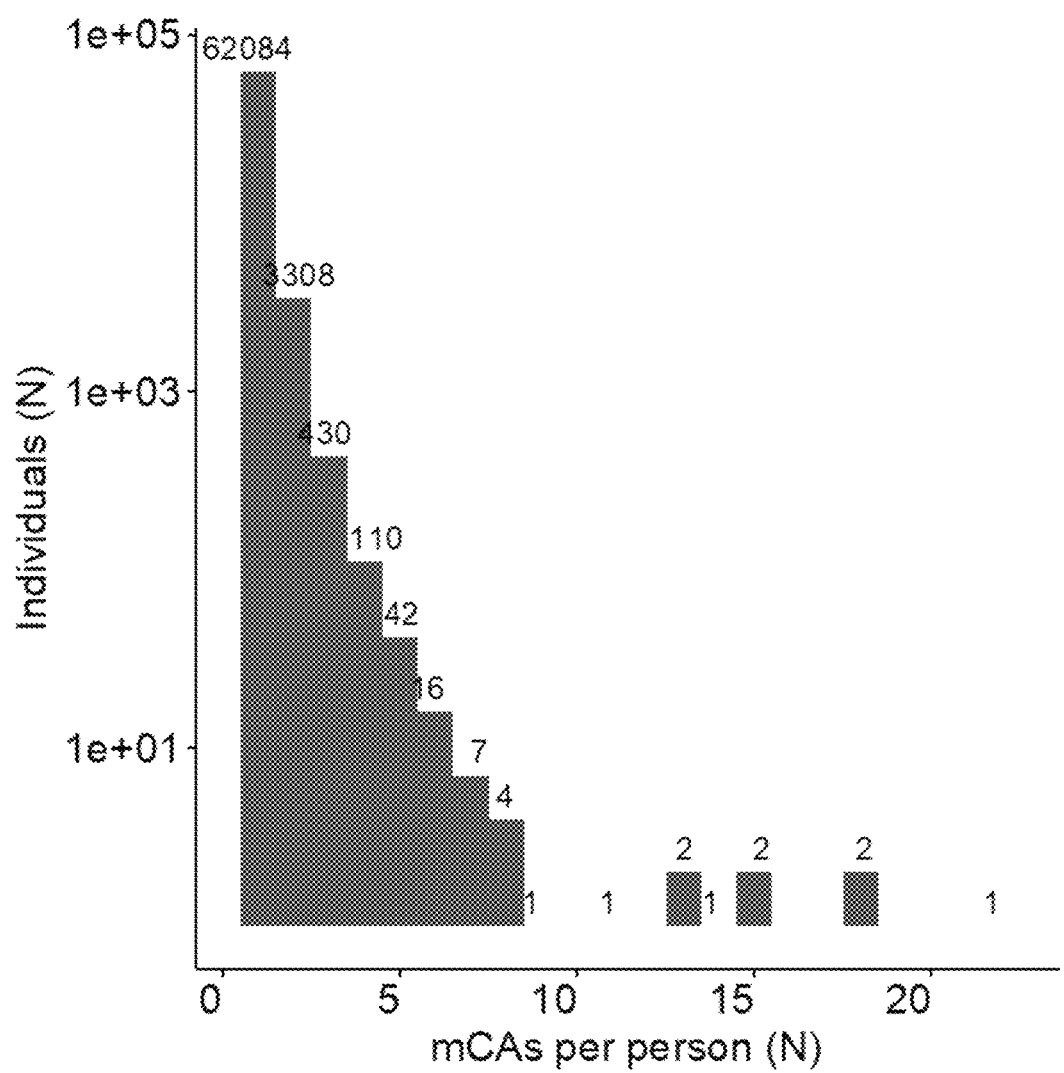
FIGS. 7A and 7B are histograms showing total number of mosaic chromosomal alterations (mCAs) (FIG. 7A) and expanded mosaic chromosomal alterations (mCAs) (FIG. 7B) per individual in the United Kingdom (UK) Biobank for mosaic chromosomal alteration (mCA) carriers.
Figure 7B:
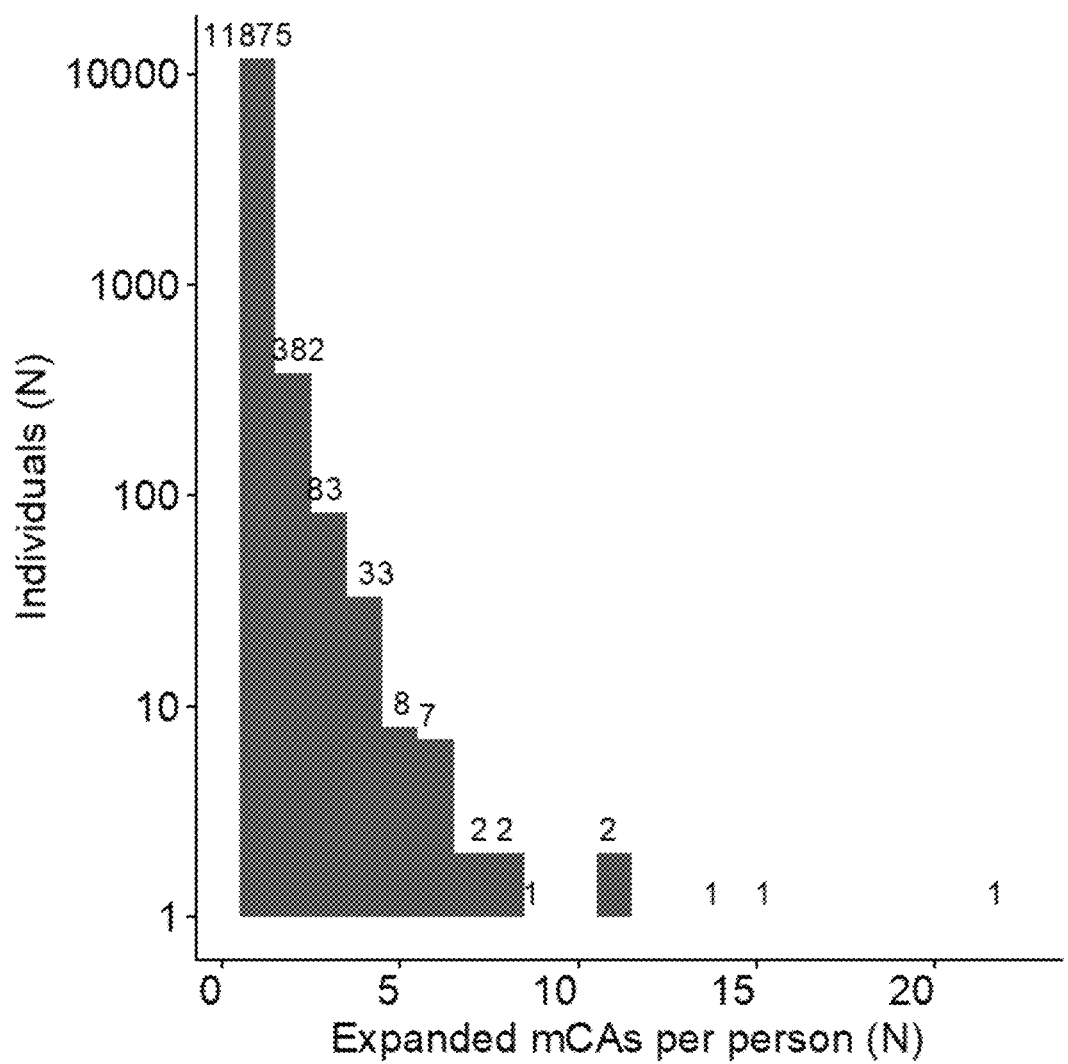
Figure 8A:
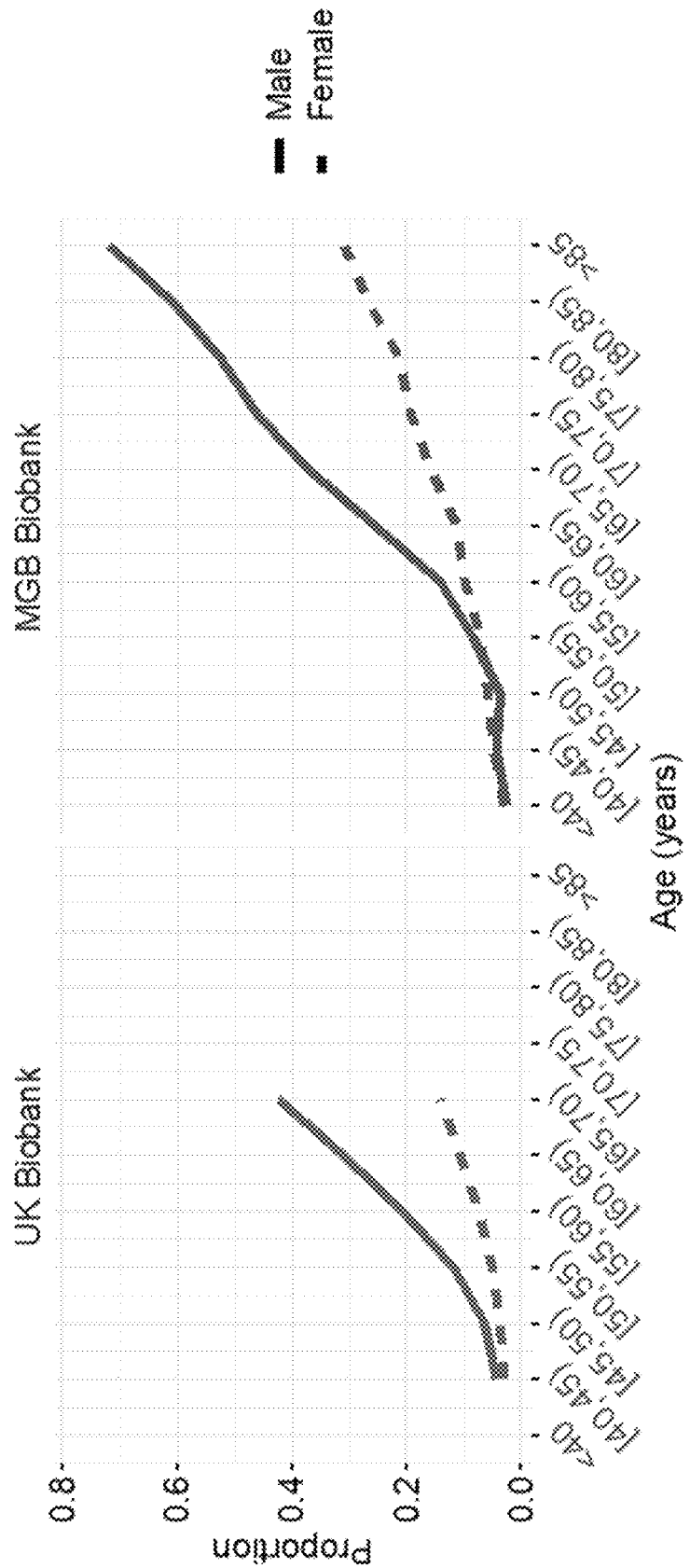
FIGS. 8A-8D are plots of prevalence of mosaic chromosomal alteration (mCA) categories by age bin in the UK Biobank and Mass General Brigham (MGB) Biobank. Prevalence of all mosaic chromosomal alterations (mCAs) is plotted in FIG. 8A. Prevalence of autosomal mosaic chromosomal alterations (mCAs) is plotted in FIG. 8B. Prevalence of chromosome X (ChrX) mosaic chromosomal alterations (mCAs) is plotted in FIG. 8C. Prevalence of chromosome Y (ChrY) mosaic chromosomal alterations (mCAs) is plotted in FIG. 8D. Throughout the figures, ChrY indicates "chromosome Y" and ChrX indicates "chromosome X".
Figure 8B:
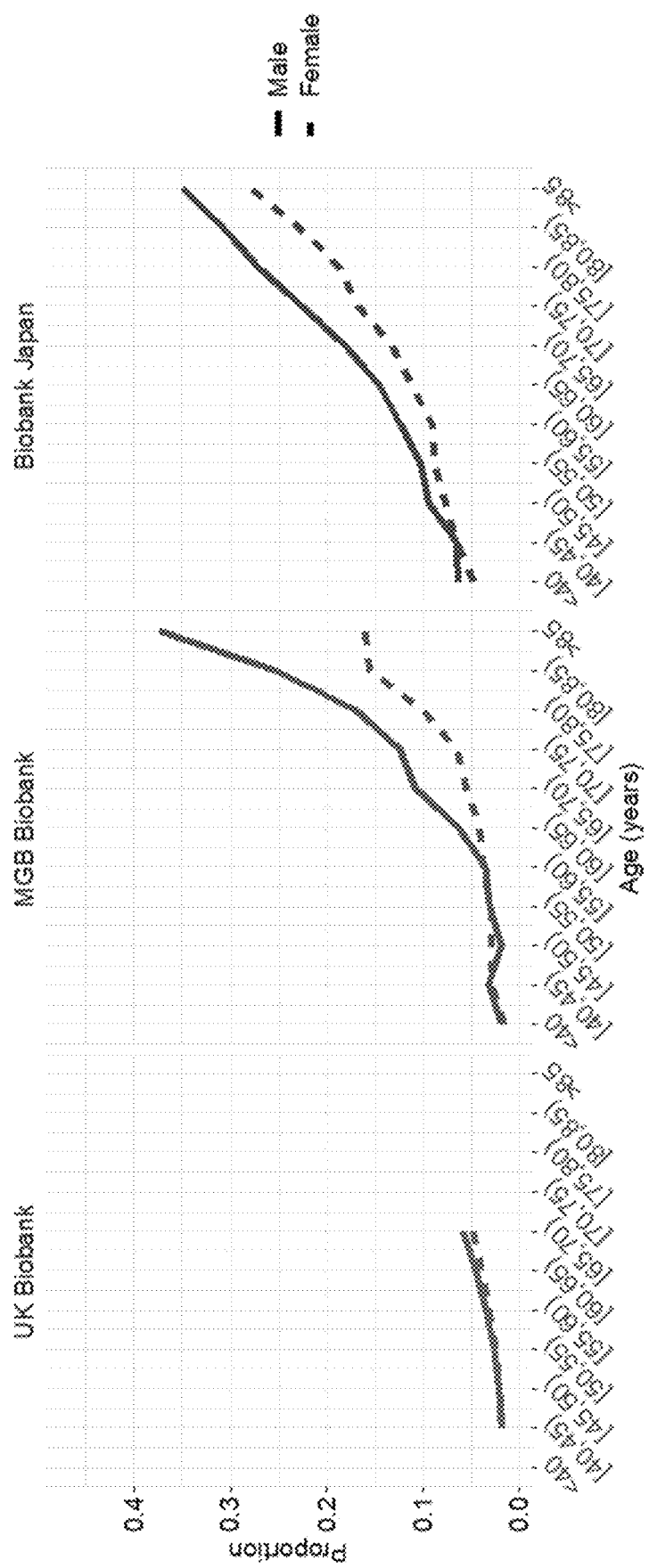
Figure 8C:
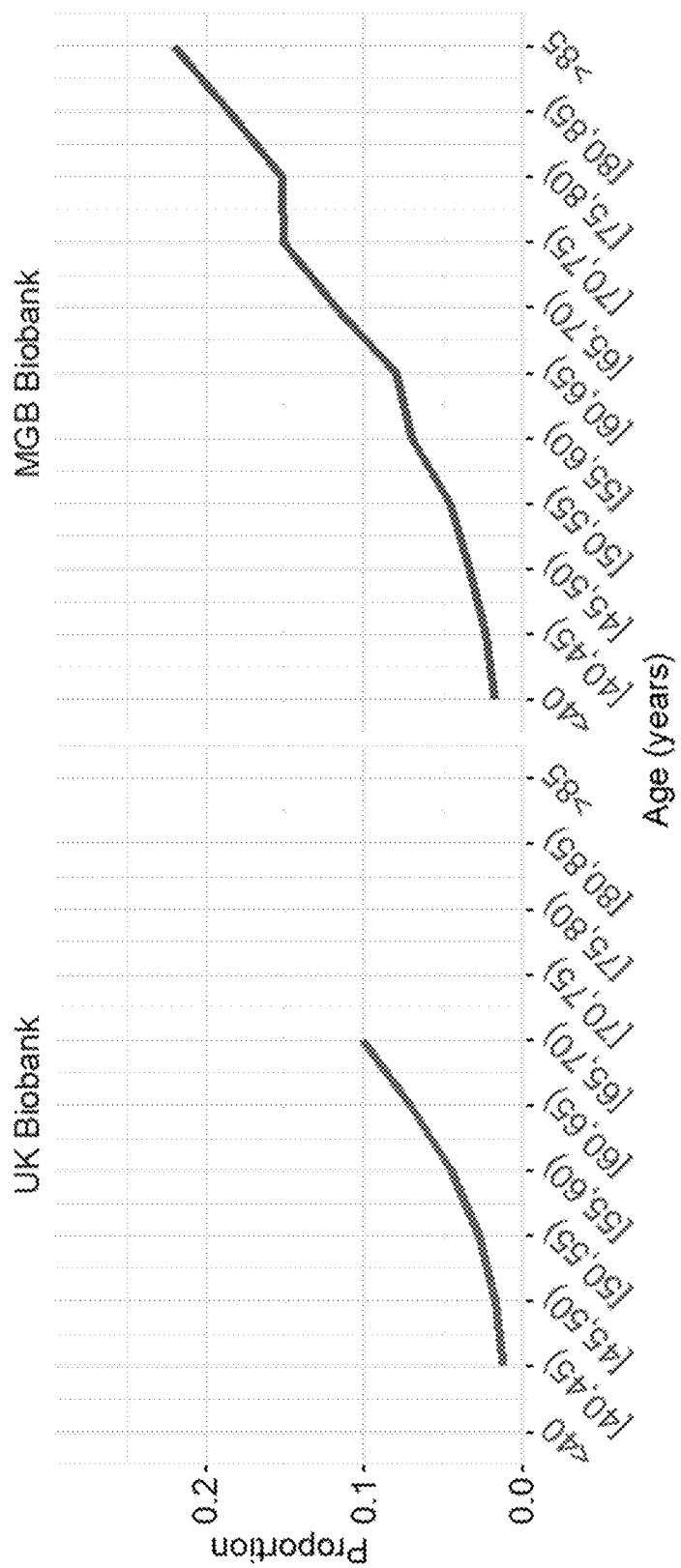
Figure 8D:
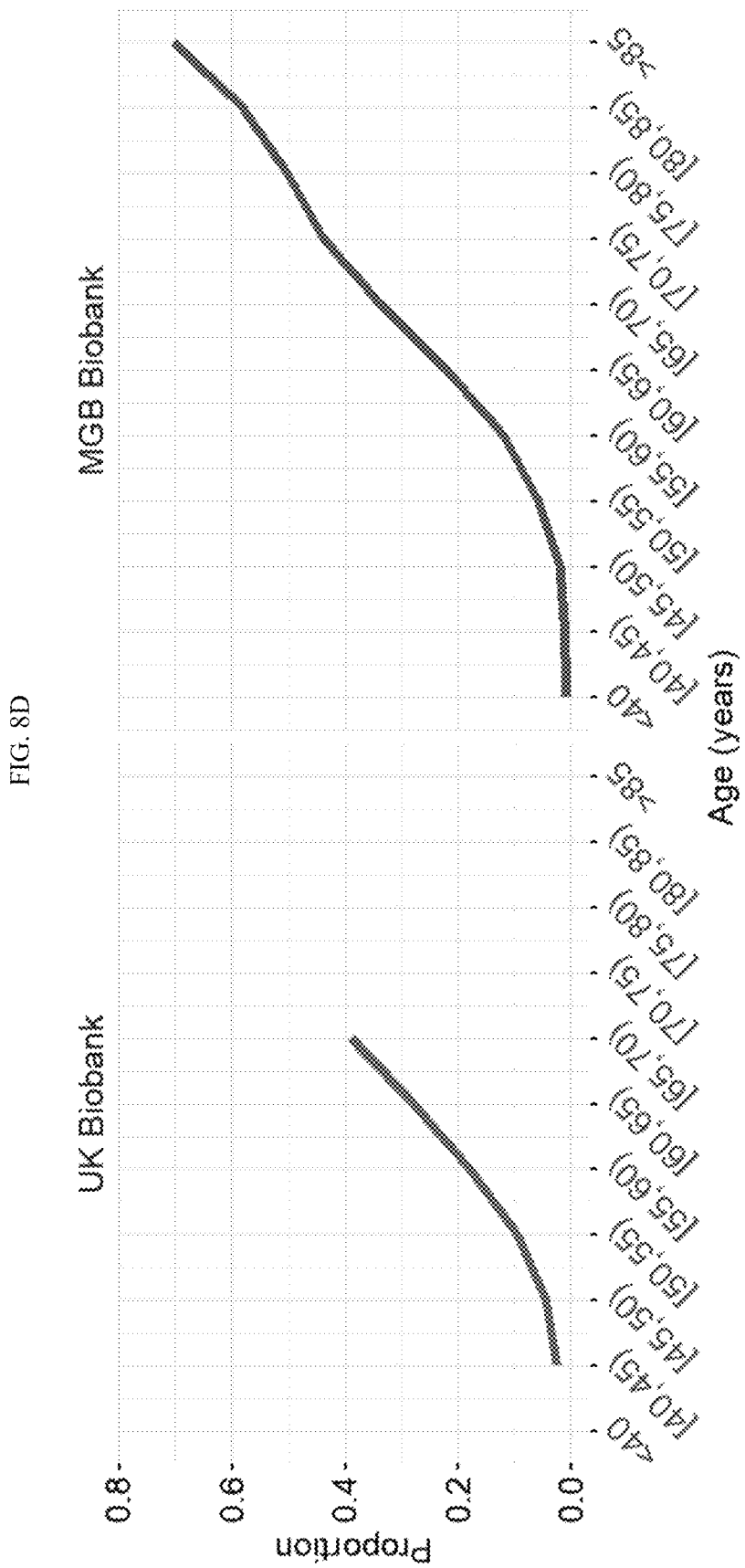
Figure 9A:
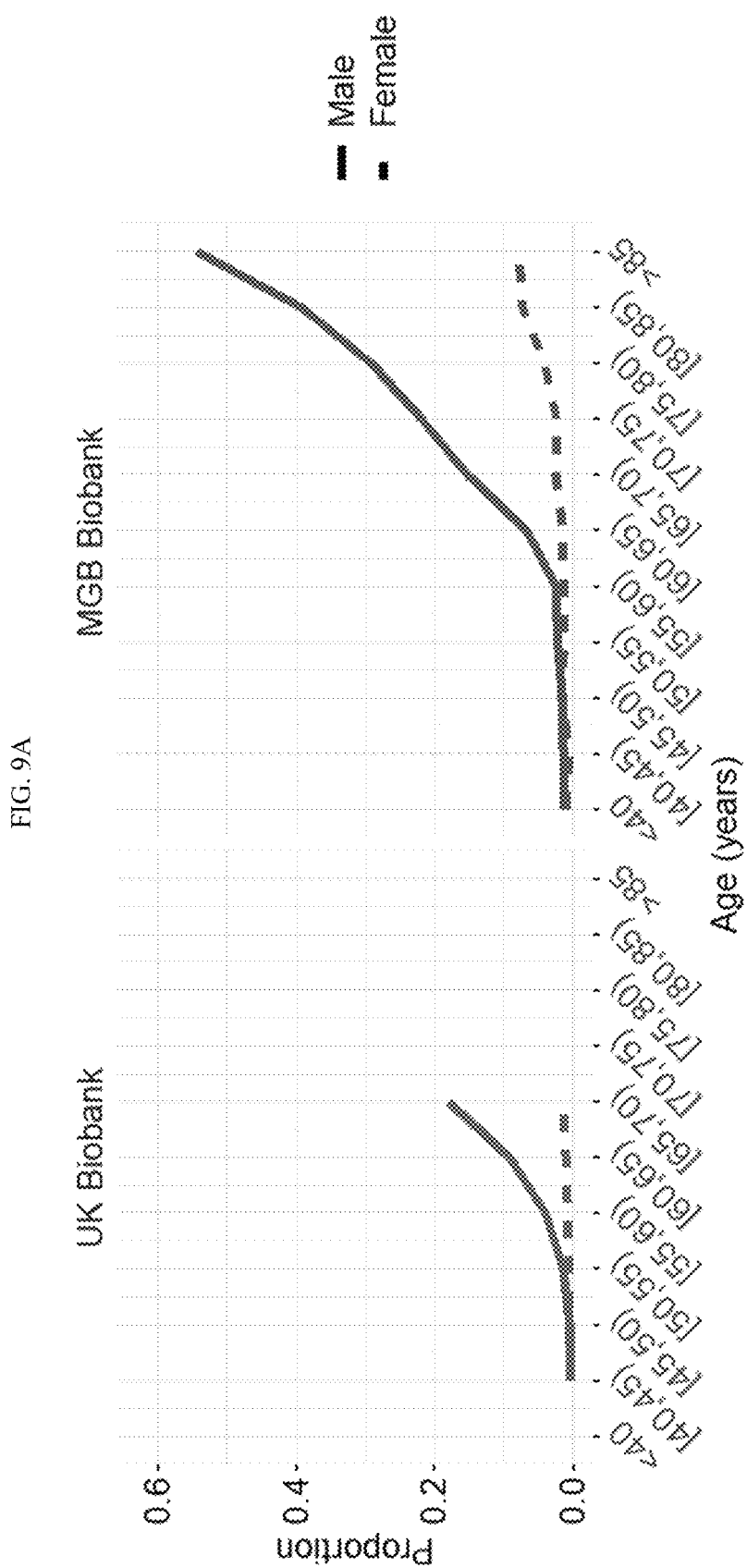
FIGS. 9A-9D are plots of prevalence of expanded mosaic chromosomal alteration (mCA) categories by age bin in the UK Biobank and Mass General Brigham (MGB) Biobank. Prevalence of all any expanded mosaic chromosomal alteration (mCA) is plotted in FIG. 9A. Prevalence expanded autosomal mosaic chromosomal alteration (mCA) is plotted in FIG. 9B. Prevalence of expanded chromosome X (ChrX) mosaic chromosomal alterations (mCAs) is plotted in FIG. 9C. Prevalence of expanded chromosome Y (ChrY) mosaic chromosomal alterations (mCAs) is plotted in FIG. 9D.
Figure 9B:
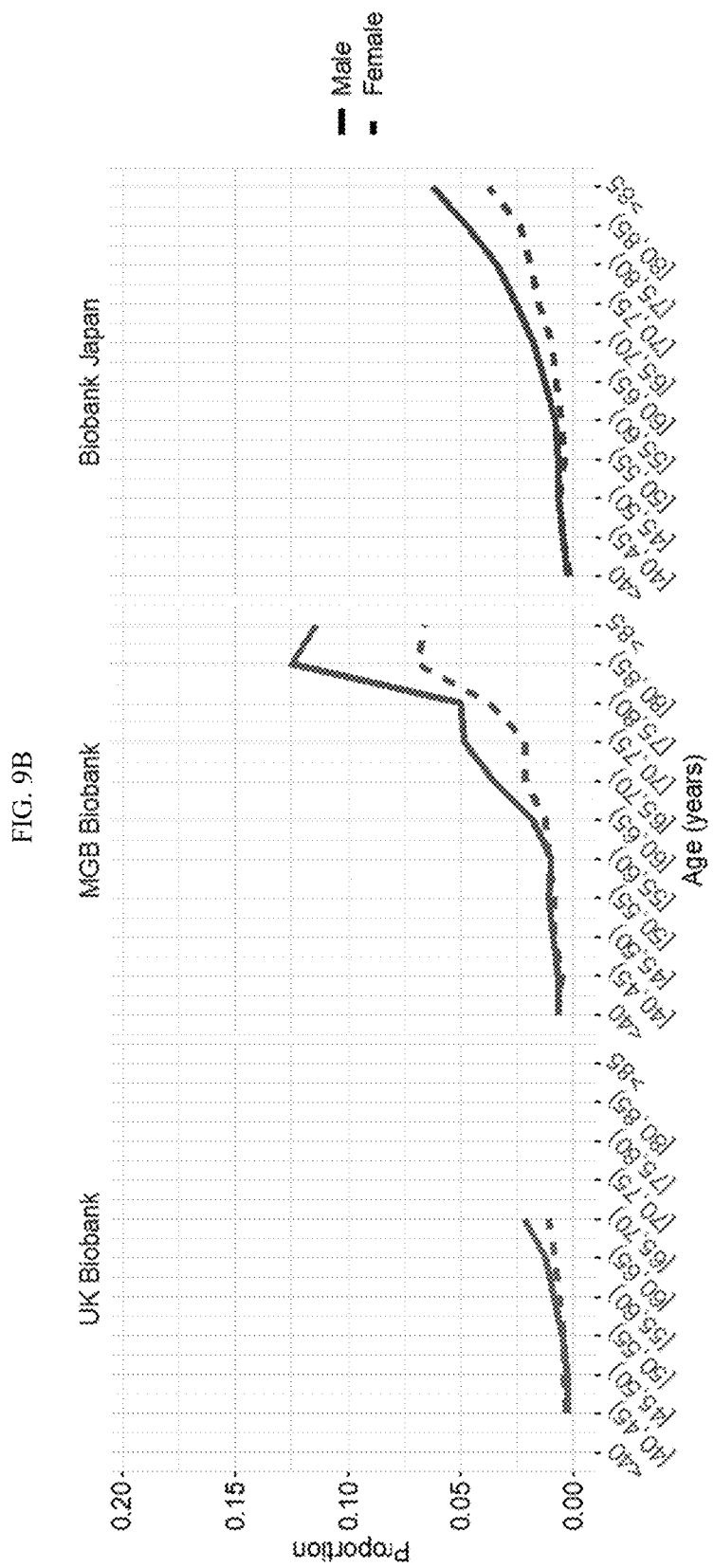
Figure 9C:
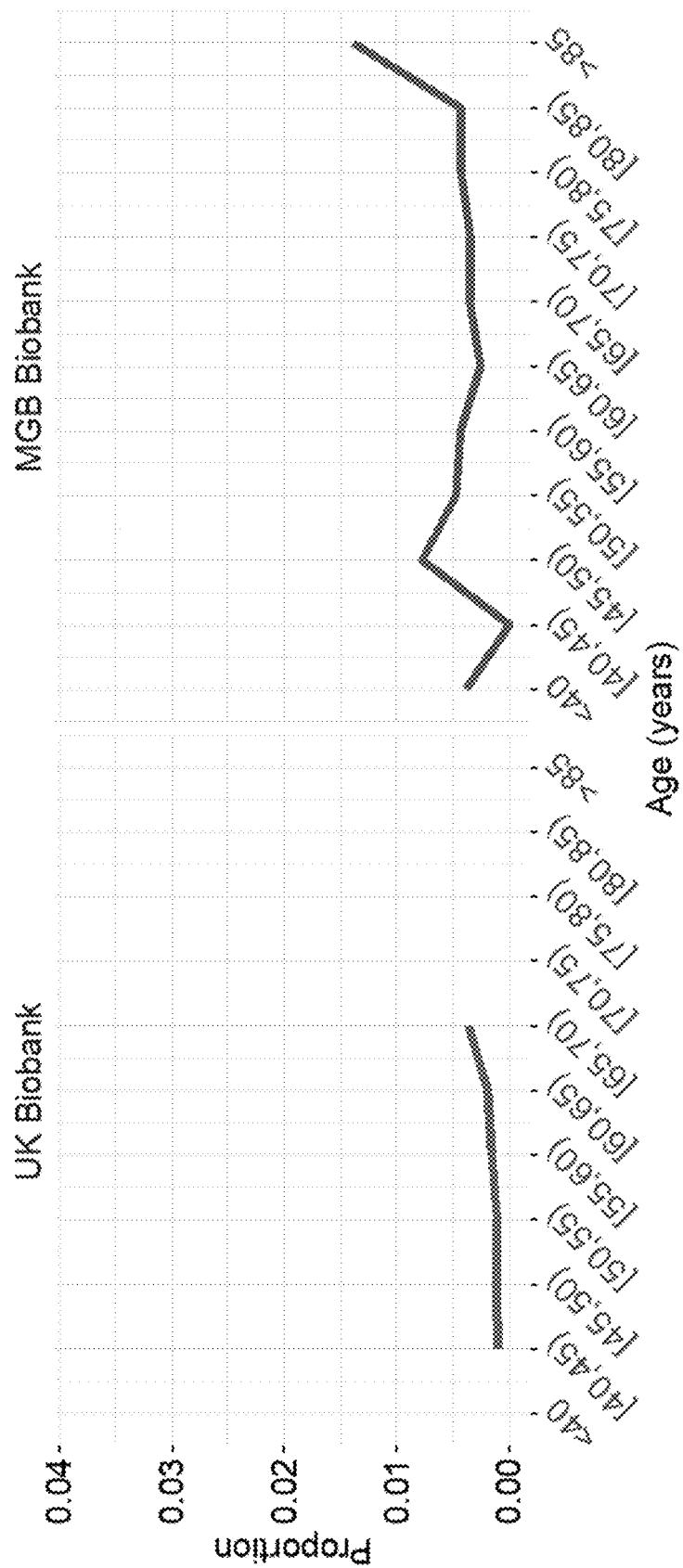
Figure 9D:
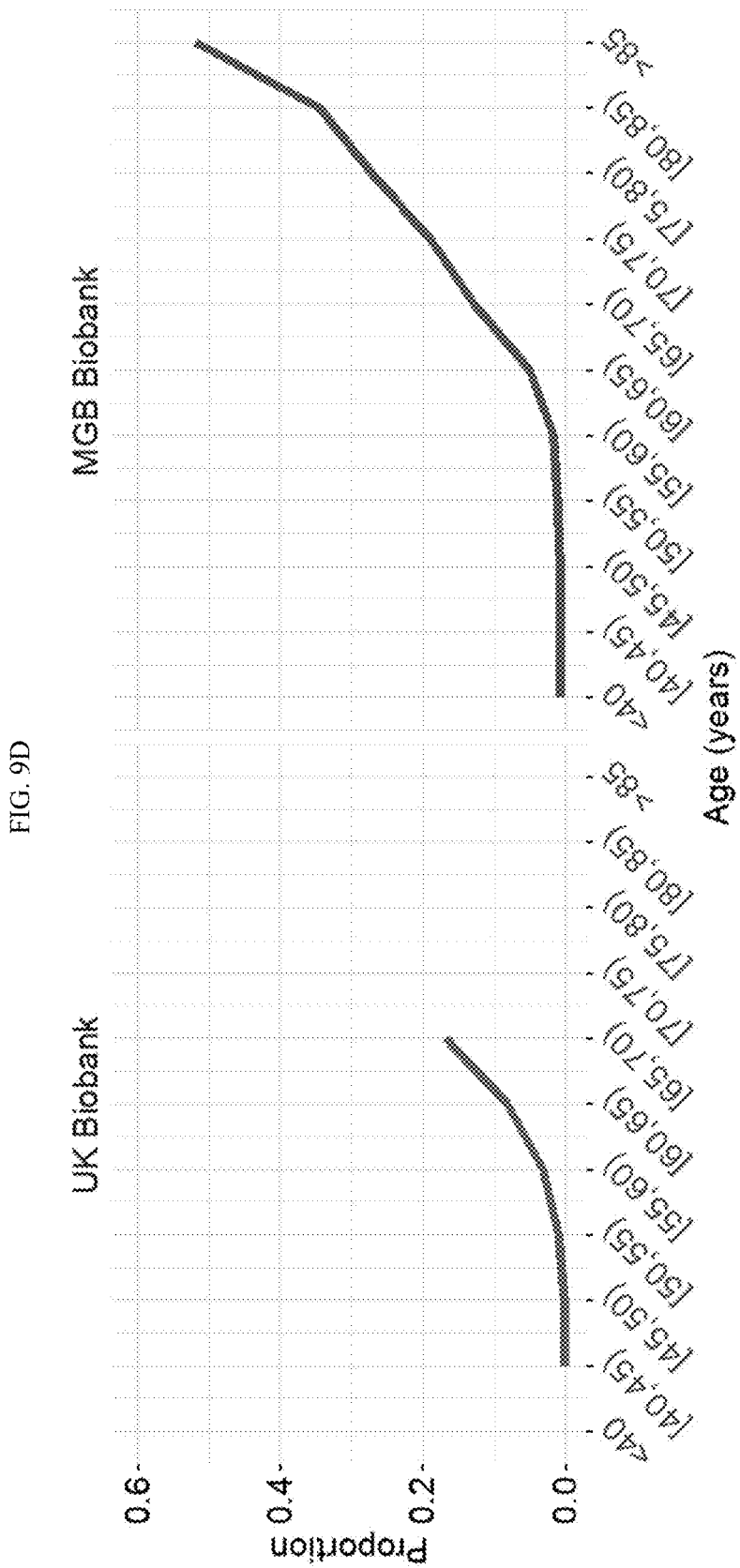

The frequency of expanded mosaic chromosomal alterations (mCAs) increased with age and was higher among men (FIGS. 8A-8D, and 9A-9D, and Table 3). The frequency of expanded autosomal mosaic chromosomal alterations (mCAs) across the United Kingdom Biobank (UKB), Mass General Brigham Biobank (MGBB), and Biobank Japan In the United Kingdom Biobank (UKB), among 444,199 unrelated individuals without a known history of hematologic malignancy, 66,011 (14.9%) carried a putative mosaic chromosomal alteration (mCA) (15,350 autosomal) and 12,398 (3.2%) carried an expanded mosaic chromosomal alteration (mCA) clone, defined as a mosaic chromosomal alteration (mCA) mutation present in at least 10% of peripheral leukocytes (2,985 autosomal) (FIGS. 7A and 7B). In the Mass General Brigham Biobank (MGBB), across 22,461 unrelated individuals without a history of hematologic cancer at date of DNA collection, 3,784 (16.8%) carried a mosaic chromosomal alteration (mCA) (1,025 autosomal) and 1,026 (5.2%) carried an expanded mosaic chromosomal alteration (mCA) clone (337 autosomal). In Biobank Japan (BBJ), across 125,541 individuals without a history of hematologic cancer, only autosomal mosaic chromosomal alterations (mCAs) were available, with 20,440 carriers (16.3%) and 1,676 (1.3%) that carried an expanded clone. (Table 2).

(BBJ) cohorts combined was 0.47% among individuals <40 years, 0.51% among 40-60 years, 1.4% among 60-80 years, and 4.3% among those greater than 80 years (FIG. 1).

TABLE 3

Association of potential risk factors with expanded autosomal mosaic chromosomal alterations (mCAs) in the United Kingdom (UK) Biobank.

|  | OR | Lower 95% CI | Upper 95% CI | P |
| --- | --- | --- | --- | --- |
| age | 0.92 | 0.86 | 1.005 | 0.068 |
| age$^2$ | 1.0013 | 1.0006 | 1.002 | 2.84E−05 |
| Sex (Male) | 1.44 | 1.33 | 1.56 | 1.33E−19 |
| Prior or current smoking | 1.09 | 1.01 | 1.18 | 0.03 |
| Prevalent Solid Cancer | 0.95 | 0.82 | 1.09 | 0.44 |
| Prevalent Type 2 Diabetes | 1.05 | 0.84 | 1.32 | 0.66 |

Figure 10:
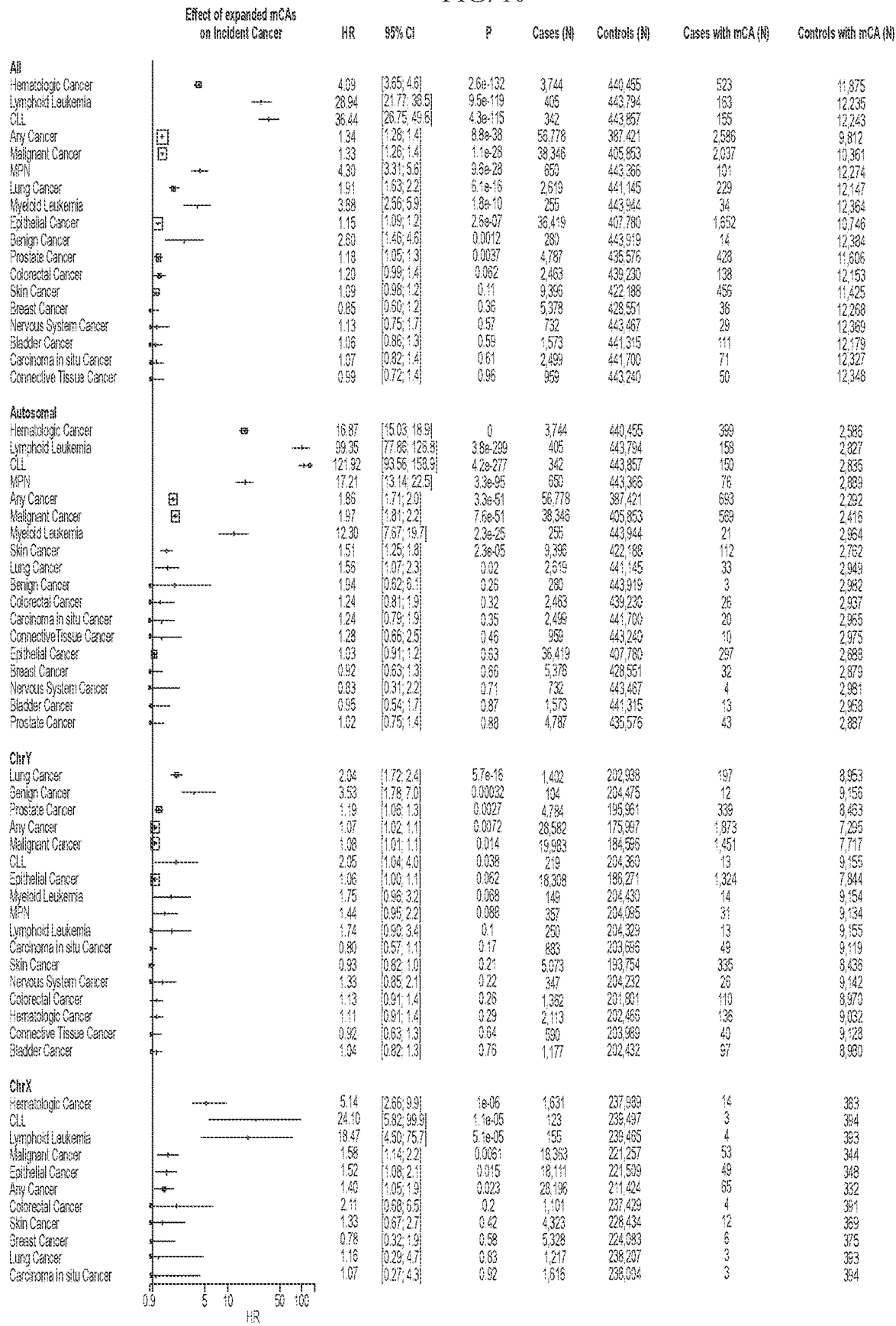
FIG. 10 is a forest plot with accompanying statistical information presenting an analysis of an association of expanded mosaic chromosomal alteration (mCA) categories with incident cancer in the UK Biobank. Analyses are adjusted for age, age$^2$, sex, smoking status, and principal components of ancestry. Individuals with a history of hematologic cancer at enrollment were removed from analysis. CLL=chronic lymphocytic leukemia, MPN=myeloproliferative neoplasms.
Figure 11:
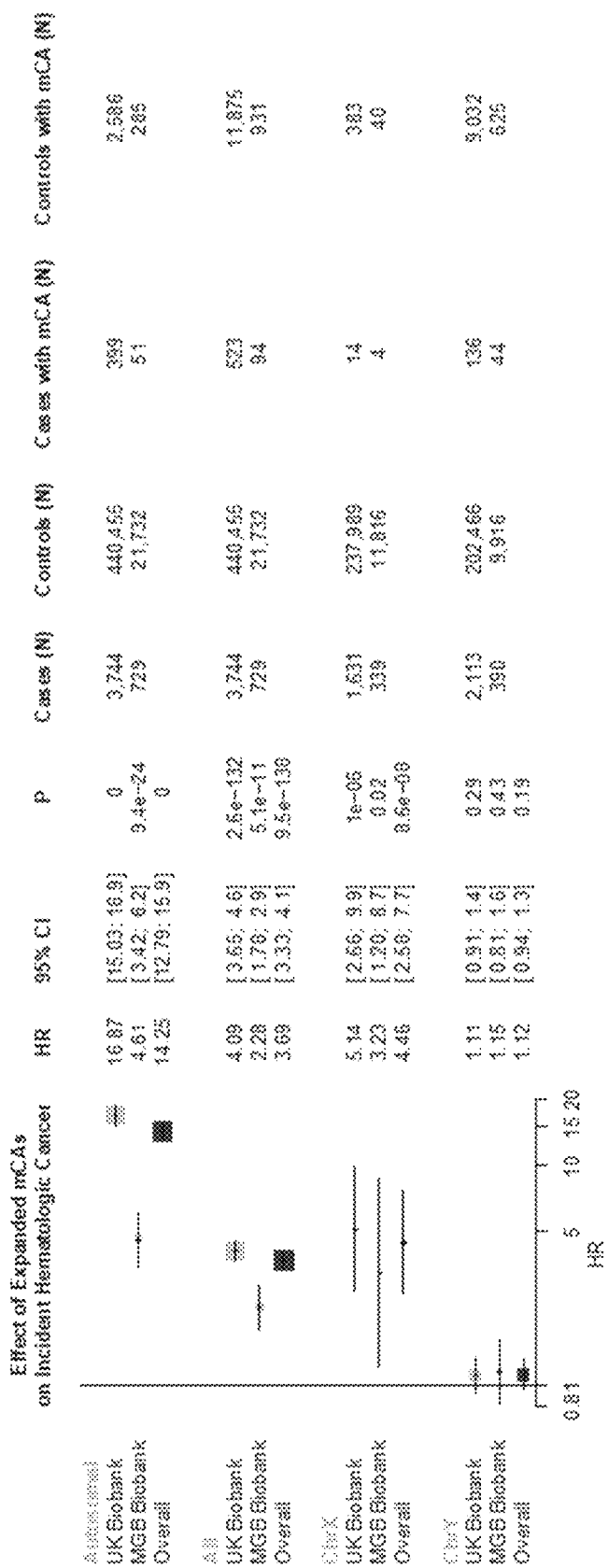
FIG. 11 is a forest plot with accompanying statistical information presenting an analysis of an association of expanded mosaic chromosomal alteration (mCA) categories with incident hematological cancer in the UK Biobank and Mass General Brigham (MGB) Biobank. Analyses are adjusted for age, age$^2$, sex, smoking status, and principal components of ancestry. Individuals with a history of hematologic cancer at enrollment were removed from analysis.

Example 2: Association of Mosaic Chromosomal Alterations (mCAs) with Hematologic Traits In the United Kingdom Biobank (UKB), expanded mosaic chromosomal alterations (mCAs) were most strongly associated with incident hematologic cancer, with the strongest association being for incident chronic lymphoid leukemia (HR 121.9; 95% CI 93.6 to 158.9; P=4.2×$10^{-277}$); although an association with myeloid leukemia was also present (HR 12.3; 95% CI 7.7 to 19.7; P=2.3×$10^{-25}$) (FIG. 10). The association of expanded mosaic chromosomal alterations (mCAs) with incident hematologic cancer was replicated in the Mass General Brigham Biobank (MGBB) (FIG. 11).

Figure 12:
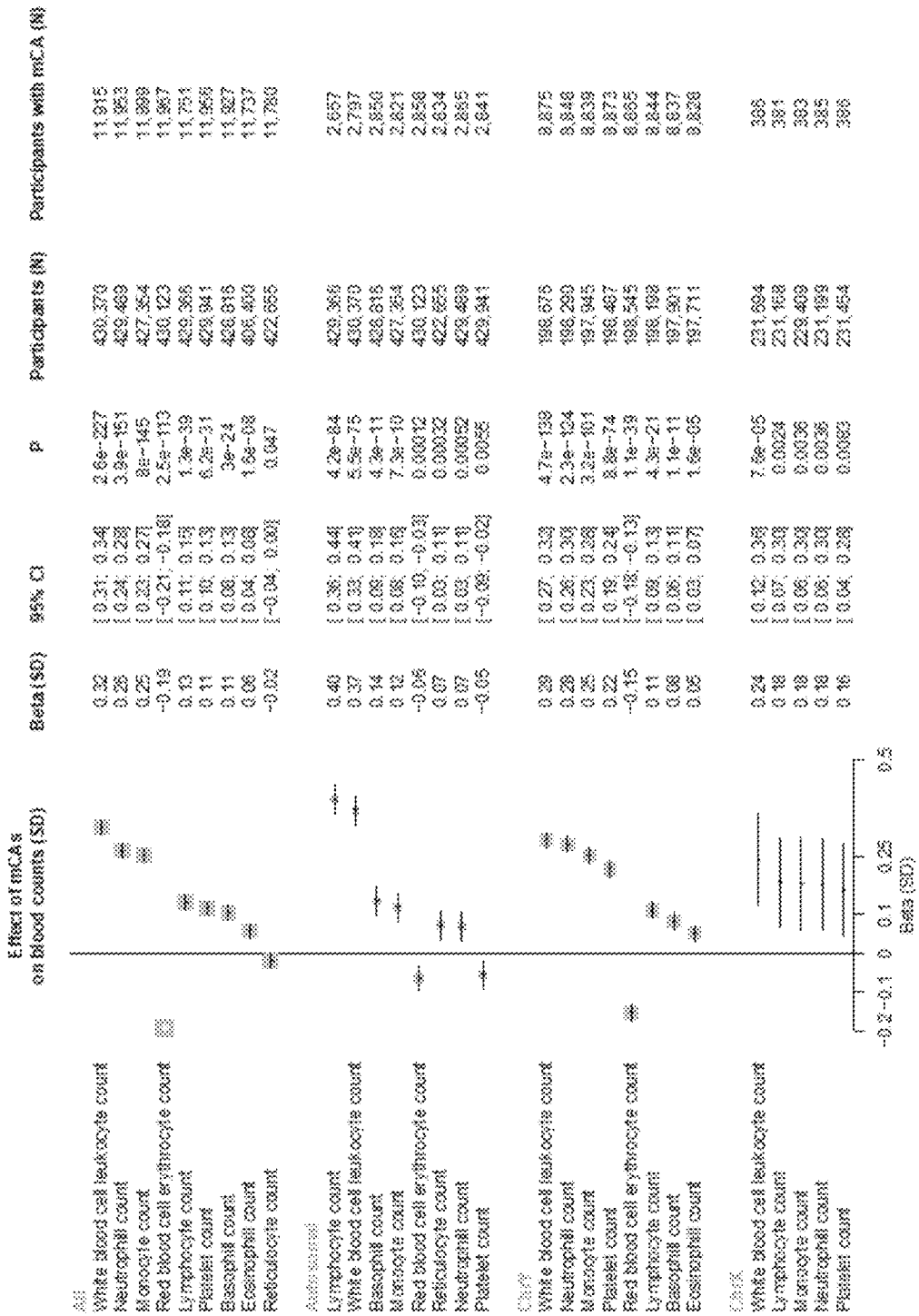
FIG. 12 is a forest plot with accompanying statistical information presenting an analysis of an association of blood counts with expanded mosaic chromosomal alterations (mCAs). Associations are adjusted for age, age$^2$, sex, smoking status, and principal components of ancestry. Throughout the figures, SD indicates "standard deviation".
Figure 13B:
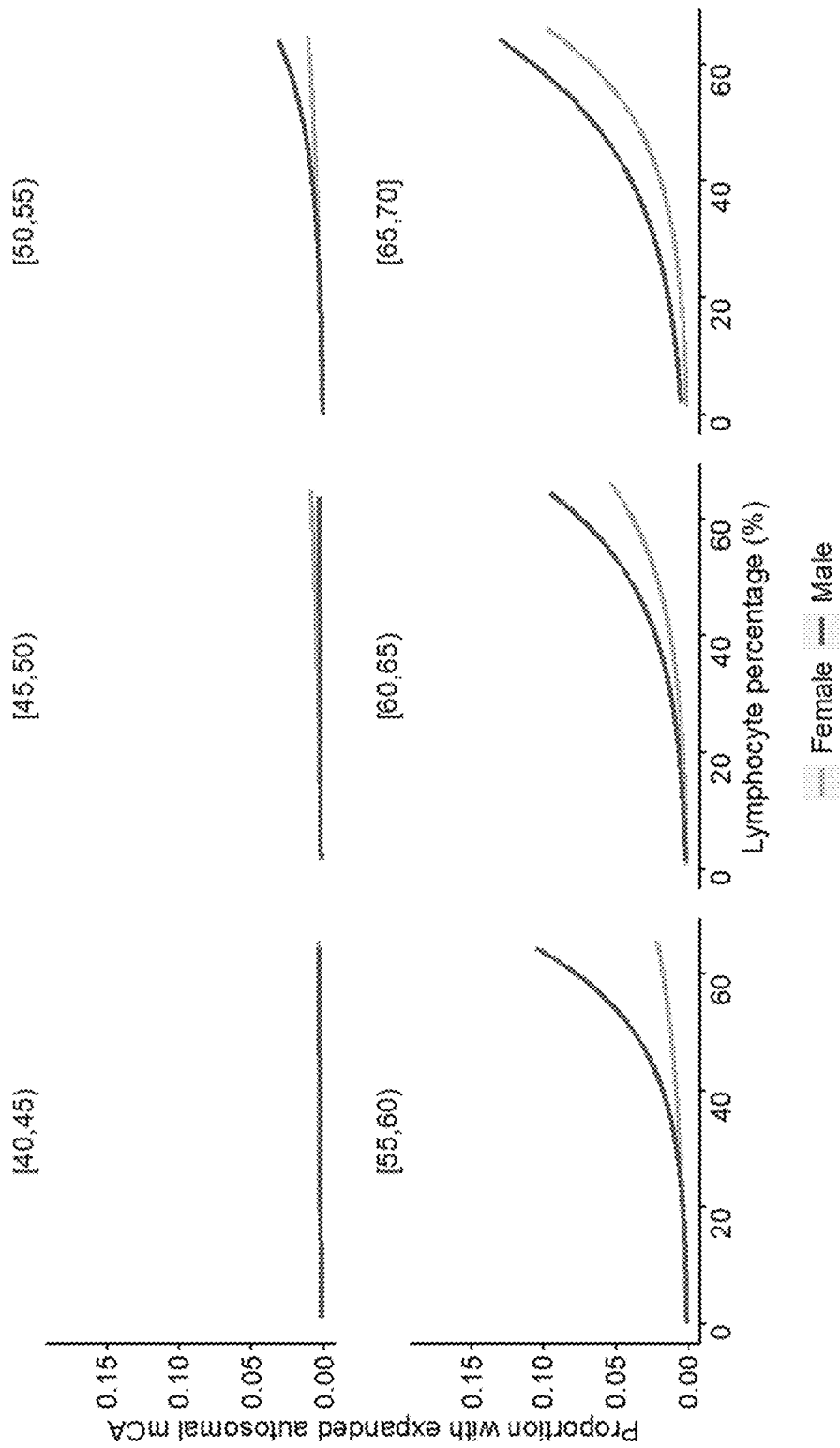

Additionally, in the United Kingdom Biobank (UKB), associations of expanded mosaic chromosomal alterations (mCAs) with blood cell traits were observed, with the strongest observed between expanded autosomal mosaic chromosomal alterations (mCAs) and increased lymphocyte count at enrollment (Beta 0.40 SD or 0.25×$10^{-9}$ cells/L; 95% CI 0.36 to 0.44 SD; P=4.2×$10^{-84}$) (FIGS. 12 and 13A-13B).

Example 3: Associations with Diverse Infections

Figure 2:
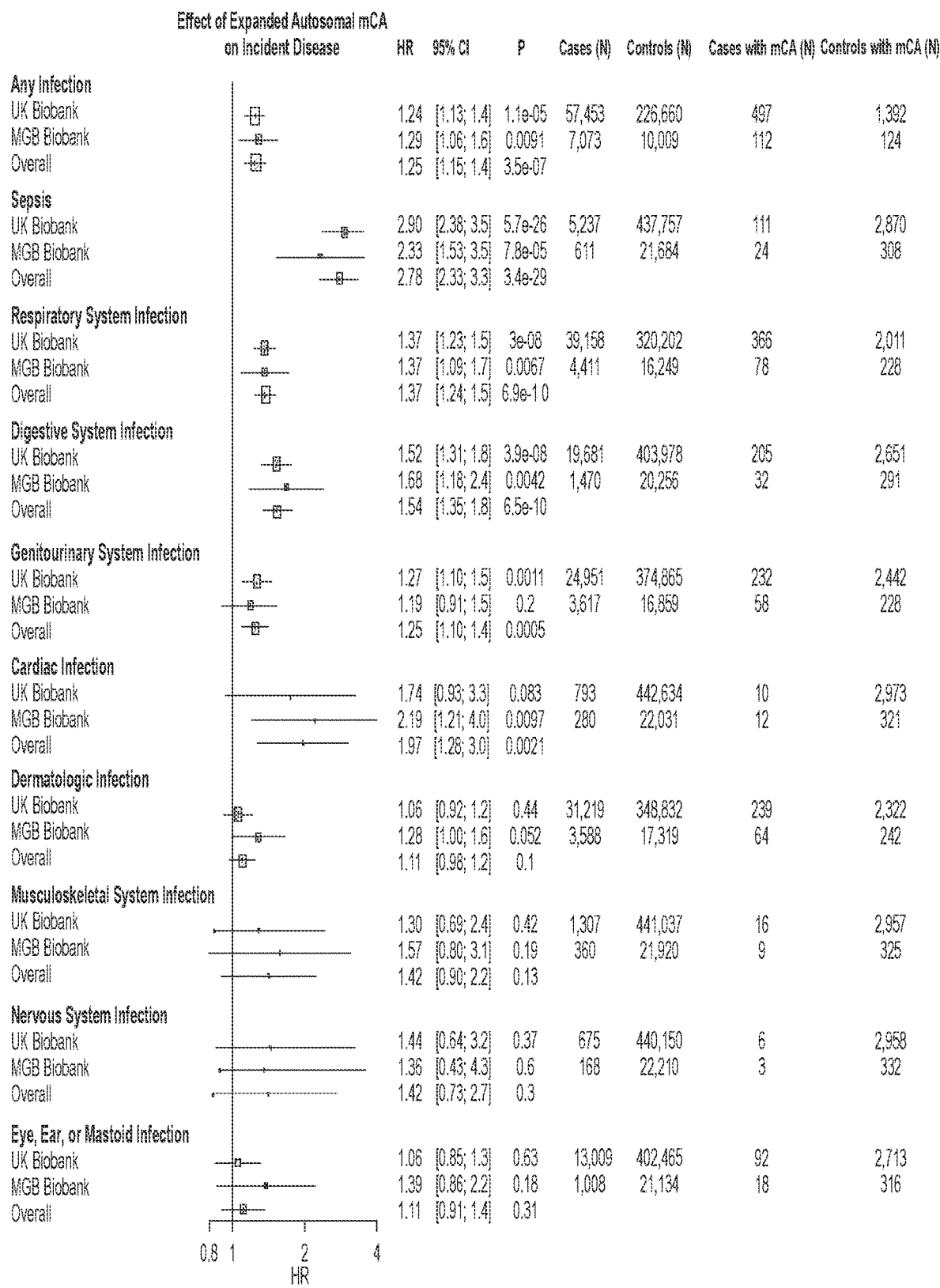
FIG. 2 is a forest plot with accompanying statistical information presenting an analysis of an association of expanded autosomal mosaic chromosomal alterations (mCAs) with incident infections across individuals in the United Kingdom Biobank (UKB) and Mass General Brigham Biobank (MGBB).
Figure 3:
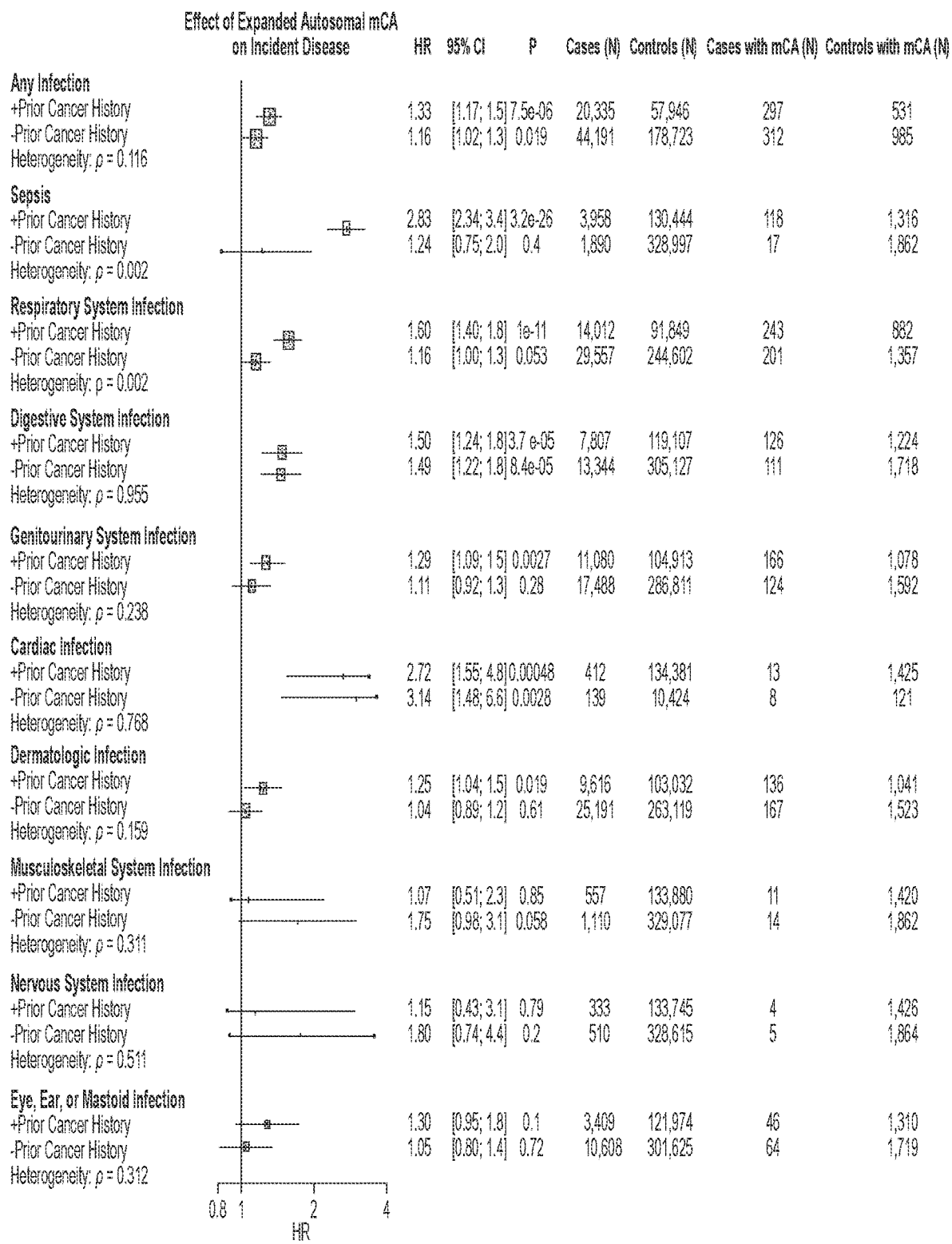
FIG. 3 is a forest plot with accompanying statistical information presenting an analysis of an association of expanded autosomal mosaic chromosomal alterations (mCAs) with incident infections across individuals with and without a cancer history before their incident infection, meta-analyzed across United Kingdom Biobank (UKB) and Mass General Brigham Biobank (MGBB) combined (cohort-specific analyses are shown in FIG. 19). Individuals with known hematologic cancer at time of or prior to blood draw for genotyping were excluded. Analyses are adjusted for age, age$^2$, sex, smoking status, and principal components of ancestry. Throughout the figures, CI represents "95% confidence interval".
Figure 14A:
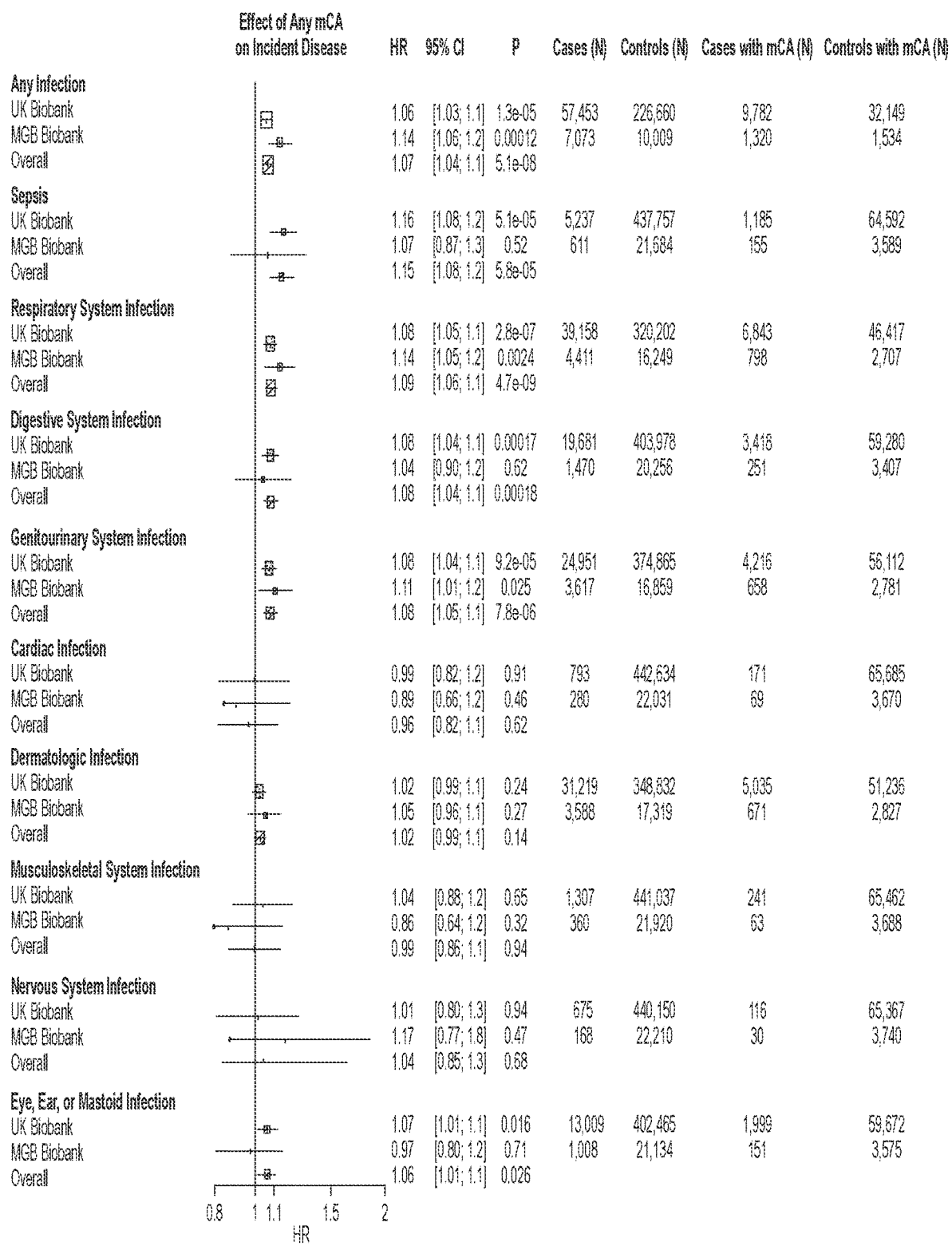
FIGS. 14A and 14B are forest plots with accompanying statistical information presenting an analysis of associations of A) any mosaic chromosomal alteration (mCA) (FIG. 14A) and B) any expanded mosaic chromosomal alteration (mCA) (FIG. 14B) with incident infections.
Figure 14B:
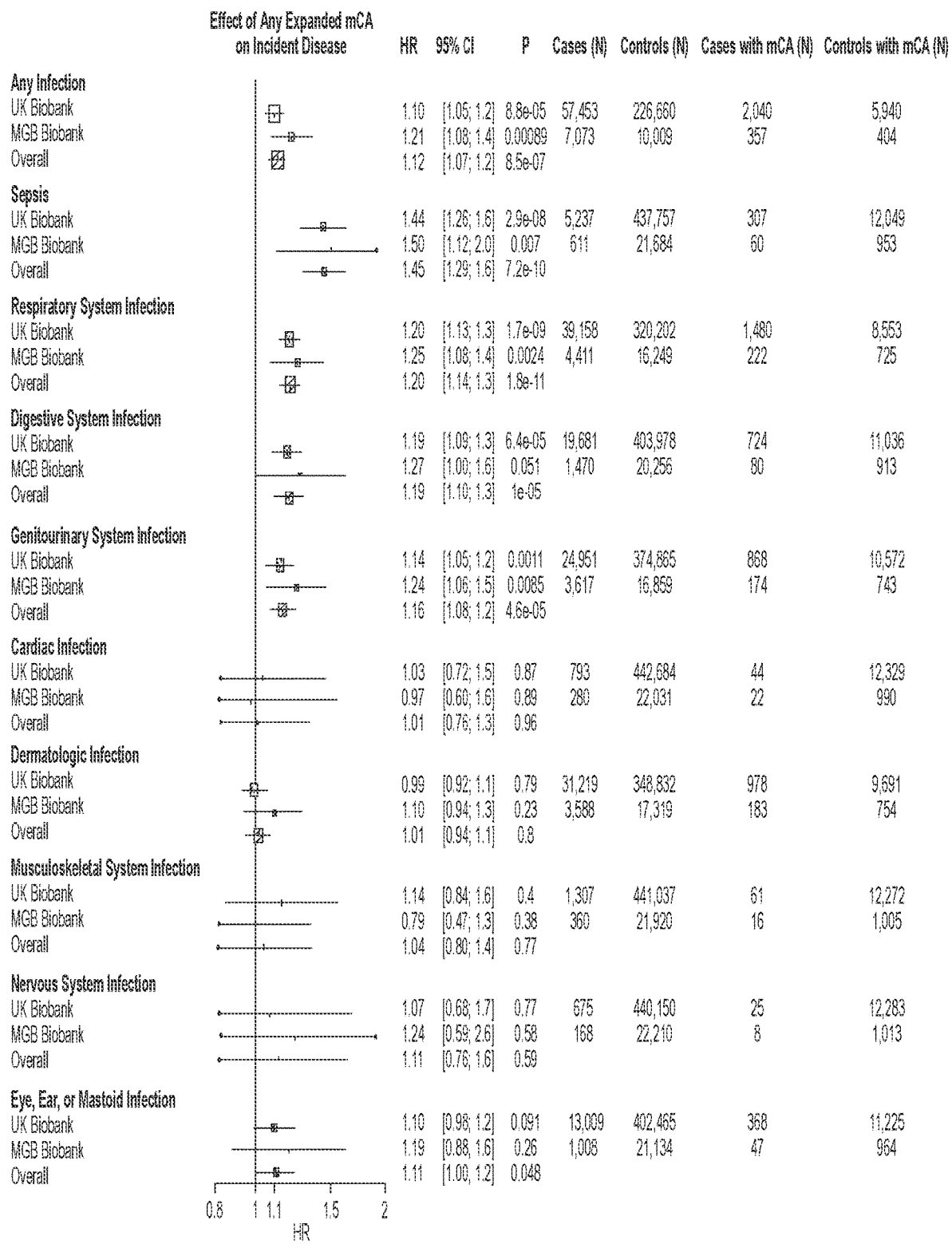
Figure 15:
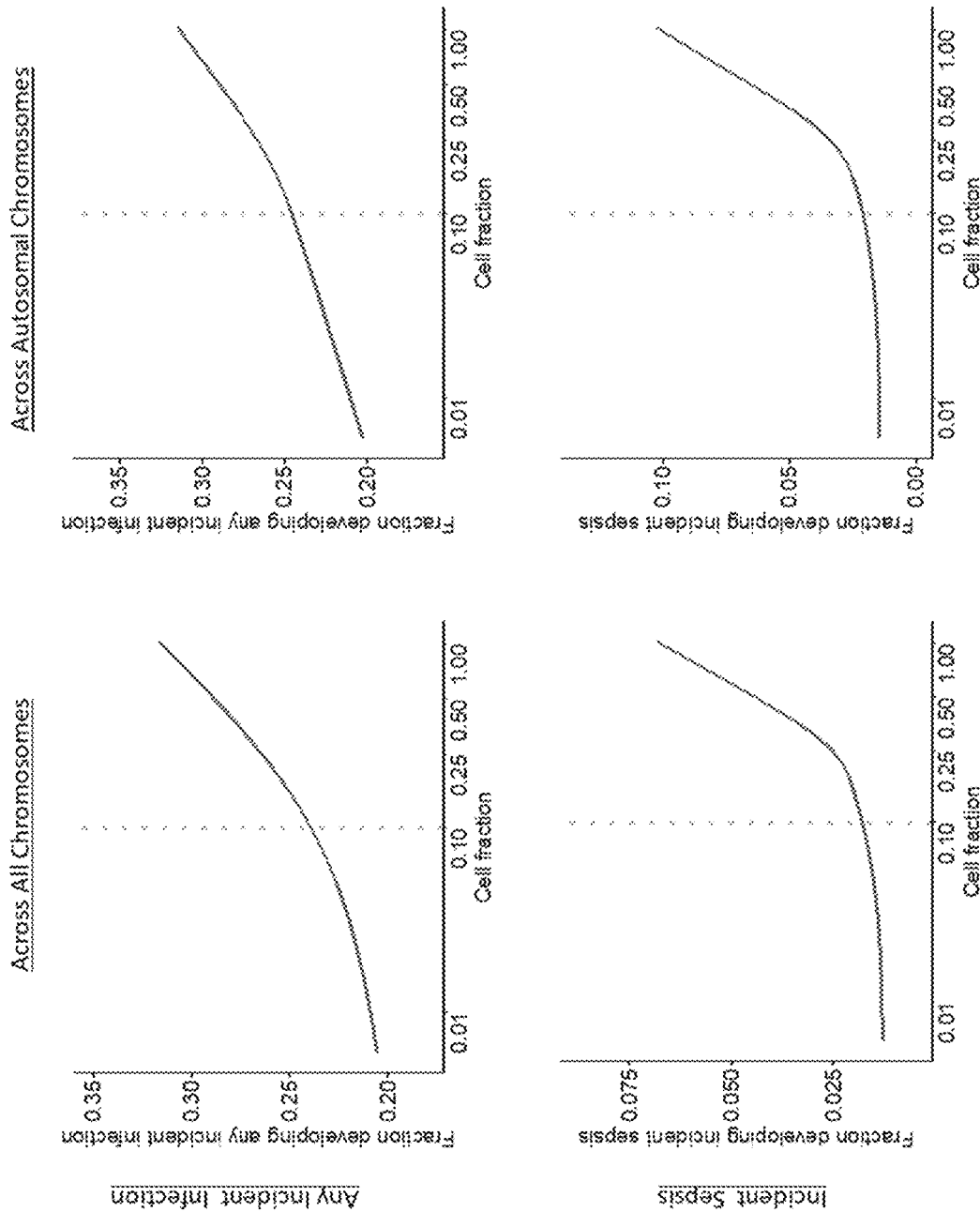
FIG. 15 is a collection of plots showing an association of incident infection and incident sepsis with cell fraction across all chromosomes and across autosomal chromosomes. The dotted line at cell fraction of 0.1 shows a cutoff for defining an expanded mCA clone.
Figure 16:
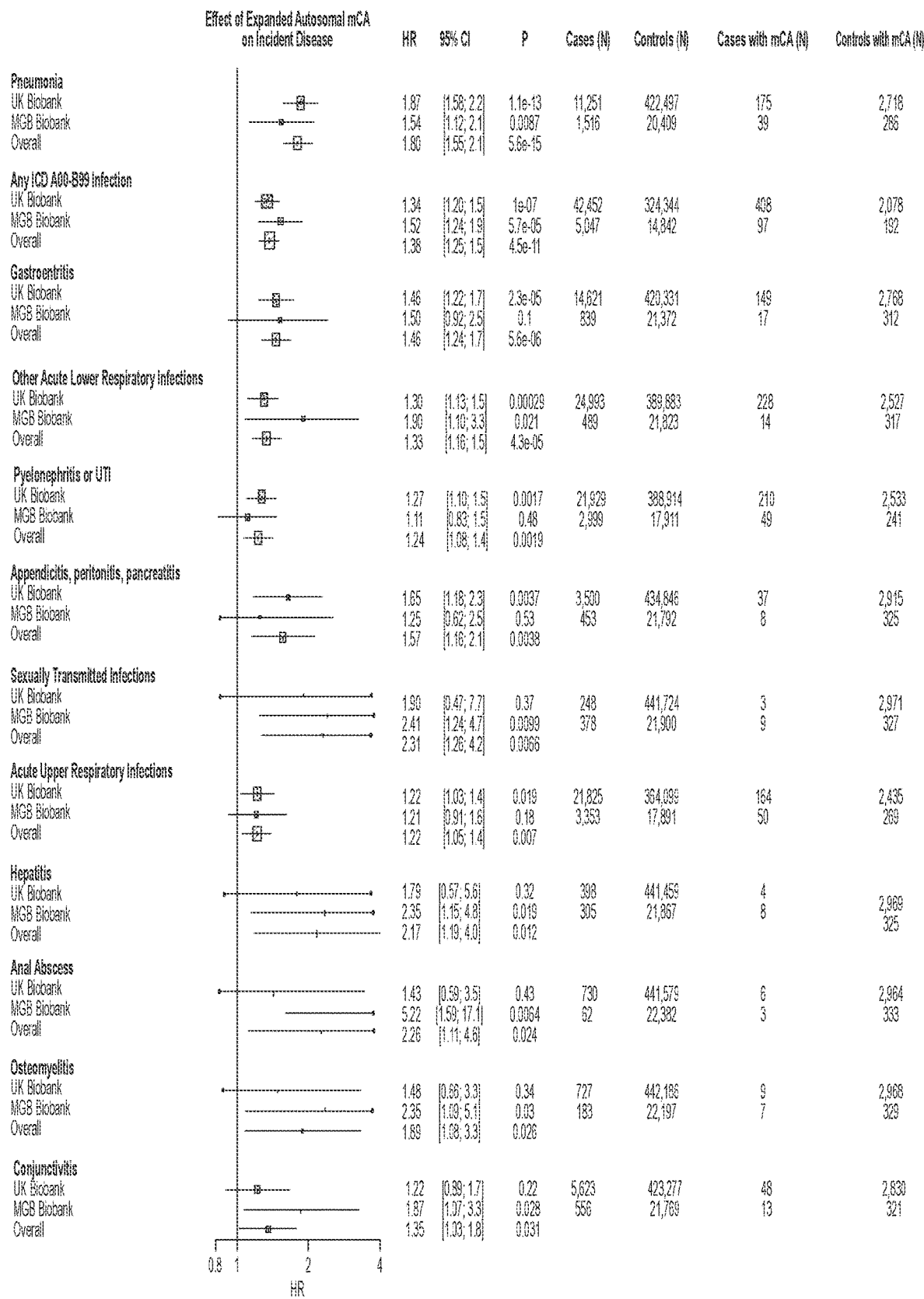
FIG. 16 is a forest plot with accompanying statistical information presenting an analysis of suggestive associations (P<0.05) of expanded autosomal mosaic chromosomal alterations (mCAs) with incident infection categories.
Figure 17A:
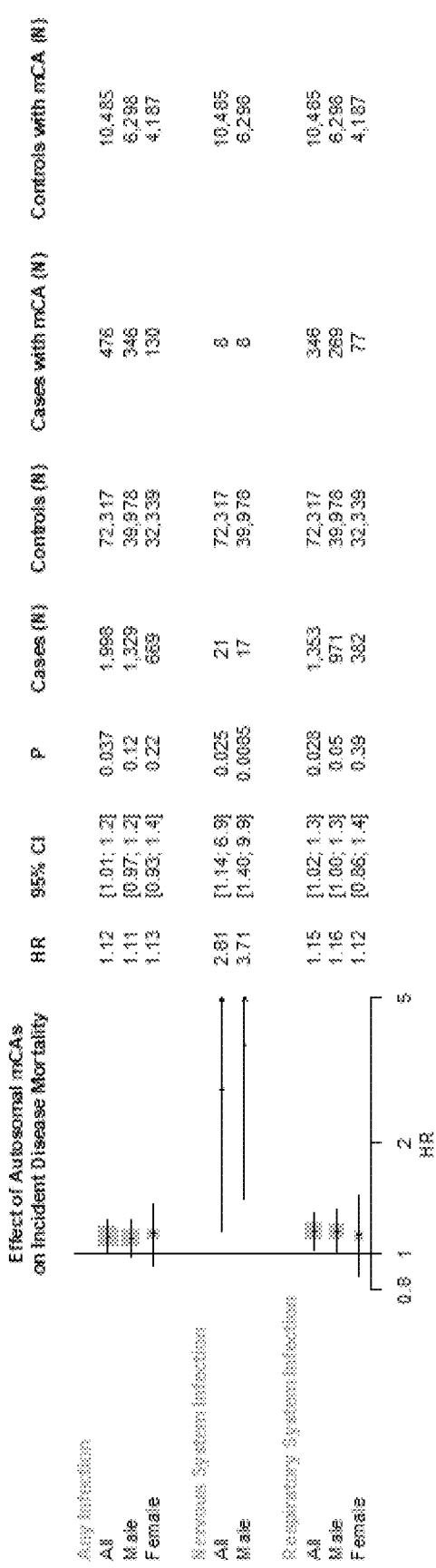
FIGS. 17A-17C are forest plots with accompanying statistical information presenting an analysis of suggestive associations (P<0.05) of mosaic chromosomal alterations (mCAs) with incident infection-related mortality in Biobank Japan. Associations of autosomal mosaic chromosomal alterations (mCAs) with A) organ-system level infections (FIG. 17A) and B) specific infection categories (FIG. 17B). C) Association of expanded autosomal mosaic chromosomal alterations (mCAs) with sepsis (FIG. 17C). Full results are in Table 1 provided in the Examples below. Associations are presented among individuals without any cancer history.
Figure 17B:
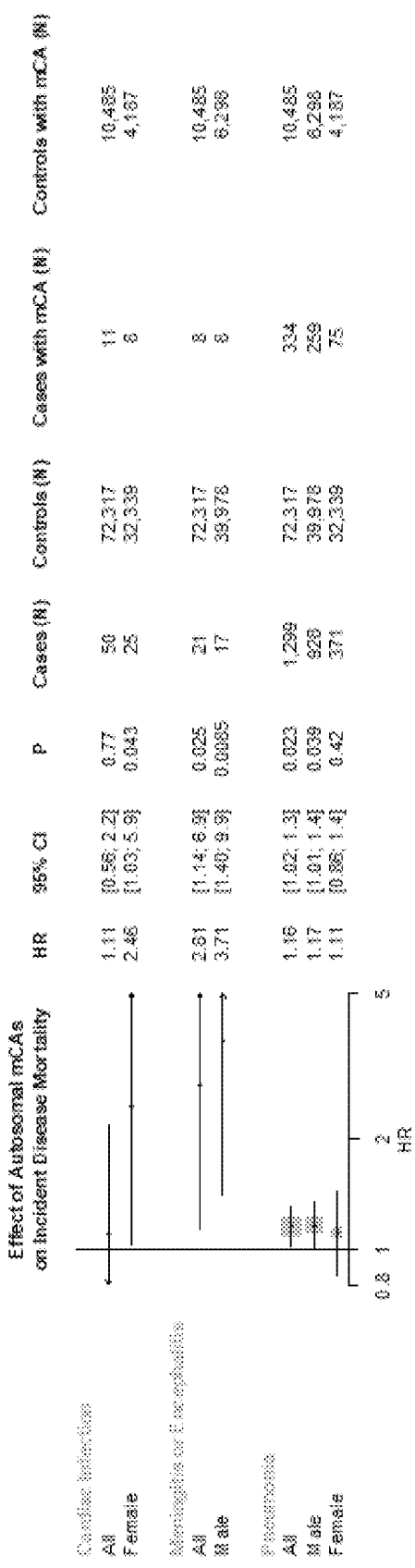
Figure 17C:
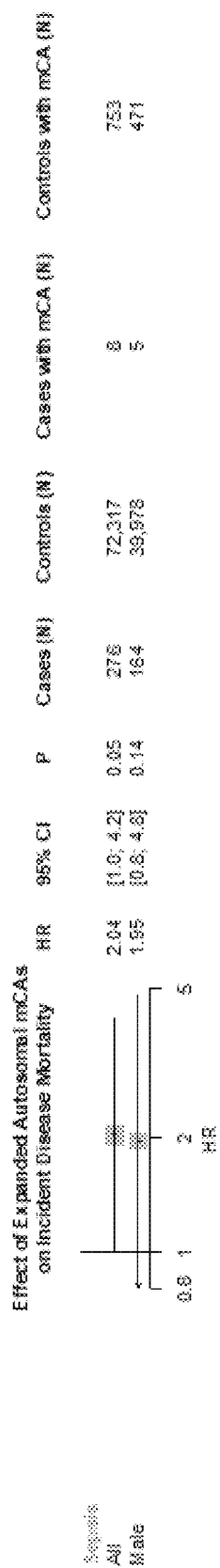

Mosaic chromosomal alterations (mCAs) were associated with diverse incident infections (HR 1.07; 95% CI 1.04 to 1.1; P=5.1×$10^{-8}$) (FIG. 14A), independent of age, age2, sex, smoking status, and first 10 principal components of ancestry in the combined United Kingdom Biobank (UKB) and Mass General Brigham Biobank (MGBB) meta-analysis. This association was stronger for expanded mosaic chromosomal alteration (mCA) clones, namely, mCAs present in over 10% of circulating leukocytes (HR 1.12; 95% CI 1.1 to 1.2; P=8.5×$10^{-7}$) (FIGS. 14B and 15), and strongest across expanded autosomal mosaic chromosomal alterations (mCAs) (HR 1.3; 95% CI 1.1 to 1.4; P=3.5×$10^{-7}$) (FIG. 2). In particular, expanded autosomal mosaic chromosomal alterations (mCAs) were associated with sepsis (HR 2.8; 95% CI 2.3 to 3.3; P=3.4×$10^{-29}$), respiratory system infections (HR 1.4; 95% CI 1.2 to 1.5; P-6.9×$10^{-10}$), digestive system infections (HR 1.5; 95% CI 1.3 to 1.8; P=6.5×$10^{-10}$), and genitourinary system infections (HR 1.3; 95% CI 1.1 to 1.4; P=5.0×$10^{-4}$) (FIG. 16). Among individuals without any cancer history in Biobank Japan (BBJ), autosomal mosaic chromosomal alterations (mCAs) showed nominal associations with fatal incident infections (any infection: HR 1.12, 95% CI 1.0 to 1.2 P=0.04; nervous system infection: HR 2.8, 95% CI 1.1 to 6.9, P=0.02; respiratory system infection: HR 1.15, 95% CI 1.0 to 0.3, P-0.03), with expanded autosomal mosaic chromosomal alterations (mCAs) being associated with incident sepsis mortality (HR 2.0; 95% CI 1.0 to 4.2; P=0.05) (Table 4; FIGS. 17A-17C), as well as pneumonia history (OR 1.3; 95% CI: 1.1 to 1.5; P=0.0019).

TABLE 4

Association of mosaic chromosomal alterations (mCAs) with mortality from incident infection in Biobank Japan. Suggestive associations (P < 0.05) are presented among individuals without antecedent cancer prior to the infection phenotype.

| Phenotype | x | Sex | HR | P value | Controls (N) | Incident Cases (N) | Incident Cases with mCA (N) | Controls with mCA (N) |
|---|---|---|---|---|---|---|---|---|
| Nervous System Infection | Autosomal mCA | Male | 3.71 | 0.0085 | 39,978 | 17 | 8 | 6,298 |
| Meningitis or Encephalitis | | Male | 3.71 | 0.0085 | 39,978 | 17 | 8 | 6,298 |
| Pneumonia | | All | 1.16 | 0.023 | 72,317 | 1,299 | 334 | 10,485 |
| Nervous System Infection | | All | 2.81 | 0.025 | 72,317 | 21 | 8 | 10,485 |
| Meningitis or Encephalitis | | All | 2.81 | 0.025 | 72,317 | 21 | 8 | 10,485 |
| Respiratory System Infection | | All | 1.15 | 0.028 | 72,317 | 1,353 | 346 | 10,485 |
| Any Infection | | All | 1.12 | 0.037 | 72,317 | 1,998 | 476 | 10,485 |
| Pneumonia | | Male | 1.17 | 0.039 | 39,978 | 928 | 259 | 6,298 |
| Endocarditis or Myocarditis | | Female | 2.46 | 0.043 | 32,339 | 25 | 8 | 4,187 |
| Respiratory System Infection | | Male | 1.16 | 0.050 | 39,978 | 971 | 269 | 6,298 |
| Sepsis | Expanded | All | 2.04 | 0.050 | 72,317 | 276 | 8 | 753 |
| Sepsis | Autosomal mCA | All | 2.04 | 0.050 | 72,317 | 276 | 8 | 753 |

Figure 18:
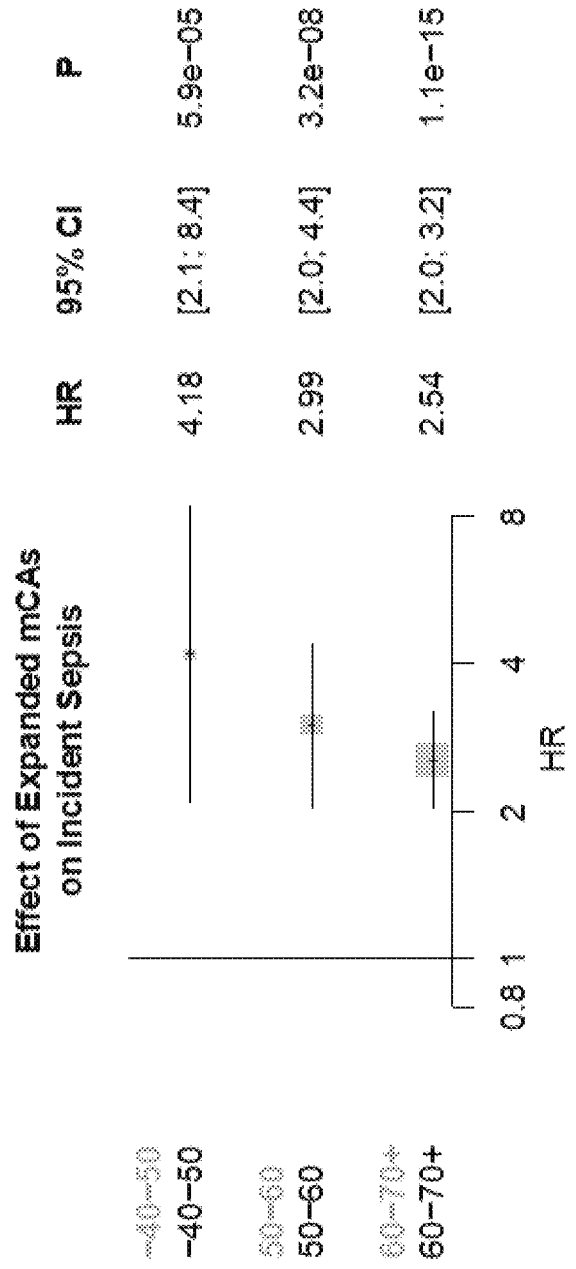
FIG. 18 is a forest plot with accompanying statistical information presenting an analysis of associations of expanded autosomal mCAs with incident sepsis and among different age strata. Individuals with prevalent hematologic cancer were excluded from analyses. Associations were adjusted for sex, ever smoking status, and principal components 1-10 of ancestry.
Figure 19A:
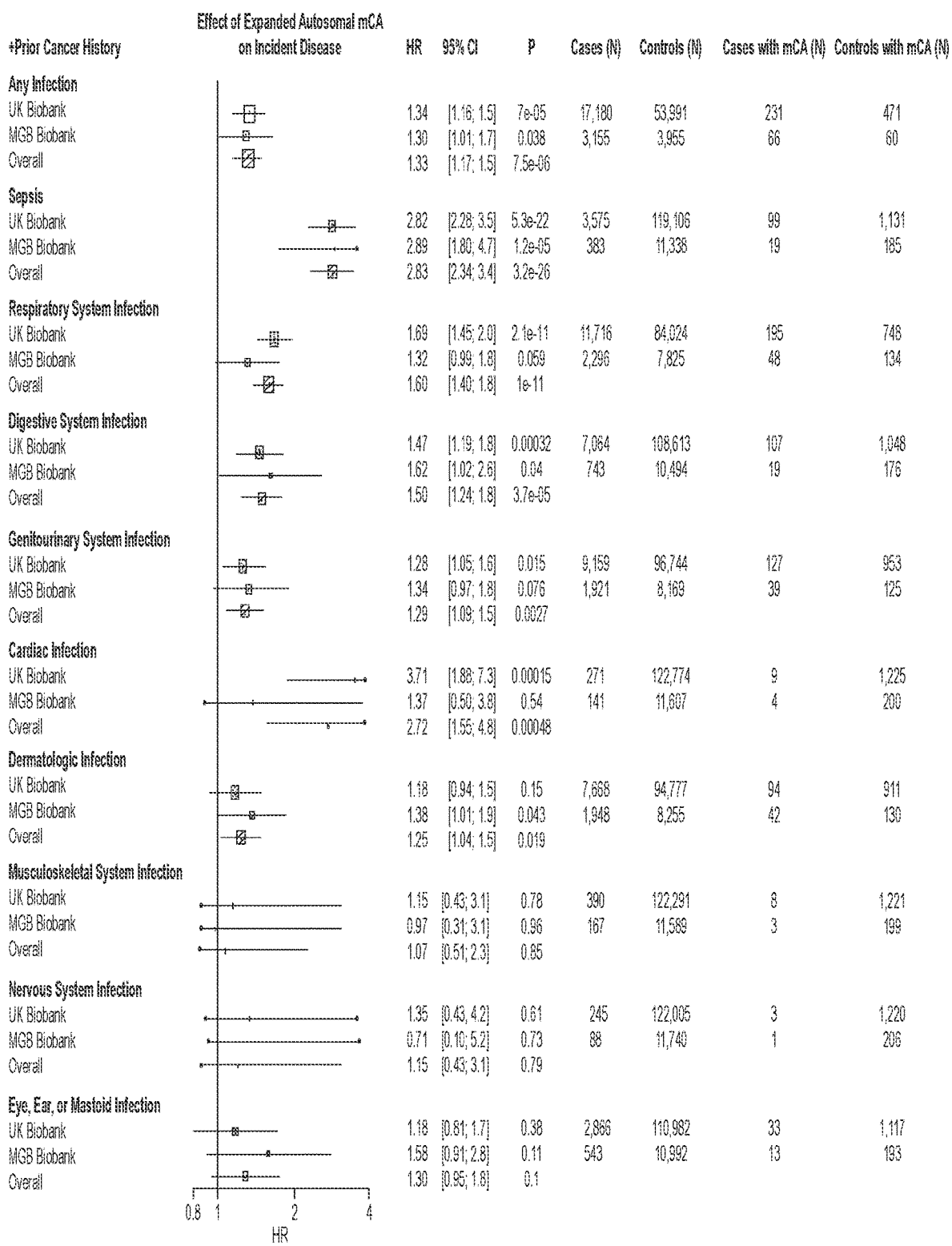
FIGS. 19A and 19B are forest plots with accompanying statistical information presenting an analysis of associations of expanded autosomal mosaic chromosomal alterations (mCAs) with incident infections among A) those with antecedent cancer (i.e., cancer prior to their infection) (FIG. 19A) B) those without antecedent cancer (FIG. 19B).
Figure 19B:
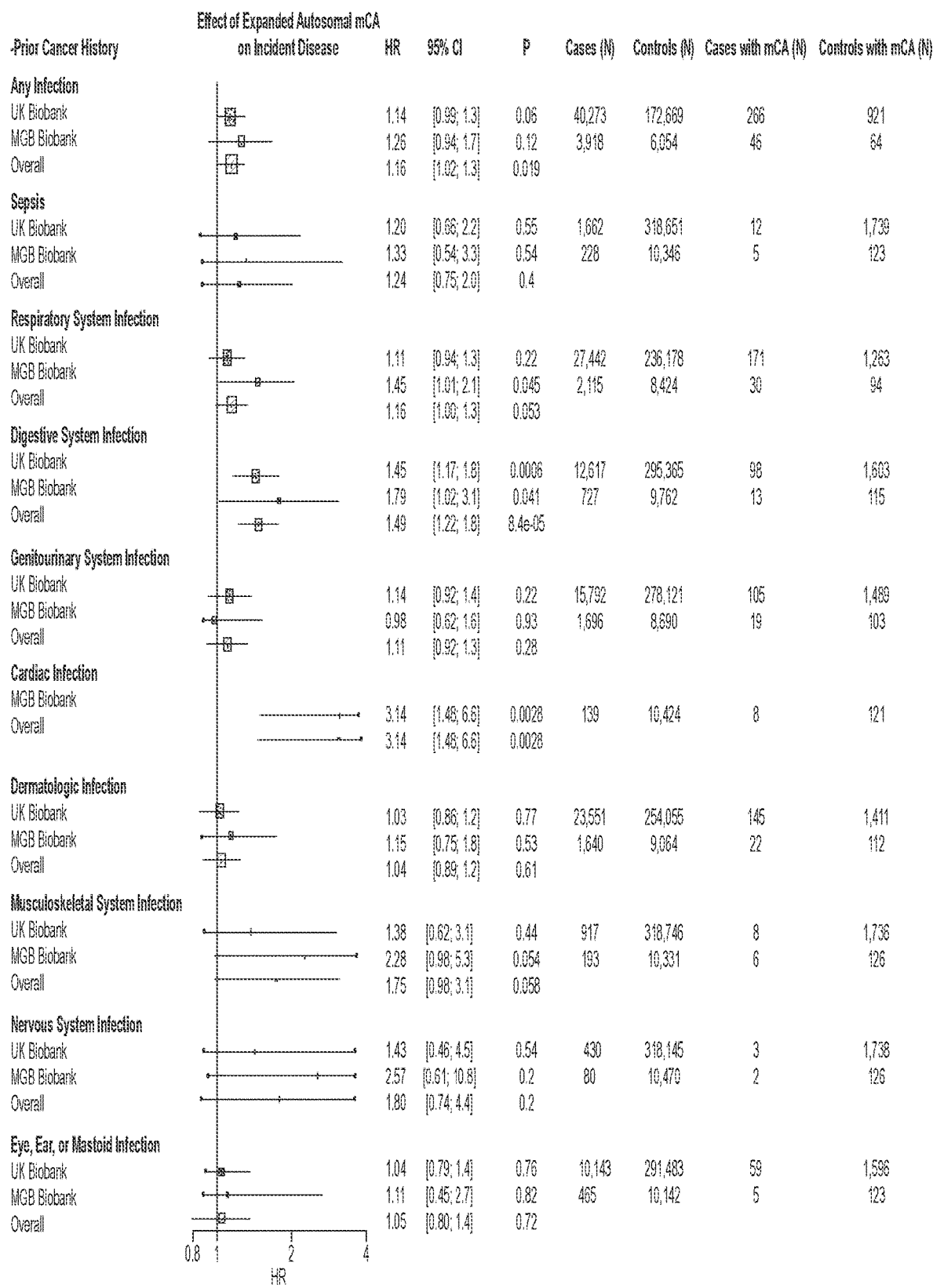
Figure 20A:
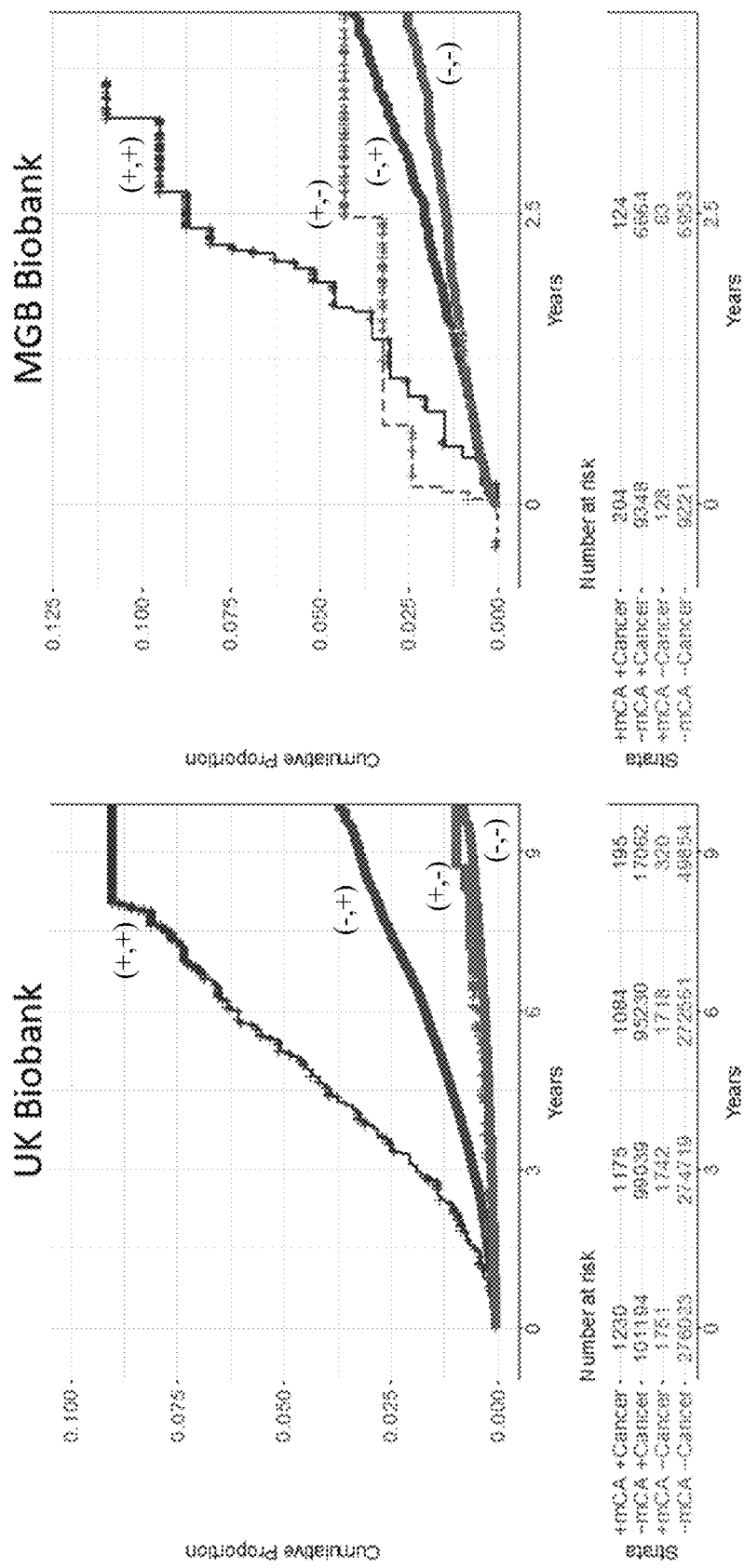
FIGS. 20A-20C are plots with accompanying statistical information presenting an analysis of an association of expanded autosomal mosaic chromosomal alterations (mCAs) with incident (FIG. 20A) sepsis, (FIG. 20B) pneumonia, and (FIG. 20C) digestive system infection across carrier status for expanded autosomal mCAs and any cancer diagnosis prior to the incident infection date. Individuals with known hematologic cancer at time of or prior to blood draw for genotyping were excluded.
Figure 20B:
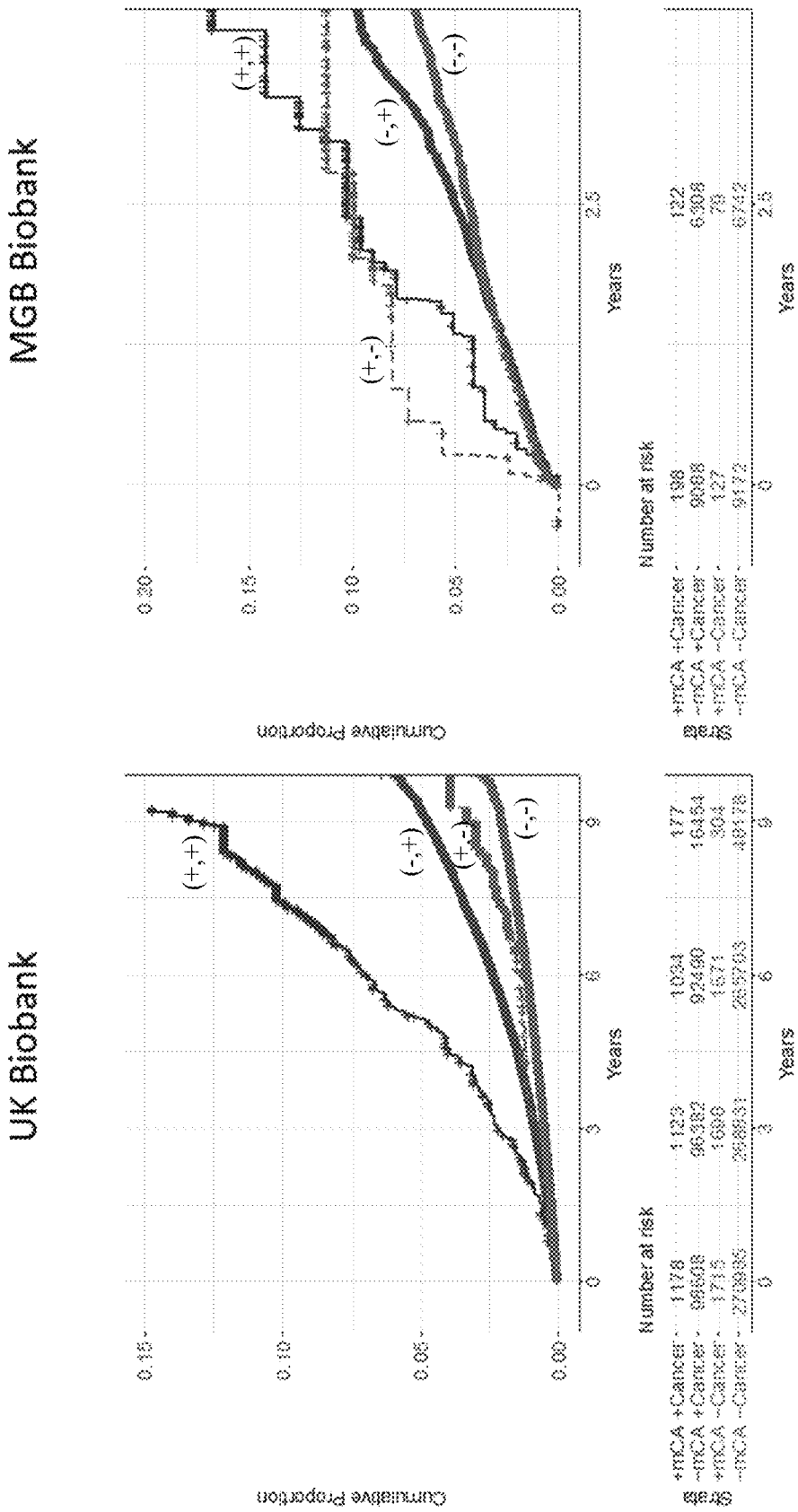
Figure 20C:
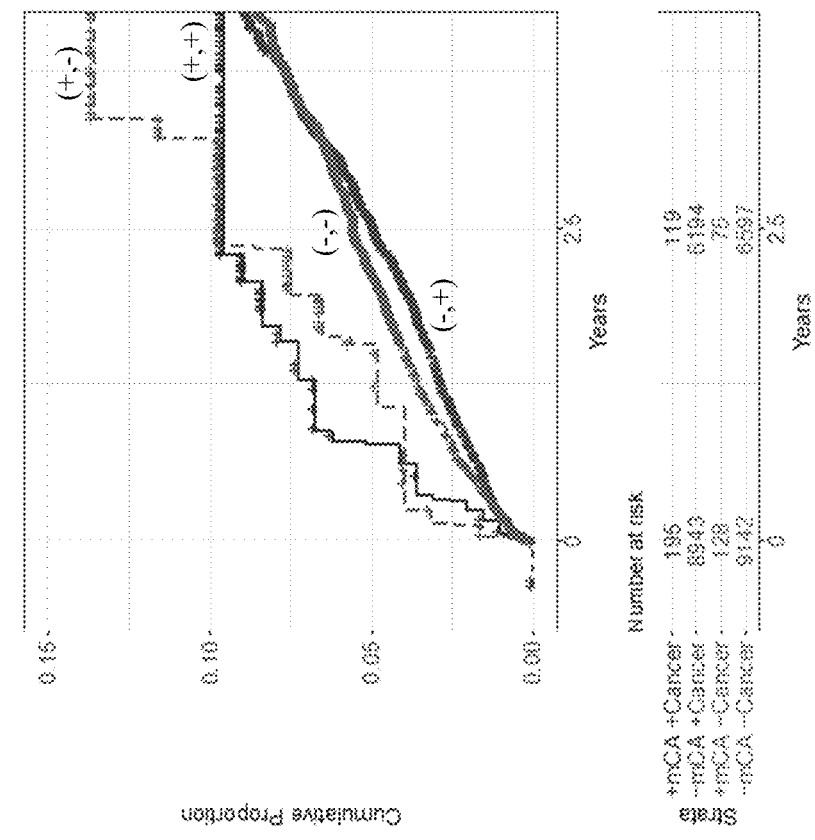
Figure 20C:
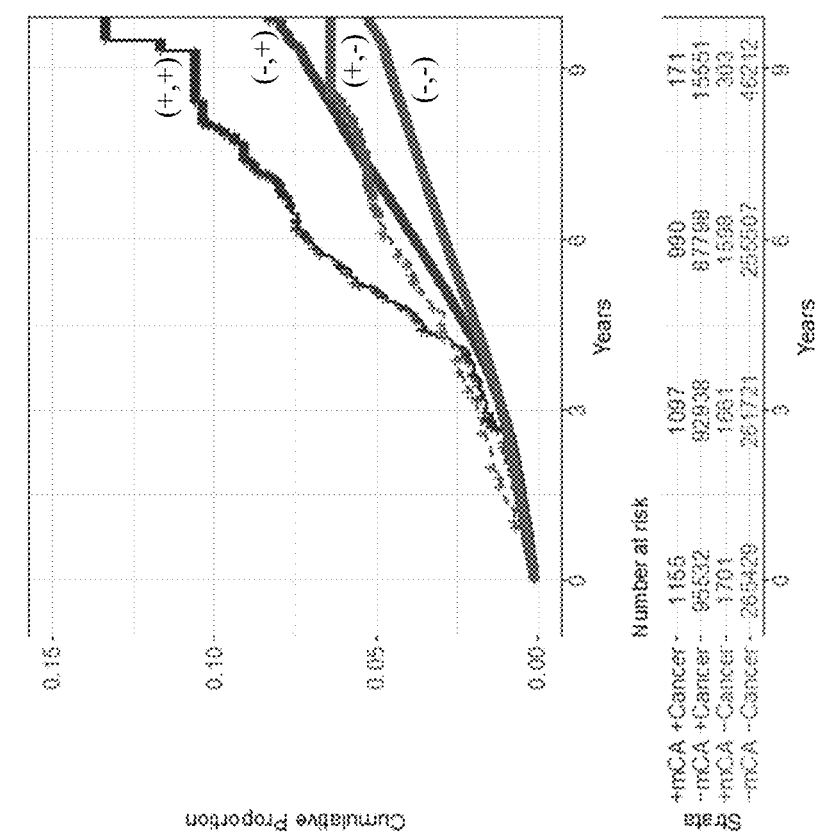
Figure 21:
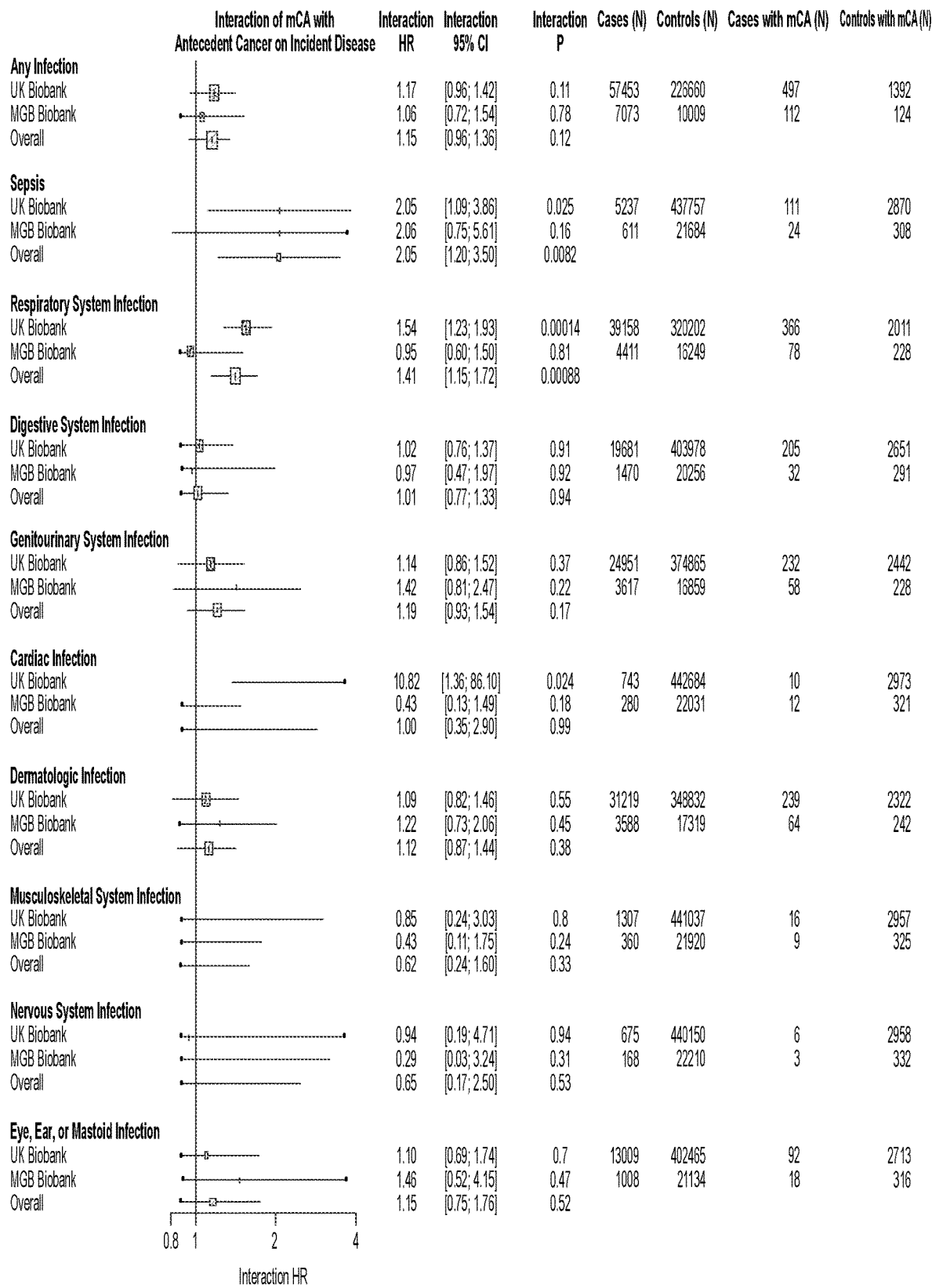
FIG. 21 is a forest plot with accompanying statistical information presenting an analysis of interactions of expanded autosomal mosaic chromosomal alterations (mCAs) with antecedent cancer prior to infection in the United Kingdom (UK) Biobank.

Sensitivity analysis for the association of expanded autosomal mCAs and incident sepsis found that the association was consistently significant across different age groups (FIG. 18), and that it was additionally independent of a 25-factor smoking covariate, body mass index, type 2 diabetes mellitus, leukocyte count, lymphocyte count, and lymphocyte percentage (Table 5). Stratified analyses indicated expanded autosomal mCAs in individuals with cancer prior to infection (either solid tumors or hematologic malignancy, excluding individuals with a history hematologic malignancy at time of blood draw for genotyping) conferred stronger effects for sepsis (HR 2.8; 95% CI 2.3 to 3.4; P=3.2×$10^{-26}$) and respiratory system infections (HR 1.6; 95% CI 1.4 to 1.8; P=1.0×$10^{-11}$) compared to individuals without a prior cancer history (sepsis: HR 1.2; 95% CI 0.8 to 2.0; P=0.4, $P_{interaction}$=8.2×$10^{-3}$; respiratory system infections: HR 1.2; 95% CI 1.0 to 1.3; P=0.05, $P_{interaction}$=8.8×$10^{-4}$) (FIGS. 3, 19A and 19B, 20A to 20C, and 21).

TABLE 5

Sensitivity analysis of incident sepsis association in the United Kingdom (UK) Biobank with the addition of a 25-factor smoking covariate, leukocyte count, e, lymphocyte count and percentage, body mass index (BMI), and prevalent type 2 diabetes. Where HR represents "hazard ratio", P represents "p-value", and CI represents "confidence interval".

| Incident Sepsis Multivariate Model Component | HR | P | Lower 95% CI | Upper 95% CI |
|---|---|---|---|---|
| Expanded Autosomal mCA | 2.00 | 2.64E−08 | 1.56 | 2.54 |
| Antecedent Cancer Prior to Incident Sepsis | 5.49 | <1E−300 | 5.09 | 5.93 |
| age | 1.02 | 0.64 | 0.95 | 1.09 |
| age$^2$ | 1.00 | 0.41 | 1.00 | 1.00 |
| Sex (Male) | 1.27 | 9.56E−11 | 1.18 | 1.37 |
| current cigar pipe smoker, former cigarette smoker | 1.90 | 0.011 | 1.16 | 3.12 |
| current cigar pipe smoker, not former cigarette smoker | 1.81 | 0.077 | 0.94 | 3.49 |
| current cigarette smoker, 10 to <20/day | 1.83 | 1.79E−10 | 1.52 | 2.20 |
| current cigarette smoker, 20 to <40/day | 2.06 | 8.23E−14 | 1.70 | 2.49 |
| current cigarette smoker, <10/day | 1.39 | 0.047 | 1.00 | 1.92 |
| current cigarette smoker, ≥40/day | 3.33 | 3.65E−05 | 1.88 | 5.89 |
| current occasional smoker, smoked cigarettes daily in past, <20/day | 1.37 | 0.19 | 0.86 | 2.18 |
| current occasional smoker, smoked cigarettes daily in past, ≥20/day | 1.83 | 0:01 | 1.13 | 2.96 |
| current occasional smoker, smoked cigars or pipes daily in past | 0.51 | 0.50 | 0.07 | 3.60 |
| current occasional smoker, smoked ≥100 cigarettes in lifetime | 0.99 | 0.94 | 0.70 | 1.39 |
| former cigarette smoker, <20/day, quit 1-5 year ago | 1.14 | 0.48 | 0.80 | 1.63 |
| former cigarette smoker, <20/day, quit 10-20 year ago | 1.15 | 0.27 | 0.90 | 1.46 |
| former cigarette smoker, <20/day, quit 5-10 year ago | 1.29 | 0.11 | 0.94 | 1.78 |
| former cigarette smoker, <20/day, quit <1 year ago | 1.90 | 0.06 | 0.98 | 3.65 |
| former cigarette smoker, <20/day, quit ≥20 year ago | 1.08 | 0.34 | 0.92 | 1.26 |
| former cigarette smoker, ≥20/day, quit 1-5 year ago | 2.25 | 1.07E−13 | 1.82 | 2.79 |
| former cigarette smoker, ≥20/day, quit 10-20 year ago | 1.54 | 7.00E−07 | 1.30 | 1.82 |
| former cigarette smoker, ≥20/day, quit 5-10 year ago | 1.64 | 1.11E−05 | 1.31 | 2.04 |
| former cigarette smoker, ≥20/day, quit <1 year ago | 2.08 | 0.0064 | 1.23 | 3.53 |
| former cigarette smoker, ≥20/day, quit ≥20 year ago | 1.25 | 0.00080 | 1.10 | 1.42 |
| former daily cigar pipe smoker | 1.23 | 0.19 | 0.91 | 1.66 |
| former occasional cigarette smoker, lifetime cigarette smoking unknown | 1.07 | 0.76 | 0.70 | 1.63 |
| former occasional cigarette smoker, smoked <100 cigarettes in lifetime | 1.27 | 0.085 | 0.97 | 1.66 |
| former occasional cigarette smoker, smoked ≥100 cigarettes in lifetime | 1.02 | 0.72 | 0.90 | 1.17 |
| Missing smoking | 1.55 | 0.0085 | 1.12 | 2.15 |
| BMI (SD) | 1.21 | 7.08E−31 | 1:17 | 1.25 |
| Prevalent Type 2 Diabetes | 1.84 | 1.75E−16 | 1.59 | 2.12 |
| Leukocyte count (SD) | 1.31 | 1.38E−07 | 1.19 | 1.45 |
| Lymphocyte count (SD) | 0.71 | 4.57E−07 | 0.63 | 0.81 |
| Lymphocyte percentage (SD) | 1.12 | 0.054 | 1.00 | 1.27 |
| PC1 | 0.98 | 0.18 | 0.96 | 1.01 |
| PC2 | 0.99 | 0.42 | 0.97 | 1.01 |
| PC3 | 0.99 | 0.59 | 0.97 | 1.02 |
| PC4 | 0.99 | 0.37 | 0.98 | 1.01 |
| PC5 | 1.01 | 0.07 | 1.00 | 1.01 |
| PC6 | 1.01 | 0.46 | 0.99 | 1.03 |
| PC7 | 0.99 | 0.23 | 0.97 | 1.01 |
| PC8 | 1.01 | 0.58 | 0.99 | 1.03 |
| PC9 | 1.00 | 0.58 | 0.99 | 1.01 |
| PC10 | 1.00 | 0.61 | 0.99 | 1.02 |

Figure 22A:
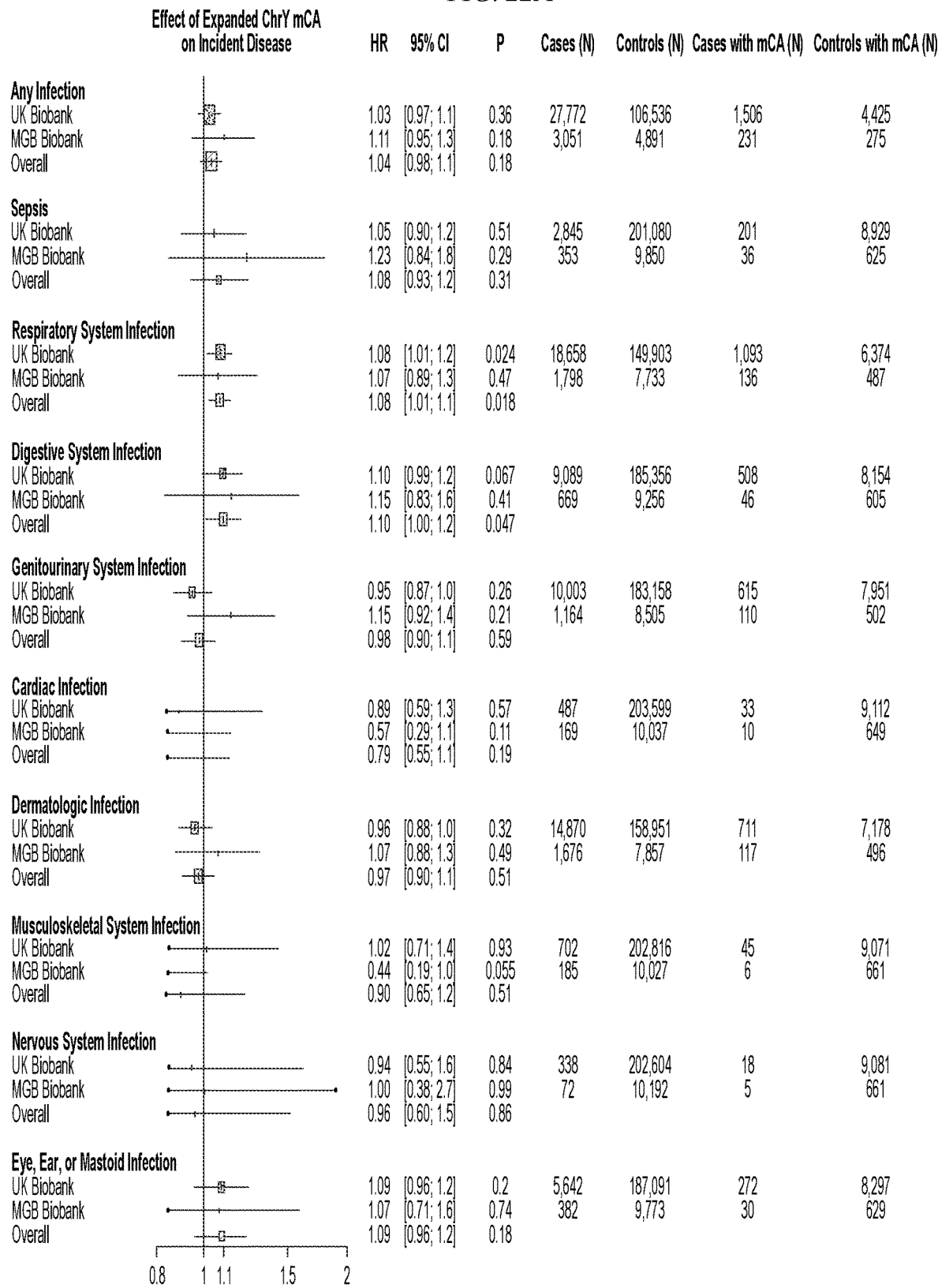
FIGS. 22A and 22B are forest plots with accompanying statistical information presenting an analysis of associations of A) expanded chromosome Y (ChrY) (FIG. 22A) and B) expanded chromosome X (ChrX) mosaic chromosomal alterations (mCAs) (FIG. 22B) with incident infections.
Figure 22B:
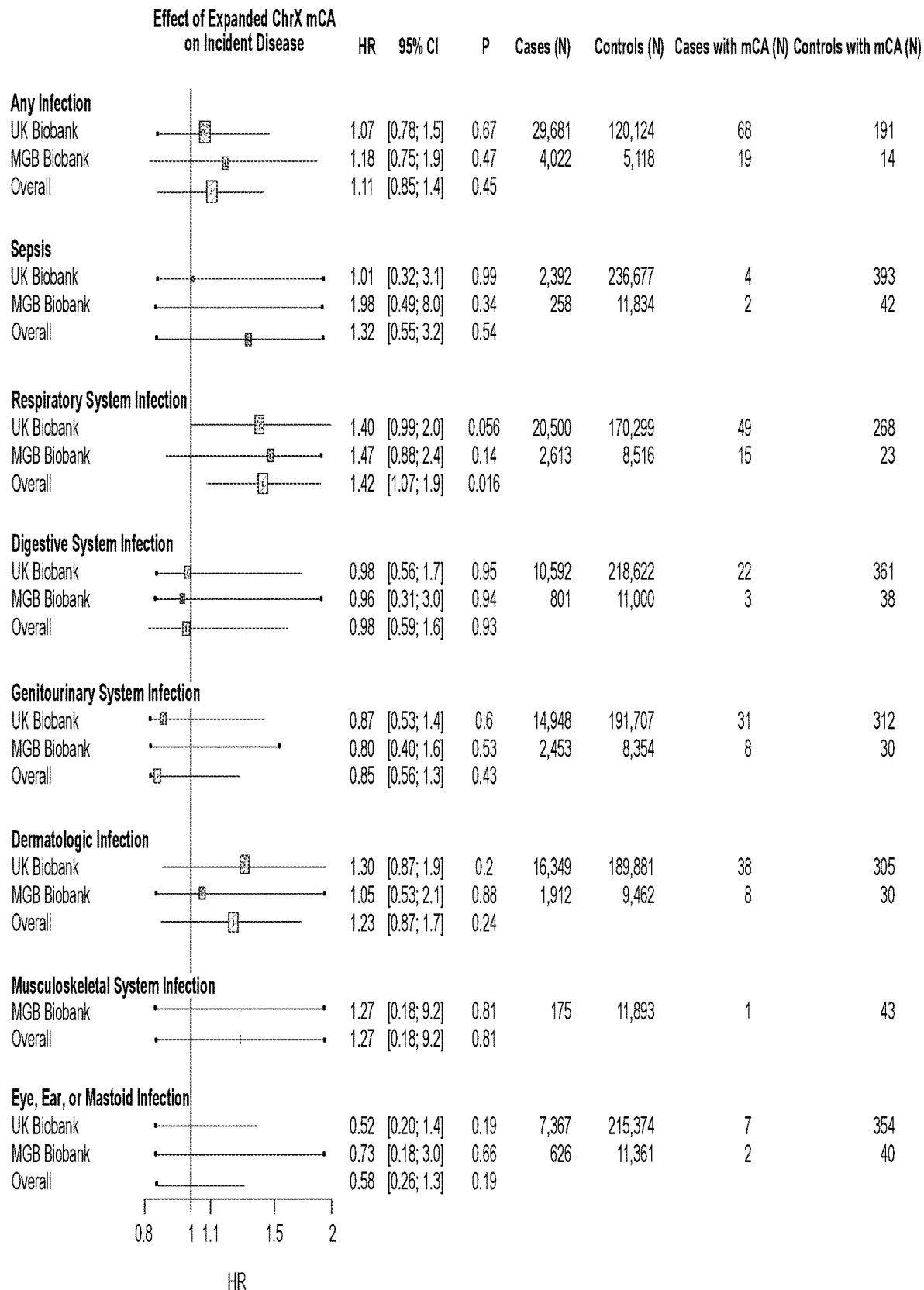

While several associations of organ-system infections with expanded chromosome Y (ChrY) mosaic chromosomal alterations (mCAs) were nominal (respiratory system infection: HR 1.08; 95% CI 1.0 to 1.1; P=0.02; digestive system infection: HR 1.1; 95% CI 1.0 to 1.2; P=0.05), none of the expanded chromosome X (ChrX) or chromosome Y (ChrY) mosaic chromosomal alteration (mCA) associations with organ-system infections attained statistical significance (FIGS. 22A-22B).

Example 4: Association with Coronavirus Disease 2019 (COVID-19) Hospitalization

Figure 4A:
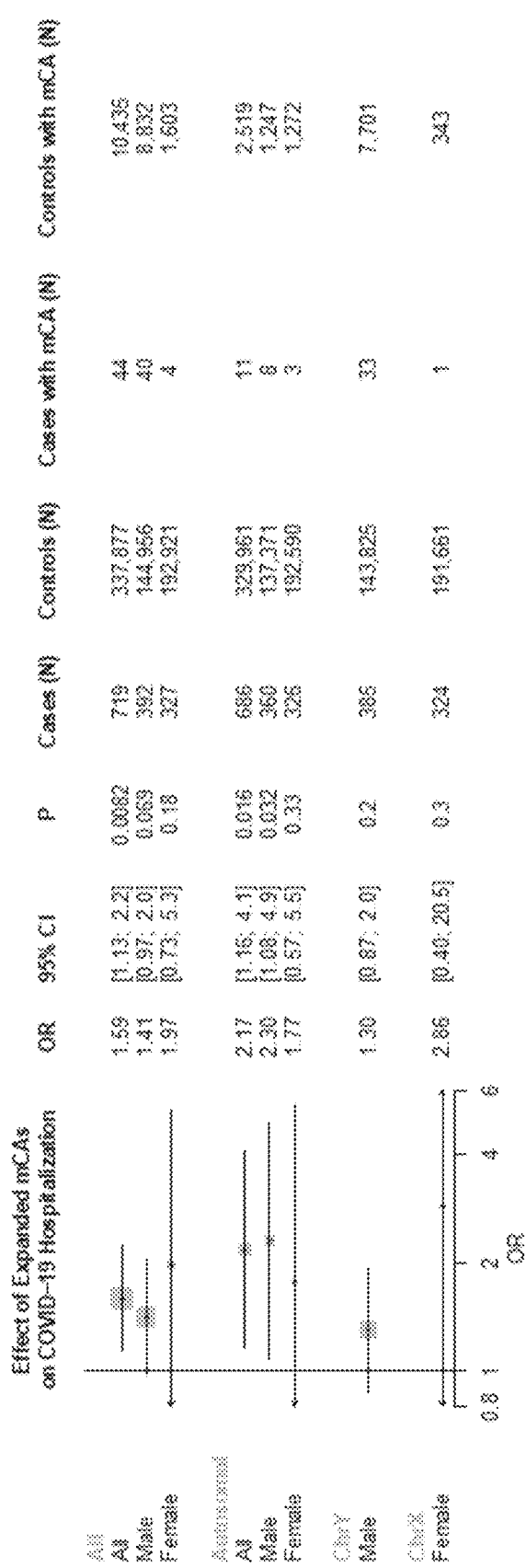
FIGS. 4A and 4B are forest plots with accompanying statistical information presenting an analysis of an association of expanded mosaic chromosomal alterations (mCAs) with a) coronavirus disease 2019 (COVID-19) hospitalization, see FIG. 4A, and b) incident pneumonia by sex in the United Kingdom Biobank (UKB), see FIG. 4B. Individuals with known hematologic cancer at time of or prior to blood draw for genotyping were excluded. Analyses are adjusted for age, age$^2$, sex, ever smoking status, and principal components of ancestry. Throughout the figures, OR stands for "odds ratio".
Figure 4B:
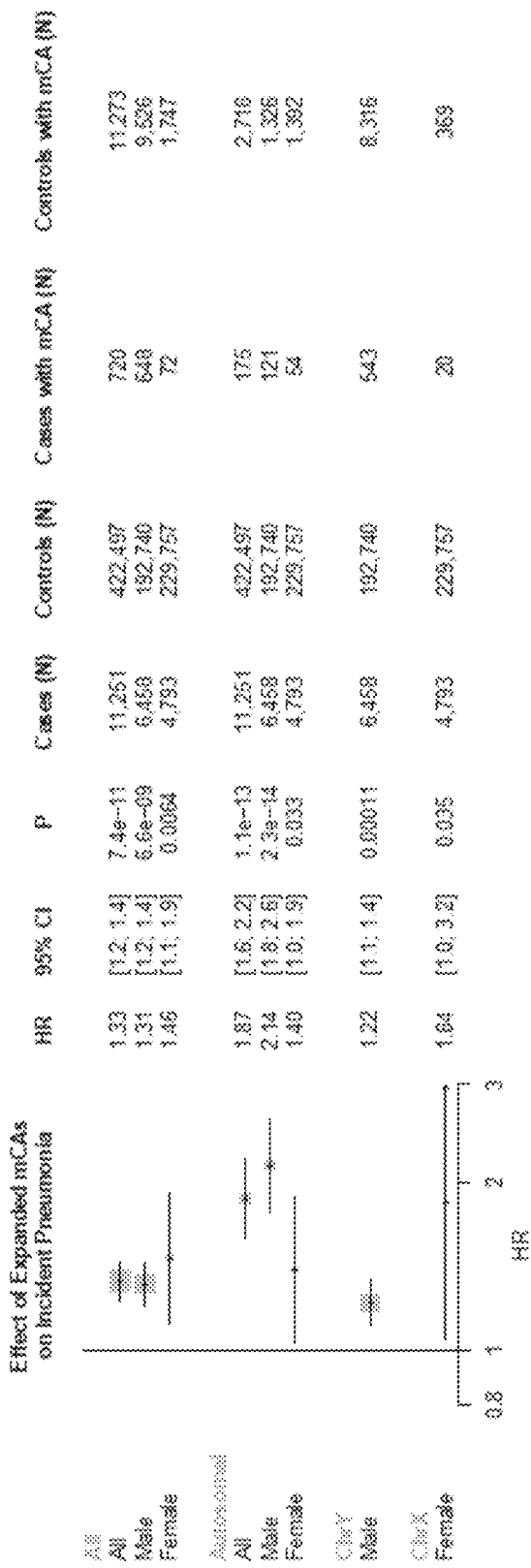
Figure 23A:
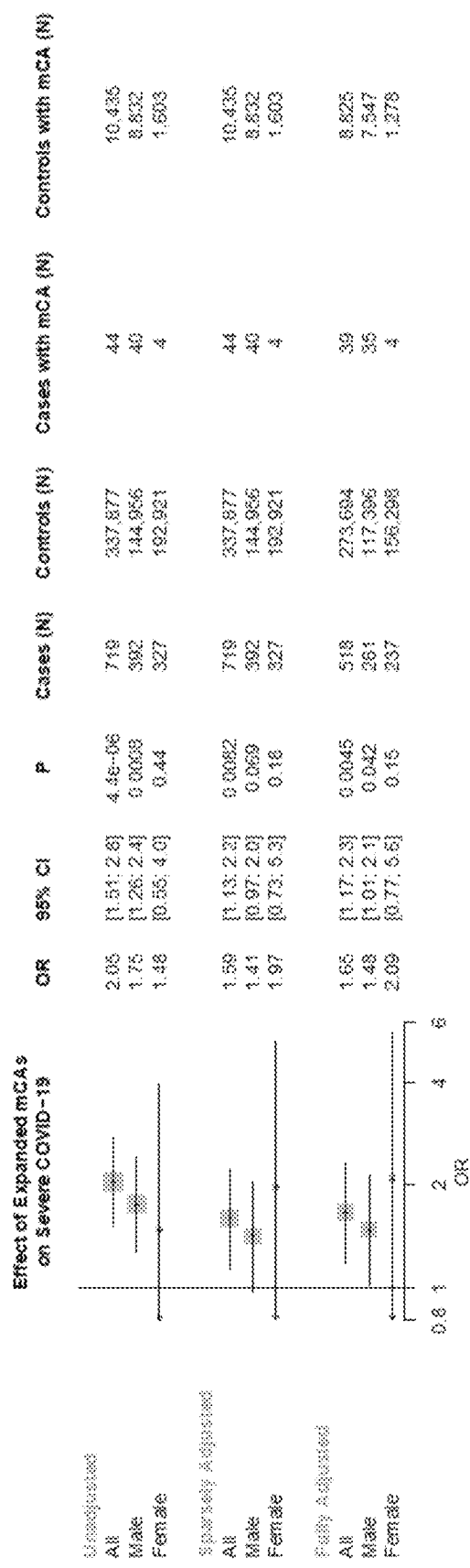
FIGS. 23A and 23B are forest plots with accompanying statistical information presenting an analysis of associations of expanded mosaic chromosomal alterations (mCAs) with (FIG. 23A) coronavirus disease 2019 (COVID-19) hospitalization across different adjustment models, and (FIG. 23B) different COVID-19 phenotypes in a fully adjusted model. Adjustment models include 1) an unadjusted model, 2) a sparsely adjusted model which adjusts for age, age2, sex, smoking status, and principal components of ancestry, and 3) a fully adjusted model which additionally adjusts for Townsend deprivation index, body mass index (BMI), and the following comorbidities: Asthma, chronic obstructive pulmonary disease (COPD), coronary artery disease (CAD), type 2 diabetes (T2D), any cancer, and hypertension (HTN).
Figure 23B:
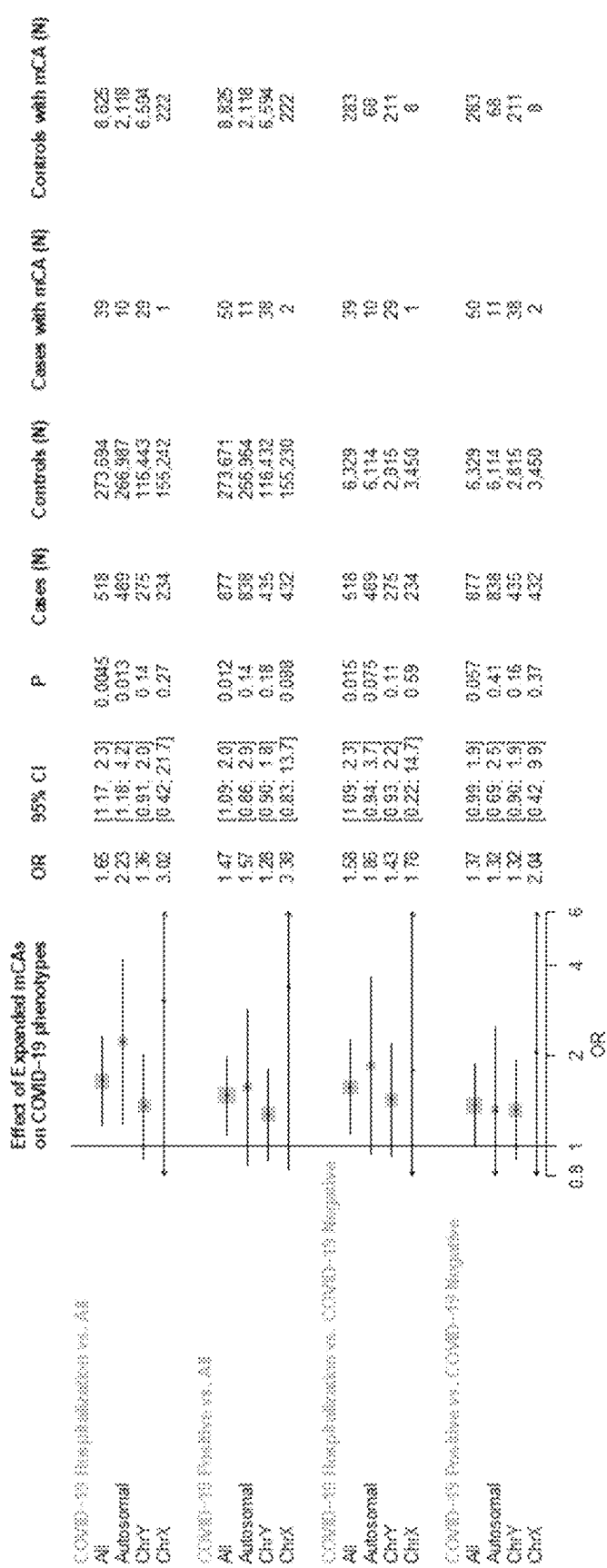

Across 719 coronavirus disease 2019 (COVID-19) hospitalized cases in the United Kingdom Biobank (UKB), 44 individuals (6%) carried an expanded mosaic chromosomal alteration (mCA) clone at time of enrollment (in 2010), versus 3% among 337,877 controls. Adjusting for age, age2, sex, prior or current smoking status, and principal components of ancestry, expanded mosaic chromosomal alterations (mCAs) were associated with coronavirus disease 2019 (COVID-19) hospitalizations (OR 1.6; 95% CI 1.1 to 2.2; P=0.0082), with similar effects with expanded autosomal mosaic chromosomal alterations (mCAs) (OR 2.2; 95% CI 1.2 to 4.1; P=0.02) (FIG. 4A). Associations persisted with additional adjustment for normalized Townsend deprivation index, normalized body mass index, type 2 diabetes mellitus, hypertension, coronary artery disease, any cancer, asthma, and chronic obstructive pulmonary disease, finding similar associations (FIG. 23A). Additionally, similar associations were observed when comparing COVID-19 hospitalization to tested negative controls, and COVID-19 positive versus all from English provinces and, separately, versus tested negative controls (FIG. 23B). Similar effects of expanded mosaic chromosomal alterations (mCAs) with coronavirus disease 2019 (COVID-19) were also observed with incident pneumonia in the United Kingdom Biobank (UKB) (FIG. 4B).

Mosaic chromosomal alterations (mCAs) identified in peripheral leukocyte DNA from 767,891 individuals across the UK Biobank (UKB; N=444,199), Mass General Brigham Biobank (MGBB; N=22,461), FinnGen Biobank (N=175,690), and BioBank Japan (BBJ; N=125,541) without hematological cancer were analyzed. Expanded mCAs (present in >10% of leukocytes) were associated with diverse incident infections. Associations of mCAs with infection mortality were pursued among 125,541 participants in Biobank Japan (BBJ).

The frequency of expanded (cell fraction >10%) autosomal mCAs across all cohorts was 0.27% among individuals <40 years, 0.52% among 40-60 years, 1.5% among 60-80 years, and 4.6% among those greater than 80 years, with men having ~1.5×increased odds of having an expanded autosomal mCA. Expanded mCAs were age-dependent, approaching 4% prevalence by 60 years of age and were associated with elevated lymphocyte count. In UKB and MGBB, expanded mCAs were associated with increased risk for diverse incident infections (hazard ratio (HR) 1.12; 95% confidence interval (CI) 1.1 to 1.2), with strongest associations observed for expanded autosomal mCAs with incident sepsis (HR 2.8; 95% CI 2.3 to 3.3) and pneumonia (HR 1.9; 95% CI 1.6 to 2.2).

Interactions of expanded autosomal mCAs with prior cancer were detected, with associations for sepsis and respiratory infections primarily observed in cancer patients. In BBJ, expanded autosomal mCAs were nominally associated with sepsis mortality (HR 2.0; 95% CI 1.0 to 4.0). Expanded autosomal mCAs were also more prevalent among those hospitalized with coronavirus disease 2019 (COVID-19) (OR 2.2; 95% CI 1.2 to 4.1) in the UKB. Expanded mCAs were associated with diverse incident infections in models adjusted for age, age2, sex, smoking status, and principal components of ancestry. Meta-analyzed across UKB, MGBB, and FinnGen, expanded mCAs were associated with increased risk for diverse incident infections (hazard ratio (HR) 1.12, P=$6.3 \times 10^{-7}$), with strongest associations observed for expanded autosomal mCAs with incident sepsis (HR 2.7, P=$3.1 \times 10^{-28}$), pneumonia (HR 1.8, P=$2.3 \times 10^{-15}$), digestive system infections (HR=1.5, P=$6.5 \times 10^{-10}$), genitourinary infections (HR=1.3, P=0.0005), and cardiac infections (HR=2.0, P=0.002). Interactions of expanded autosomal mCAs with prior cancer were detected, with associations for sepsis and respiratory infections primarily observed in cancer patients. In BBJ, expanded autosomal mCAs were nominally associated with sepsis mortality (HR 2.0, P=0.05).

Expanded autosomal mCAs were also more prevalent among those hospitalized with coronavirus disease 2019 (COVID-19) (OR 2.2, 95% confidence interval (CI): 1.2-4.1, p-value (P)-0.01) in the UKB, independent of age, age2, sex, smoking status, principal components of ancestry, Townsend deprivation index, any cancer, chronic respiratory disease, hypertension, diabetes mellitus, coronary artery disease, and body mass index (BMI). Replication of this finding was performed in FinnGen (odds ratio (OR)=8.8, 95% CI: 1.1-72.3, P=0.04), with the meta-analyzed associations being OR=2.4, P=0.004.

Examples 1-4 demonstrate that expanded mosaic chromosomal alterations (mCAs) are associated with increased risk for infectious outcomes, including coronavirus disease 2019 (COVID-19). Clonally expanded mCAs were identified as a novel risk factor for diverse infections, including severe COVID-19.

Methods of the Examples

The following methods were employed in the above examples.

Study Samples

A total of 592,201 individuals across three biobanks were analysed: United Kingdom Biobank (UKB), Mass General Brigham Biobank (MGBB), and Biobank Japan (BBJ). Across all three cohorts, written informed consent was previously obtained from all participants. Individuals with known hematologic cancer at time of or prior to blood draw for genotyping were removed from all analyses. Additional information on each cohort is provided below.

Mosaic Chromosomal Alteration Detection

Mosaic chromosomal alterations (mCA) were detected in the United Kingdom Biobank (UKB) and Biobank Japan (BBJ), as described in Terao C, Suzuki A, Momozawa Y, et al. "Chromosomal alterations among age-related haematopoietic clones in Japan," Nature 2020; Loh P R, Genovese G, McCarroll S A. "Monogenic and polygenic inheritance become instruments for clonal selection," *Nature* 2020; and Loh P R, Genovese G, Handsaker R E, et al. "Insights into clonal haematopoiesis from 8,342 mosaic chromosomal alterations," *Nature* (2018) 559:350-5.

Mosaic chromosomal alterations (mCA) detection in the Mass General Brigham Biobank (MGBB) was performed with the Mosaic Chromosomal Alterations (MoChA) software and pipeline. Briefly, genotype intensities were transformed to log 2 R ratio (LRR) and B-allele frequency (BAF) values to estimate total and relative allelic intensities, respectively, as described in Peiffer D A, Le J M, Steemers F J, et al. "High-resolution genomic profiling of chromosomal aberrations using Infinium whole-genome genotyping," *Genome Res* (2006) 16:1136-48. Further details regarding mCA detection are provided below and in FIGS. 5A and 5B. Across all three studies, expanded mosaic chromosomal alteration (mCA) refers to the presence of at least one detectable mosaic chromosomal alteration (mCA) present in >10% of circulating leukocytes (e.g., cell fraction >10%). Autosomal and sex chromosomes were also separately considered; only autosomal mosaic chromosomal alterations (mCAs) were available for Biobank Japan (BBJ).

Clinical Outcomes

In the United Kingdom Biobank (UKB) the first reported occurrences over median 8-year follow-up in Category 2410 were used as categorized by the United Kingdom Biobank (UKB) which maps primary care data, ICD-9 and ICD-10 codes from hospital inpatient data, ICD-10 codes in death register records, and self-reported medical conditions reported at the baseline, to ICD-10 codes. For each set of phenotypes grouped by organ system or by category, the time to first incident event after baseline examination in individuals free of prevalent history of each disease category was used. In the Mass General Brigham Biobank (MGBB), electronic health record data was used to define incident ICD-10 codes grouped in the same fashion after DNA collection date over a median 3-year follow-up. In Biobank Japan (BBJ), was analyses were performed using fatal incident events attributed to diverse infection outcomes since non-fatal incident events were not available; additionally, analyses for pneumonia were performed using history of pneumonia prior to genotyping, based on interviews and medical record reviews.

United Kingdom Biobank (UKB) coronavirus disease 2019 (COVID-19), from severe acute respiratory syndrome coronavirus 2 (SARS-COV-2) infection, phenotypes used in the present analysis were downloaded on Jul. 27, 2020. Severe acute respiratory syndrome coronavirus 2 (SARS-COV-2) infection was determined by polymerase chain reaction from nasopharyngeal, oropharyngeal, or lower respiratory samples obtained between Mar. 16, 2020 and Jul.

17, 2020. Coronavirus disease 2019 (COVID-19) hospitalized cases were defined as any individual with at least one positive test who also had evidence for inpatient hospitalization (Field 40100). Controls included two sets: (1) participants from United Kingdom Biobank (UKB) English recruitment centers who were not known to have coronavirus disease 2019 (COVID-19), which were individuals with negative or no known severe acute respiratory syndrome coronavirus 2 (SARS-COV-2) testing or (2) participants with a negative SARS-COV test. Individuals with coronavirus disease 2019 (COVID-19) of unknown or low severity (i.e., at least one positive severe acute respiratory syndrome coronavirus 2 (SARS-COV-2) test without a known hospitalization) were excluded from the primary analyses. Individuals who died prior to Mar. 1, 2020, and therefore not at risk for coronavirus disease 2019 (COVID-19) infection, were excluded from coronavirus disease 2019 (COVID-19) analyses.

Statistical Methods

Association analyses of expanded mosaic chromosomal alterations (mCAs) with primary incident infection across 10 main infectious disease organ system categories were performed using Cox proportional hazards models, adjusting for age, age2, sex, ever smoking status, and principal components 1-10 from the genotyping data. Time since DNA collection was used as the underlying timescale. The proportional hazards assumption was assessed by Schoenfeld residuals and was not rejected. Individuals with a history of hematological cancer prior to DNA collection were excluded. P-value threshold for significance among the primary organ system infection analyses was two-sided 0.05/10=0.005 to account for multiple hypothesis-testing. Secondary and sensitivity analyses are detailed below. Analyses of incident events were performed separately in each biobank using the survival package in R (version 3.5, R Foundation, Vienna, Austria). Meta-analyses of the UKB and MGBB results were performed using a fixed effects model from the meta package.

For United Kingdom Biobank (UKB), logistic regression was performed to estimate the association between expanded mosaic chromosomal alterations (mCAs) and coronavirus disease 2019 (COVID-19) hospitalization, using the aforementioned phenotype definition, adjusting for sex, age, age$^2$, smoking status, and the first ten principal components from the genotyping data. As above, individuals with prevalent hematologic cancer were excluded from analyses. For the coronavirus disease 2019 (COVID-19) analyses, statistical significance was assigned at two-sided p-value<0.05. Secondary multi-variable models were additionally adjusted for normalized Townsend deprivation index, inverse rank normalized body mass index at baseline, type 2 diabetes mellitus, hypertension, coronary artery disease, any cancer, asthma, and chronic obstructive pulmonary disease.

Cohorts

The UK Biobank, a population-based cohort of approximately 500,000 participants recruited from 2006-2010, had existing genomic and longitudinal phenotypic data. Baseline assessments were conducted at 22 assessment centres across the UK with sample collections including blood-derived DNA. Of 488,377 genotyped individuals, 445,101 were analysed consisting of participants consenting to genetic analyses and who passed sample quality control criteria for mosaic chromosomal alteration (mCA) calling: A) had genotypic-phenotypic sex concordance, B) no 1st or 2nd degree relatives (random exclusion of one from each pair), and C) no prevalent hematologic cancer at time of blood draw. Genome-wide genotyping of blood-derived DNA was performed by UK Biobank using two genotyping arrays sharing 95% of marker content: Applied Biosystems UK BiLEVE Axiom Array (807,411 markers in 49,950 participants) and Applied Biosystems UK Biobank Axiom Array (825,927 markers in 438,427 participants) both by Affymetrix (Santa Clara, CA).

The Mass General Brigham Biobank (MGBB) contains genotypic and clinical data from >105,000 patients who consented to broad-based research across 7 regional hospitals. Baseline phenotypes were ascertained from the electronic medical record (EMR) and surveys on lifestyle, environment, and family history. Of the approximately 36,000 genotyped individuals, 27,778 samples had available probe raw intensity data (IDAT) files for mosaic chromosomal alteration (mCA) calling. Blood-derived DNA samples were genotyped using three versions of the Multi-Ethnic Genotyping Array (MEGA) SNP array offered by Illumina.

Biobank Japan (BBJ) is a hospital-based registry that collected clinical, DNA, and serum samples from approximately 200,000 consented patients with one or more of 47 target diseases at a total of 66 hospitals between 2003-2007. Blood DNA was genotyped in three batches using different arrays or set of arrays, namely: (1) a combination of Illumina Infinium Omni Express and Human Exome; (2) Infinium Omni Express Exome v.1.0; and (3) Infinium Omni Express Exome v.1.2, which capture very similar SNPs.

Mosaic Chromosomal Alteration Detection

Mosaic chromosomal alteration (mCA) detection in the UK Biobank was done as described in Loh P R, Genovese G, Handsaker R E, et al. "Insights into clonal haematopoiesis from 8,342 mosaic chromosomal alterations," Nature (2018) 559:350-5 and in Loh P R, Genovese G, McCarroll S A, "Monogenic and polygenic inheritance become instruments for clonal selection," Nature 2020. Briefly, genotype intensities were transformed to log 2(R ratio) (LRR) and B-allele frequency (BAF values) to estimate total and relative allelic intensities, respectively. Re-phasing was performed using Eagle2 and mosaic chromosomal alteration (mCA) calling was performed by leveraging long-range phase information to search for allelic imbalances between maternal and paternal allelic fractions across contiguous genomic segments. Constitutional duplications and low-quality calls were filtered out and cell fraction was estimated as described in Loh P R, Genovese G, Handsaker R E, et al. "Insights into clonal haematopoiesis from 8,342 mosaic chromosomal alterations," Nature (2018) 559:350-5. UK Biobank mosaic chromosomal alteration (mCA) calls were obtained from dataset Return 2062 generated from UK Biobank application 19808.

Figure 5A:
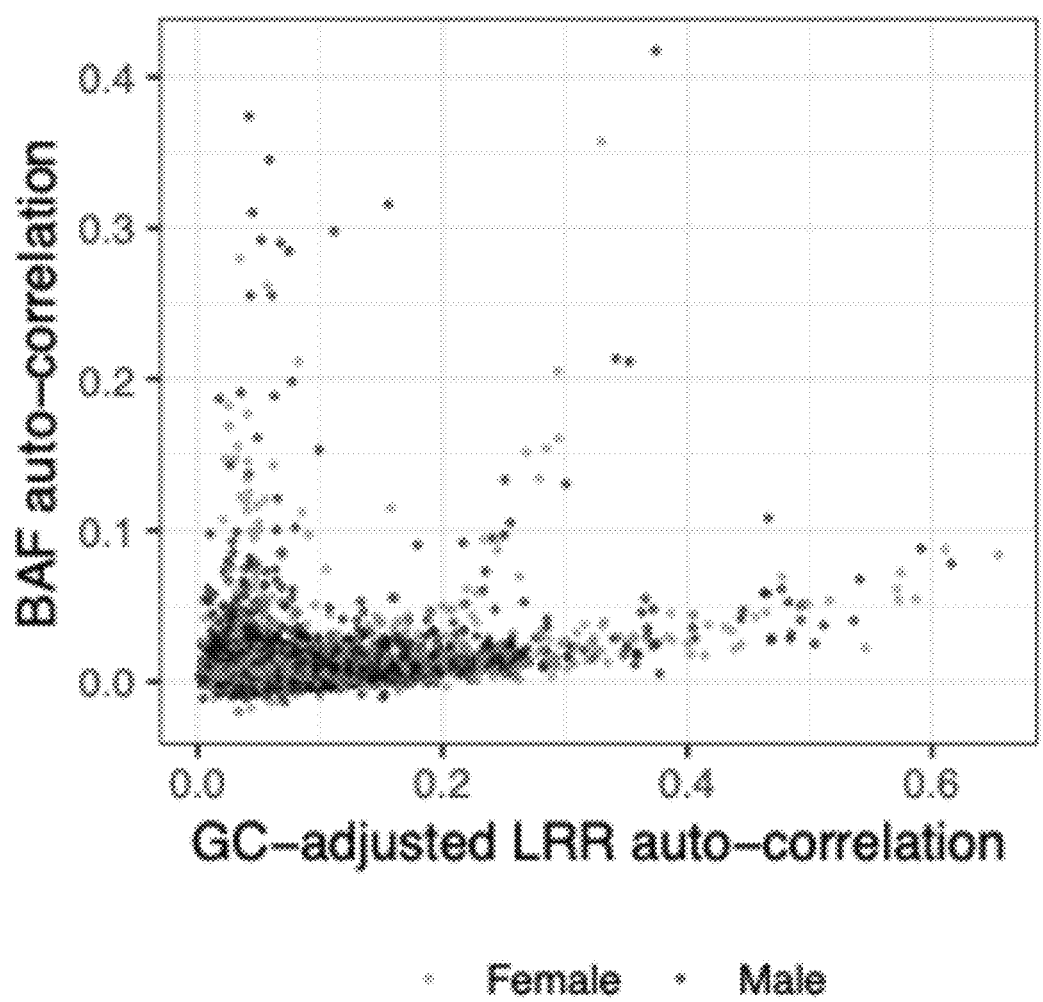
FIGS. 5A and 5B are scatter plots showing Mass General Brigham (MGB) Biobank mosaic chromosomal alteration (mCA) sample quality control analyses.
Figure 5B:
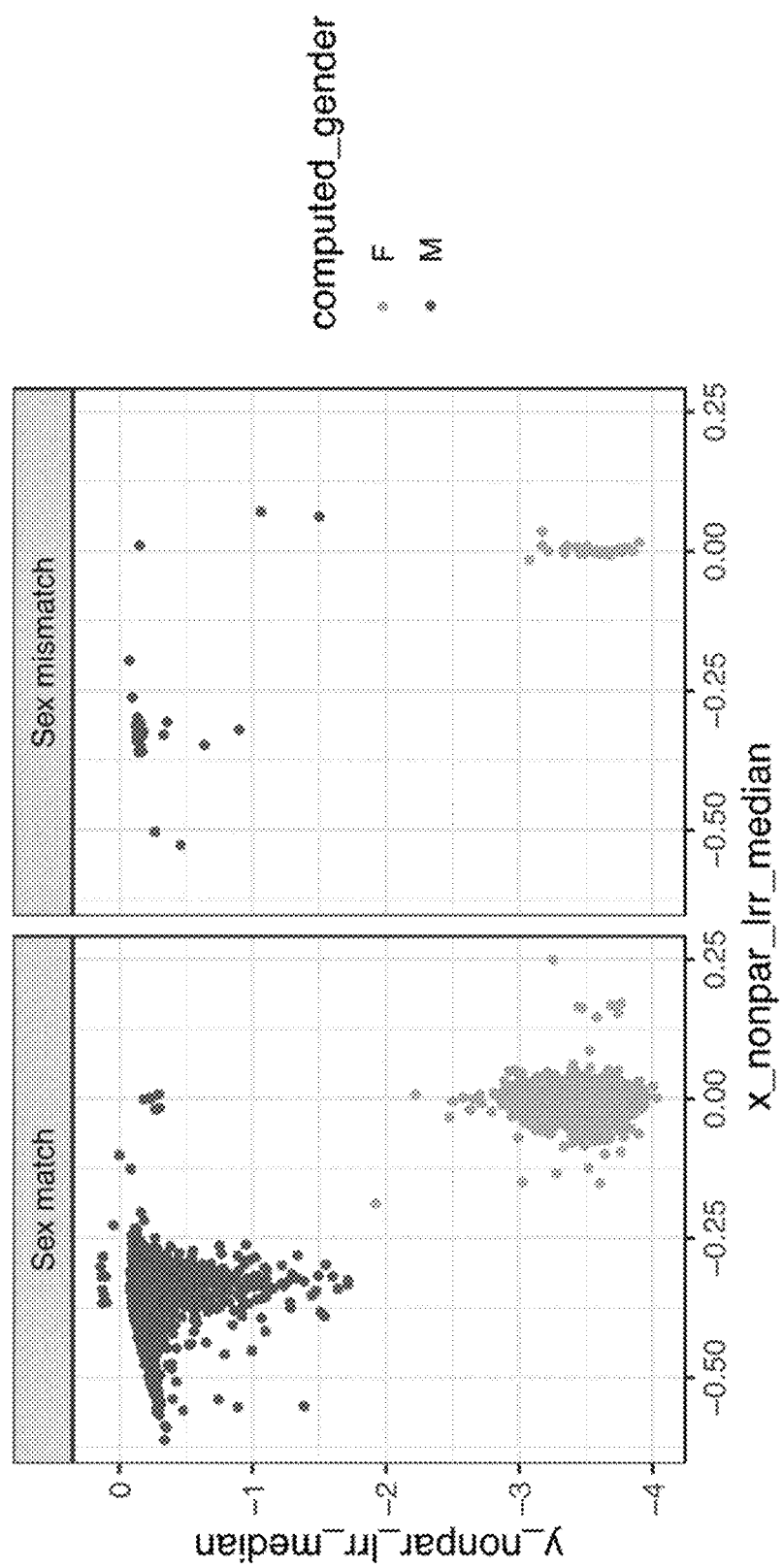
Figure 6A:
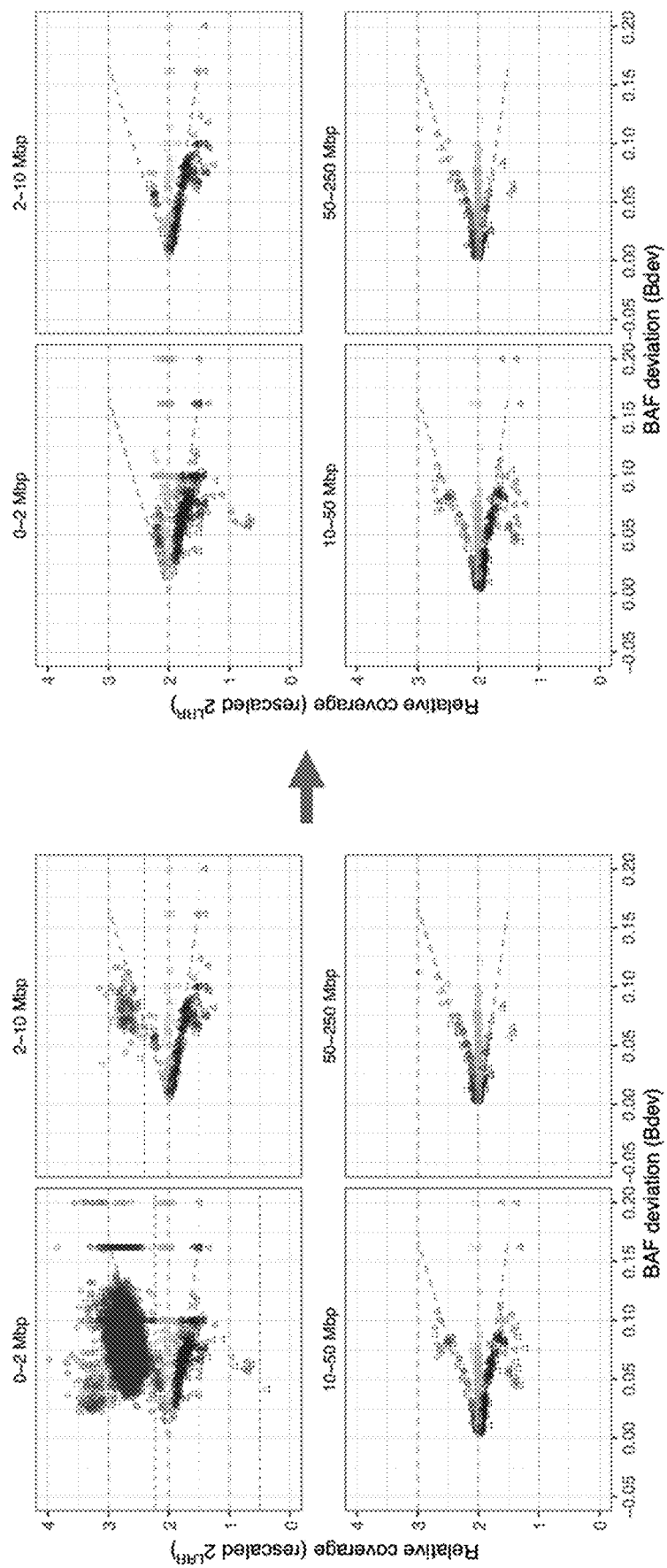
FIGS. 6A and 6B are scatter plots and bar graphs showing Mass General Brigham (MGB) Biobank mosaic chromosomal alteration (mCA) variant quality control analyses. Plots (left and right) The left panels of FIGS. 6A and 6B are a scatter plot and a bar plot showing mosaic chromosomal alterations (mCAs) carried among the quality-control filtered sample set, and after basic variant quality control filters including removal of likely germline variants (LOD_BAF_PHASE<20 for autosomal or mosaic chromosomal alterations (mCAs) annotated as known germline copy number polymorphisms). The right panels of FIGS. 6A and 6B are a scatter plot and a bar plot reflecting additional variant quality control filters to remove constitutional duplications (0-2 Mbp mosaic chromosomal alterations (mCAs) with relative coverage >2.25 and 2-10 Mbp mosaic chromosomal alterations (mCAs) with relative coverage >2.4) and remove constitutional deletions (mosaic chromosomal alterations (mCAs) with relative coverage <0.5). Throughout the figures CN-LOH is used to mean "copy neutral loss-of-heterozygosity". Throughout the figures "chrom" is short for "chromosome".
Figure 6B:
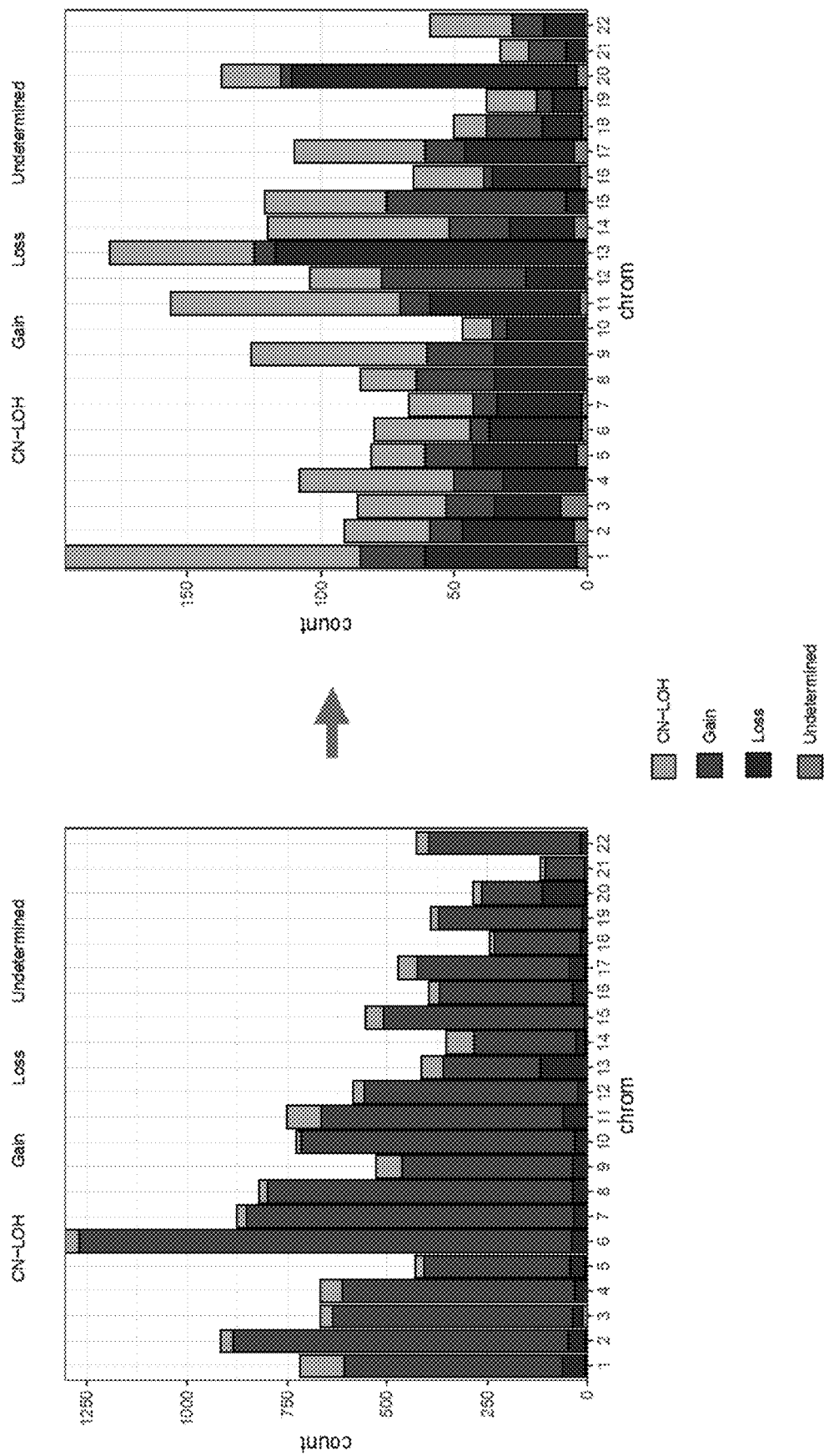

Detection of mosaic chromosomal alterations (mCAs) in the Mass General Brigham (MGB) Biobank was performed starting from raw IDAT intensity files from the Illumina Multi-Ethnic Global Array (MEGA). Genotype clustering was performed using the Illumina GenCall algorithm. The resulting GTC genotype files were converted to VCF files using the bcftools gtc2vcf plugin. Genotype phasing across the whole cohort was performed using SHAPEIT4 in windows of a maximum of 20 centimorgans with 2 centimorgans of overlap between consecutive windows. Phased genotypes were ligated across overlapping windows using BCFtools' concat. mosaic chromosomal alteration (mCA) detection in the Mass General Brigham (MGB) Biobank was performed with MoChA. A pipeline to execute the whole workflow from raw files all the way to final mosaic chromosomal alteration (mCA) calls is available in WDL format for the Cromwell execution engine as part of MoChA. 160 samples were excluded with phased B-allele frequency (BAF) auto-correlation >0.05, indicative of contamination or other potential sources of poor DNA quality, and 67 samples with phenotype-genotype sex discordance (FIGS. 5A and 5B). Likely germline copy number polymorphisms were removed (lod_baf_phase<20 for autosomal variants and lod_baf_phase<5 for sex chromosome variants), constitutional or inborn duplications (mosaic chromosomal alterations (mCAs)<2 Mb with relative coverage >2.25, and mosaic chromosomal alterations (mCAs) 2-10 Mb with relative coverage >2.4) and deletions (filtering out mosaic chromosomal alterations (mCAs) with relative coverage <0.5) were removed (FIGS. 6A and 6B).

The detection of mosaic chromosomal alterations (mCAs) in the Biobank Japan (BBJ) was done as described in Terao C, Suzuki A, Momozawa Y, et al. "Chromosomal alterations among age-related haematopoietic clones in Japan," Nature (2020). Briefly, genotyping intensity data was analysed across variants shared between the three primary arrays, and used to compute BAF and LRR. Phasing was performed using the Eagle2 software. Mosaic events were called as described in Loh P R, Genovese G, Handsaker R E, et al. "Insights into clonal haematopoiesis from 8,342 mosaic chromosomal alterations," Nature (2018) 559:350-5.

Other Phenotype Definitions

Covariate definitions including type 2 diabetes mellitus, hypertension, coronary artery disease, asthma, and chronic obstructive pulmonary disease, are available in the United Kingdom (UK) Biobank. Cancer cases in the UK Biobank were identified using the cancer register (Category 100092) in combination with inpatient ICD-10 registry (Field IDs 41270/41280) and hematologic cancer cases were identified using the cancer registry's Field ID 40011 (haematological cancer identified from biopsy), Field ID 40005/40006 C81-96, D45-47, and inpatient ICD-10 registry (Field ID 41270/41280 C81-96, D45-47). In the Mass General Brigham Biobank (MGBB), cancer cases were identified using ICD-10 C00-D49, and hematologic cancer cases were identified using C81-96, D45-47. Smoking status in MGBB was defined using a combination of electronic health record data and survey data. Follow-up time was coded as time from blood draw for genotyping to event (development of incident phenotype) or, for controls, time from sample collection to either censor date (Oct. 31, 2019) or date of death if the patient died prior to the last censor.

Secondary Statistical Analyses

Secondary associations were performed across other mosaic chromosomal alteration (mCA) exposures: all mosaic chromosomal alterations (mCAs), all expanded autosomal mosaic chromosomal alterations (mCAs), all autosomal mosaic chromosomal alterations (mCAs), all chromosome X (ChrX) mosaic chromosomal alterations (mCAs), expanded ChrX mCAs, all chromosome Y (ChrY) mosaic chromosomal alterations (mCAs), and expanded ChrY mCAs. Of note, approximately 99% of ChrX and ChrY mCA calls were loss of ChrX and ChrY (mLOX and mLOY, respectively). P-value threshold for significance among the secondary exposures was 0.05/10/7=0.0007. Additionally, associations of expanded autosomal mosaic chromosomal alterations (mCAs) with 30 secondary sub-outcomes were performed to detect infection-specific associations. All association analyses were performed adjusted for age, age2, sex, current or prior smoking history, and principal components 1-10 of genetic ancestry. P-value threshold for significance across these secondary analyses accounting for multiple hypothesis-testing was 0.05/30=0.0017.

Sensitivity Analyses

Further sensitivity analyses were performed in the UK Biobank expanded autosomal mosaic chromosomal alteration (mCA) and infection associations. First, stratified cancer analyses were performed among individuals with antecedent cancer prior to their incident infection in both the UK and Mass General Brigham Biobanks, additionally stratifying for the same aforementioned covariates (age, age2, sex, ever smoking status, and the first ten principal components of genetic ancestry). Secondly, interaction analysis was performed using a mCA x antecedent cancer term in the model to analyze the interaction between mCAs and antecedent cancer prior to incident infection. Thirdly, for the incident sepsis association, adding four sets of covariates to the Cox proportional hazards model: 1) normalized body mass index and type 2 diabetes mellitus, 2) any antecedent cancer prior to incident infection, 3) adjusting for a more comprehensive 25-factor smoking phenotype, and 4) adjusting for normalized leukocyte count, lymphocyte count and lymphocyte percentage at baseline visit.

Other Embodiments

From the foregoing description, it will be apparent that variations and modifications may be made to the invention described herein to adapt it to various usages and conditions. Such embodiments are also within the scope of the following claims.

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for identifying a subject at high risk of having or developing a severe respiratory infection or sepsis, the method comprising:
   detecting by one or more computing devices the presence or absence of expanded mosaic chromosomal alterations (mCAs) in DNA derived from a blood or saliva sample of a subject using single-nucleotide polymorphism (SNP) microarray genotype intensity data, wherein the presence of an expanded mCA identifies the subject as at high risk of having or developing the severe respiratory infection or sepsis,
   locating by the one or more computing devices a chromosomal location of each expanded mCA present,
   determining by the one or more computing devices a copy number of each expanded mCA present, and
   providing the subject at high risk of having or developing the severe respiratory infection or sepsis with aggressive treatment,
      wherein the aggressive treatment comprises administering a nucleoside analog to the subject,
         wherein the nucleoside analog is remdesivir.

2. The method of claim 1, wherein the severe respiratory infection or sepsis is viral or bacterial.

3. The method of claim 2, wherein
(a) the virus is severe acute respiratory syndrome coronavirus 2 (SARS-COV-2), severe acute respiratory syndrome coronavirus 1 (SARS-COV-1), influenza A, influenza B, influenza C, Severe Acute Respiratory Syndrome (SARS) virus, human metapneumovirus (hMPV), parainfluenza virus (HPIV), respiratory syncytial virus (RSV), rhinovirus, enterovirus, respiratory syncytial virus, adenovirus, or bocavirus; or
(b) wherein the bacterium is selected from the group consisting of *Mycobacterium tuberculosis, Bordetella pertussis, Streptococcus pneumoniae, Haemophilus influenzae, Staphylococcus aureus, Streptococcus pyogenes*, and *Moraxella catarrhalis*.

4. The method of claim 1, wherein the severe respiratory infection is pneumonia, COVID-19, respiratory tuberculosis, influenza, Severe Acute Respiratory Syndrome (SARS), swine flu, bird flu, whooping cough (pertussis), bronchitis, Middle East Respiratory Syndrome (MERS), pharyngitis, sinusitis, laryngitis, tracheitis, epiglottitis, pyothorax, peritonsillar abscess, abscess of lung, abscess of mediastinum, coccidioidomycosis, histoplasmosis, blastomycosis, paracoccidioidomycosis, sporotrichosis, chromomycosis, phaeomycotic abscess, sporotrichosis, chromomycosis, phaeomycotic abscess, aspergillosis, or orcryptoccosis.

5. The method of claim 1, wherein an expanded mCAs is considered as being present when a single mCA is detected as present in the genomic DNA of at least about 10% of the subject's circulating leukocytes.

6. The method of claim 1, wherein the subject is a mammal.

7. The method of claim 6, wherein the subject is a human.

8. The method of claim 1 further comprising identifying the subject as at high risk of having or developing a severe respiratory infection or sepsis if the subject has a history of cancer.

9. The method of claim 1 further comprising identifying the subject as at high risk of having or developing a severe respiratory infection or sepsis if the subject has an aberrant lymphocyte cell count.

10. A method for prioritizing a subject for viral testing or vaccination, the method comprising:
detecting by one or more computing devices the presence or absence of expanded mosaic chromosomal alterations (mCAs) in DNA derived from a blood or saliva sample of a subject using single-nucleotide polymorphism (SNP) microarray genotype intensity data, wherein the presence of an expanded mCA identifies the subject as at high risk of having or developing a severe respiratory infection or sepsis, thereby indicating that the subject should be prioritized for viral testing or vaccination,
locating by the one or more computing devices a chromosomal location of each expanded mCA present,
determining by the one or more computing devices a copy number of each expanded mCA present, and
providing the subject at high risk of having or developing the severe respiratory infection or sepsis with aggressive treatment,
wherein the aggressive treatment comprises administering a nucleoside analog to the subject,
wherein the nucleoside analog is remdesivir.

11. A method for selecting a subject for aggressive treatment for a severe respiratory infection or sepsis, the method comprising:
detecting by one or more computing devices the presence or absence of expanded mosaic chromosomal alterations (mCAs) in DNA derived from a blood or saliva sample of a subject using single-nucleotide polymorphism (SNP) microarray genotype intensity data, wherein the presence of an expanded mCA identifies the subject, thereby indicating that the subject as in need of aggressive treatment for the respiratory infection or sepsis,
locating by the one or more computing devices a chromosomal location of each expanded mCA present, and
determining by the one or more computing devices a copy number of each expanded mCA present,
wherein the aggressive treatment comprises administering a nucleoside analog to the subject,
wherein the nucleoside analog is remdesivir.

12. The method of claim 11, wherein the aggressive treatment comprises hospitalization.

13. The method of claim 11, wherein the aggressive treatment comprises administering an antibody to the subject.

14. The method of claim 13, wherein the aggressive treatment comprises administering an antibody cocktail to the subject.

15. The method of claim 14, wherein the antibody cocktail is REGN-COV2.

16. The method of claim 11, wherein the aggressive treatment comprises administering convalescent plasma, a monoclonal antibody, or a steroid to the subject.

17. The method of claim 16, wherein the steroid is dexamethasone.

* * * * *